US010406218B2

(12) United States Patent
Sette et al.

(10) Patent No.: US 10,406,218 B2
(45) Date of Patent: Sep. 10, 2019

(54) **SPECIFIC AND UNIQUE T CELL RESPONSES AND MOLECULAR SIGNATURES FOR THE TREATMENT AND DIAGNOSIS OF *MYCOBACTERIUM TUBERCULOSIS***

(71) Applicant: LA JOLLA INSTITUTE FOR ALLERGY AND IMMUNOLOGY, La Jolla, CA (US)

(72) Inventors: Alessandro Sette, La Jolla, CA (US); Bjoern Peters, La Jolla, CA (US); Cecilia Lindestam Arlehamn, La Jolla, CA (US); Greg Seumois, La Jolla, CA (US); Pandurangan Vijayanand, La Jolla, CA (US); Sonia Sharma, La Jolla, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 0 days.

(21) Appl. No.: 15/302,956

(22) PCT Filed: Apr. 9, 2015

(86) PCT No.: PCT/US2015/025184

§ 371 (c)(1),
(2) Date: Oct. 7, 2016

(87) PCT Pub. No.: WO2015/157561

PCT Pub. Date: Oct. 15, 2015

(65) Prior Publication Data

US 2017/0028049 A1 Feb. 2, 2017

Related U.S. Application Data

(60) Provisional application No. 61/977,585, filed on Apr. 9, 2014.

(51) Int. Cl.

| | |
|---|---|
| ***A61K 39/04*** | (2006.01) |
| ***C07K 14/35*** | (2006.01) |
| ***C07K 16/00*** | (2006.01) |
| ***G01N 33/569*** | (2006.01) |
| ***G01N 33/68*** | (2006.01) |
| ***C12N 15/113*** | (2010.01) |

(52) U.S. Cl.

CPC .............. *A61K 39/04* (2013.01); *C07K 14/35* (2013.01); *C07K 16/00* (2013.01); *C12N 15/113* (2013.01); *G01N 33/5695* (2013.01); *G01N 33/6863* (2013.01); *C07K 2317/75* (2013.01); *C07K 2317/76* (2013.01); *C12N 2320/30* (2013.01); *G01N 2333/35* (2013.01)

(58) Field of Classification Search

None

See application file for complete search history.

(56) References Cited

U.S. PATENT DOCUMENTS

| | | | | |
|---|---|---|---|---|
| 8,178,308 | B2 * | 5/2012 | de Waal Malefyt | A61K 38/20 435/375 |
| 8,586,035 | B2 * | 11/2013 | Kopf | C07K 16/244 424/130.1 |
| 2002/0044951 | A1 | 4/2002 | Liu et al. | |
| 2004/0175380 | A1 | 9/2004 | Allison et al. | |
| 2007/0042383 | A1 | 2/2007 | Kapur et al. | |
| 2007/0048261 | A1 * | 3/2007 | Mettens | A61K 39/0008 424/85.2 |
| 2010/0291084 | A1 * | 11/2010 | Kopf | C07K 16/244 424/135.1 |
| 2012/0282290 | A1 | 11/2012 | Spencer et al. | |
| 2017/0028049 | A1 * | 2/2017 | Sette | G01N 33/5695 |

OTHER PUBLICATIONS

Arlehamn et al, J. Immunolog, 2014; 193:2931-2940; Prepublished online Aug. 4, 2014 (Year: 2014).*
Ben-Selma et al, Clinical and Vaccine Immunology, Aug. 2012, 19/8:1188-92 (Year: 2012).*
Daya et al, PloSOne Apr. 28, 2015, 10(4): e0123970. 25 pages. Published Apr. 28, 2015 (Year: 2015).*
Holscher, Current Opinion in Investigational Drugs, 2005, 6/5:489-495 (Year: 2005).*
Jiang et al, BMC Infectious Diseases, 2015, 15:550, 10 pages, published online: Dec. 1, 2015 (Year: 2015).*
Kuchar et al, Proteins, 2014. 82:975-989 (Year: 2014).*
Quiniou et al, Am J Physiol Regul lntegr Comp Physiol 307: R1216-R1230, 2014. (Year: 2014).*
Nicol et al. Vet Res (2016) 47:27 (Year: 2016).*
Woznaik et al, Infection and Immunity, 2006, 74/1:557-565 (Year: 2006).*
Sanal et al, J. Clinical Immunology, Jan. 2006, 26/1:1-6 (Year: 2006).*
Ghoreschi et al. "Modulation of Innate and Adaptive Immune Responses by Tofacitinib (CP-690,550)," J Immunol, Mar. 7, 2011 (Mar. 7, 2011 ), vol. 186, pp. 4234-4243.
Barnes et al. "Patterns of Cytokine Production by *Mycobacterium*-Reactive Human T-Cell Clones," Infection and Immunity, Jan. 1993, vol. 61, No. 1, pp. 197-203.
Musser et al. "Negligible Genetic Diversity of *Mycobacterium tuberculosis* Host Immune System Protein Targets: Evidence of Limited Selective Pressure," Genetics, May 2000, vol. 155: 7-16.
PCT International Search Report, PCT/US2015/025184, dated Aug. 26, 2015.

* cited by examiner

*Primary Examiner* — Nita M. Minnifield

(74) *Attorney, Agent, or Firm* — Pillsbury Winthrop Shaw Pittmann LLP

(57) ABSTRACT

The invention relates to novel targets for immune response modulation, treatment of tuberculosis infection and epitopes of *Mycobacterium tuberculosis*, or subsequences, portions or modifications thereof, and methods and compounds for treatment and prevention of tuberculosis infection.

3 Claims, 13 Drawing Sheets

Specification includes a Sequence Listing.

SPECIFIC AND UNIQUE T CELL RESPONSES AND MOLECULAR SIGNATURES FOR THE TREATMENT AND DIAGNOSIS OF *MYCOBACTERIUM TUBERCULOSIS*

RELATED APPLICATION INFORMATION

This application is the National Phase of International Application No. PCT/US2015/025184, filed Apr. 9, 2015, which designated the U.S. and that International Application was published under PCT Article 21(2) in English, which claims priority to Application Ser. No. 61/977,585, filed Apr. 9, 2014, all of which applications are expressly incorporated herein by reference in their entirety.

GOVERNMENT SUPPORT

This invention received government support from the National Institutes of Health Contract HHSN-272200900042C. The government has certain rights in the invention.

FIELD OF THE INVENTION

The invention relates to novel targets for treatment of tuberculosis infection and epitopes of *Mycobacterium tuberculosis*, or subsequences, portions or modifications thereof and methods and compounds comprising the same for treatment and prevention of tuberculosis infection.

INTRODUCTION

Tuberculosis is a major threat to global health and one of the major causes of death from infectious disease. One-third of the world's population is latently infected with *M tuberculosis* (MTB). Most cases of active disease will arise from this enormous reservoir of latent TB, resulting in further spread of the disease, which embodies a major obstacle in achieving worldwide control of TB (WHO, 2011). Current diagnostics cannot distinguish between active and latent infection, and the only available vaccine against TB has limited efficacy. Further the increasing incidence of drug resistant strains has prompted their inclusion in the list of A-C pathogens, and heightened interest in development of effective vaccines. Therefore, there is a need for the development of novel vaccines and diagnostic strategies (Wallis et al., 2010).

Human T cell responses to MTB involve CD4+, CD8+ and γ∂ T cells (Boom, 1996). CD4 T cells have been shown to be central to the defense against MTB through the discovery that HIV infected patients are more susceptible to primary TB infection, re-infection and re-activation (Barnes et al., 1991). Different types of CD4 T helper (Th) cells develop from naïve T cells under the influence of polarizing signals and master transcription factors. Seminal studies showed that human memory T cells directed against MTB secreted IFN-γ, thus representing the human counterpart of mouse Th1 cells (Del Prete et al., 1991). IFN-γ has an essential role in the protective immunity to mycobacteria, as demonstrated by the increased susceptibility to mycobacteria in individuals with genetic defects in the IFN-γ receptor (Newport et al., 1996). Furthermore, different Th cell subsets differ in expression of chemokine receptors and therefore in migratory capacity and tissue localization (Sallusto et al., 2000). Th1 cells mainly express CCR5 and CXCR3 (Sallusto et al., 1998), while Th17 cells co-express CCR6 and CCR4 and Th22 cells co-express CCR6 and CCR10 (Acosta-Rodriguez et al., 2007; Duhen et al., 2009)

SUMMARY

The invention is based, in part, on the discovery of novel *Mycobacterium tuberculosis* and non-tuberculosis *mycobacterium* T cell epitopes and use of such epitopes in treatment and vaccination methods. In particular embodiments, the invention provides proteins and peptides comprising amino acid sequences of *Mycobacterium tuberculosis* and non-tuberculosis *mycobacterium* proteins, and subsequences, portions or modifications, and methods and compounds comprising such protein and peptides for the treatment, diagnosis and prevention of *Mycobacterium tuberculosis* and non-tuberculosis *mycobacterium* infection.

This invention provides methods and compounds for the development of diagnostics, vaccines and therapeutics for *Mycobacterium tuberculosis* (MTB) and Non-tuberculose *mycobacterium* (NTM) infection and autoimmune or allergic disease in humans. In particular aspects, specific molecules are disclosed herein, including cell surface markers, chemokine receptors and molecular pathways, which alone or in combination are up- and down-regulated in TB infection. In particular aspects molecules may be targeted by various means (i.e. antibodies and/or small-molecules) to cure TB infection or minimally dampen inflammation associated with active TB infection or the cavitation phase of the disease. In additional aspects, these molecules or pathways may also be targeted in diseases associated with inappropriate inflammation such as in autoimmune disorders like Rheumatoid Arthritis juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 11 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome, allergy or Behcet's disease.

In another embodiment, a number of epitopes and antigens are disclosed herein that allow the differential diagnosis of MTB and Non-tuberculose mycobacteria (NTM) infection. In additional aspects, these data have additional value in allowing the design of both MTB specific and NTM/MTB cross-reactive or, "naturally boosted" vaccines. In further aspects, the NTM epitopes and antigens identified can additively be used to monitor the performance of NTM-based vaccines.

In additional embodiments, a set of broadly cross-reactive T cell epitopes are disclosed herein, which elicit production of the anti-inflammatory cytokine, IL-10, that can be used to dampen inflammation associated with severe active TB cases as well as other infectious, auto-immune, and allergic disease. These epitopes and/or antigens can also be used to generate novel BCG vaccines where potentially anti-inflammatory antigens/epitopes can be removed to enhance the efficacy of BCG-based vaccines for MTB disease.

Thus, in one aspect there is provided a method of modulating an immune response, comprising administration of a therapeutically effective amount of an agonist or antagonist of one or more of the proteins in Table 1. In another aspect there is provided a method of modulating an immune response, comprising administration of a therapeutically effective amount of an agonist or antagonist of Th* activity. In particular aspects, the method comprises modulating expression or activity of one or more of the proteins in Table 1. In additional aspects, the method comprises increasing, stimulating, enhancing, promoting, inducing or activating the immune response. In further aspects, the method comprises increasing, stimulating, enhancing, promoting, inducing or activating the immune response to treat *Mycobacterium tuberculosis* infection. In further aspects, the method treats the cavitation phase of *Mycobacterium tuberculosis* infection. In additional aspects, the method comprises decreasing, reducing, inhibiting, suppressing, limiting or controlling the immune response. In additional aspects, the method comprises decreasing, reducing, inhibiting, suppressing, limiting or controlling the immune response to treat an aberrant immune response. In further aspects, the proteins in Table 1 are differentially expressed by Th* cells.

In another embodiment, there is provided a method of modulating Th* activity, comprising administration of an agent which modulates expression or activity of one or more of the proteins in Table 1. In particular aspects, the method comprises contacting a protein of Table 1 with an agent that modulates the expression or activity of the protein. In particular aspects, the agent increases expression or activity of the protein. In additional aspects, the agent decreases expression or activity of the protein. In further aspects, the agent comprises a small molecule agonist or antagonist of the protein of Table 1. In additional aspects, the agent comprises a fragment of the protein of Table 1 that agonizes or antagonizes the protein of Table 1. In additional aspects, the agent comprises a fusion polypeptide or chimeric polypeptide that agonizes or antagonizes the protein of Table 1. In further aspects, the agent comprises an inhibitory nucleic acid that agonizes or antagonizes the protein of Table 1. In particular aspects, the inhibitory nucleic acid comprises a RNAi, siRNA or miRNA. In further aspects, the agent comprises an antibody or antibody fragment thereof that binds to the protein of Table 1 and agonizes or antagonizes the protein of Table 1.

In another embodiment, there is provided a method of modulating an immune response in a subject, comprising administering a therapeutically effective amount of an agent that agonizes or antagonizes the expression or activity of one or more of the proteins in Table 1. In particular aspects, the method comprises decreasing, reducing, inhibiting, suppressing, limiting or controlling in the subject an undesirable or aberrant immune response, disorder or disease, an inflammatory response, disorder or disease, inflammation, or an autoimmune response, disorder or disease, or an adverse symptom of an undesirable or aberrant immune response, disorder or disease, an inflammatory response, disorder or disease, inflammation or an autoimmune response, disorder or disease. In further aspects, the method comprises increasing, stimulating, enhancing, promoting, inducing or activating in a subject an immune response, inflammatory response or inflammation. In additional aspects, the subject has or has had an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In additional aspects, the subject is in need of treatment for an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In further aspects, the subject is at risk of an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In additional aspects, the immune response or inflammatory response is an anti-pathogen or anti-cancer immune response or inflammatory response. In further aspects, the undesirable or aberrant immune response, disorder or disease, inflammatory response, disorder or disease, inflammation, or autoimmune response, disorder or disease comprises rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 11 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, severe combined immunodeficiency (SCID), recombinase activating gene (RAG 1/2) deficiency, adenosine deaminase (ADA) deficiency, interleukin receptor common γ chain (γc) deficiency, Janus-associated kinase 3 (JAK3) deficiency and reticular dysgenesis; primary T cell immunodeficiency such as DiGcorge syndrome, Nude syndrome, T cell receptor deficiency, MHC class II deficiency, T AP-2 deficiency (MHC class I deficiency), ZAP70 tyrosine kinase deficiency and purine nucleotide phosphorylase (PNP) deficiency, antibody deficiencies, X-linked agammaglobulinemia (Bruton's tyrosine kinase deficiency), autosomal recessive agammaglobulinemia, Mu heavy chain deficiency, surrogate light chain (γ5/14.1) deficiency, Hyper-IgM syndrome: X-linked (CD40 ligand deficiency) or non-X-linked, Ig heavy chain gene deletion, IgA deficiency, deficiency of IgG subclasses (with or without IgA deficiency), common variable immunodeficiency (CVID), antibody deficiency with normal immunoglobulins; transient hypogammaglobulinemia of infancy, interferon γ receptor (IFNGR1, IFNGR2) deficiency, interleukin 12 or interleukin 12 receptor deficiency, immunodeficiency with thymoma, Wiskott-Aldrich syndrome (WAS protein deficiency), ataxia telangiectasia (ATM deficiency), X-linked lymphoproliferative syndrome (SH2D1A/SAP deficiency), hyper IgE syndrome or Graft vs. Host Disease (GVHD).

In another embodiment, there is provided a protein or peptide comprising, consisting of or consisting essentially of an amino acid sequence set forth in Table 2 or Table 3 or a variant thereof or derivative thereof. In another embodiment, there is provided a composition comprising the protein or peptide set forth in Table 2 or Table 3. In another embodiment, there is provided, a pharmaceutical composition comprising a protein or peptide set forth in Table 2 or Table 3 and a biologically acceptable excipient.

In another embodiment, there are provided methods of providing a subject with protection against a *Mycobacterium tuberculosis* (MTB) or non-tuberculosis *mycobacterium* (NTM) infection pathology, or one or more physiological conditions, disorders, illnesses, diseases, symptoms or complications caused by or associated with MTB or NTM infection or pathology. In particular aspects, a method includes administration of an effective amount of a protein or peptide set forth in Table 2 or Table 3, sufficient to provide the subject with protection against the MTB or NTM infection or pathology, or one or more physiological conditions, disorders, illnesses diseases, symptoms or complications caused by or associated with the MTB or NTM infection or pathology. In particular aspects, a method comprises vaccinating or protecting a subject against a *Mycobacterium tuberculosis* (MTB) or non-tuberculosis *mycobacterium* (NTM) infection. In further aspects, the method comprises administering to the subject the protein or peptide in combination with an immunological agent, wherein the subject is administered an amount of the protein or peptide sufficient to vaccinate or protect the subject against the MTB or NTM infection when the protein or peptide is administered in combination with the immunological agent. In additional aspects, the method comprises eliciting, stimulating, inducing, promoting, increasing or enhancing a T cell response against *M. tuberculosis* (MTB) or non-tuberculosis *mycobacterium* (NTM). In further aspects, the method comprises eliciting, stimulating, inducing, promoting, increasing or enhancing a CD4+ T cell response against *M. tuberculosis* (MTB) or non-tuberculosis *mycobacterium* (NTM).

In another embodiment, there is provided a method of detecting a *M. tuberculosis* (MTB) or non-tuberculosis *mycobacterium* infection in a subject, the method comprising: i) obtaining a blood sample from the subject, ii) isolating PBMC from the blood sample, iii) contacting PBMC from the subject with the protein or peptide of claim 27, and iv) measuring the cytokine response of the cells, wherein a cytokine response detects the infection in the subject. In another embodiment, there is provided a method of detecting a *M. tuberculosis* (MTB) or non-tuberculosis *mycobacterium* infection in a subject, the method comprising: i) contacting PBMC from the subject with the protein or peptide of claim 27, and ii) measuring the cytokine response of the cells, wherein a cytokine response detects the infection in the subject. In particular aspects, the method differentiates detection of *M. tuberculosis* infection from non-tuberculosis *mycobacterium* infection.

In another embodiment, there is provided a protein or peptide comprising, consisting of or consisting essentially of an amino acid sequence set forth in Table 3 or a variant thereof or derivative thereof. In another embodiment, there is provided a method of providing a subject with treatment or protection against a *Mycobacterium tuberculosis* (MTB) infection pathology, or one or more physiological conditions, disorders, illnesses, diseases, symptoms or complications caused by or associated with MTB infection or pathology, the method comprising administration of an effective amount of the protein or peptide, sufficient to provide the subject with protection against the MTB infection or pathology, or one or more physiological conditions, disorders, illnesses diseases, symptoms or complications caused by or associated with the MTB infection or pathology. In particular aspects, the method comprises vaccinating or protecting a subject against a *Mycobacterium tuberculosis* (MTB) infection. In additional aspects, the method comprises treating a subject against a *Mycobacterium tuberculosis* (MTB) infection. In further aspects, the method comprises administering to the subject the protein or peptide in combination with an immunological agent, wherein the subject is administered an amount of the protein or peptide sufficient to vaccinate or protect the subject against the MTB infection when the protein or peptide is administered in combination with the immunological agent. In further aspects, the immunological agent is administered before, concurrently or after the administration of the protein or peptide. In further aspects, the method comprises eliciting, stimulating, inducing, promoting, increasing or enhancing a T cell response against *M. tuberculosis* (MTB). In additional aspects, the method comprises eliciting, stimulating, inducing, promoting, increasing or enhancing a CD4+ T cell response against *M. tuberculosis* (MTB). In further aspects, the method comprises eliciting, stimulating, inducing, promoting, increasing or enhancing an IL-10 response against *M. tuberculosis* (MTB).

In another embodiment, there is provided a method of providing a subject with treatment for an infectious disesase or disorder, autoimmune disease or disorder or allergic disease or disorder. In one aspect, a method includes administration of an effective amount of a protein or peptide consisting of or comprising an amino acid sequence of Table 3 sufficient to provide the subject with protection against the infectious disease or disorder, autoimmune disease or disorder or allergic disease or disorder.

Dot plots show expression for each individual sample tested. Data represents median±SEM (B) Differentially expressed genes between Th1, Th17 and Th* (top panel), Th* in LTBI vs. HC (bottom left panel), tetramer+vs. Th* (bottom right panel). C) Number of differentially expressed genes for all possible comparisons of Th subsets in LTBI and HC. (D) Number of differentially expressed genes comparing donor cohorts and TB-specific cells vs. LTBI or HC.

Figure 4:
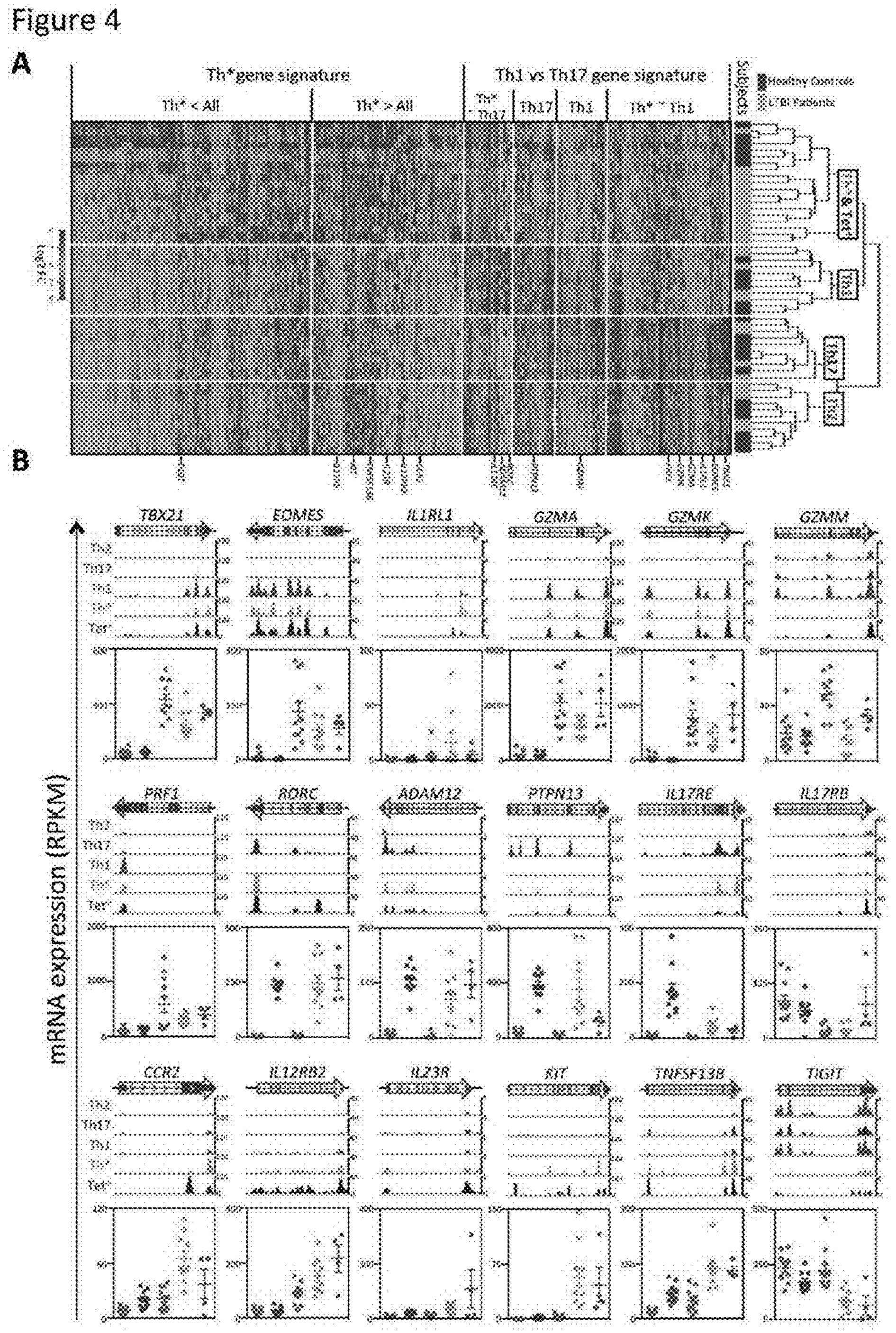

FIG. 4. Heatmap comparing the expression level of genes across different Th subsets and mRNA expression of specific genes of interest.

Figure 5:
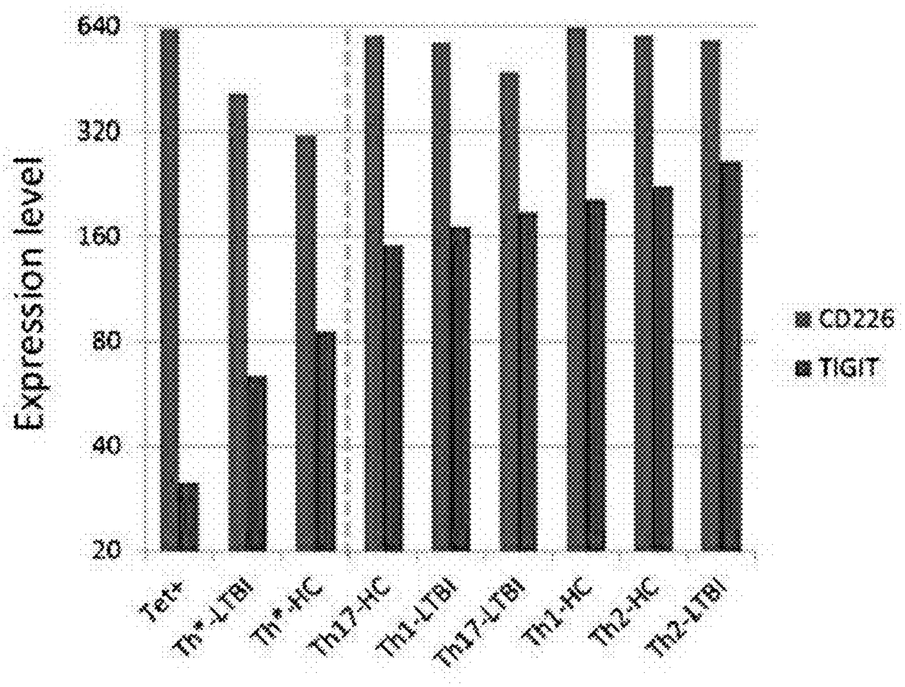

FIG. 5. TB-specific cells represents the most immune reactive cells in the Th* compartment based on TIGIT and CD226 expression. Median expression levels of TIGIT (red bars) and CD226 (blue bars) in tetramer+ cells and T cell subsets from LTBI (n=x) and HC (n=x) donors.

Figure 6:
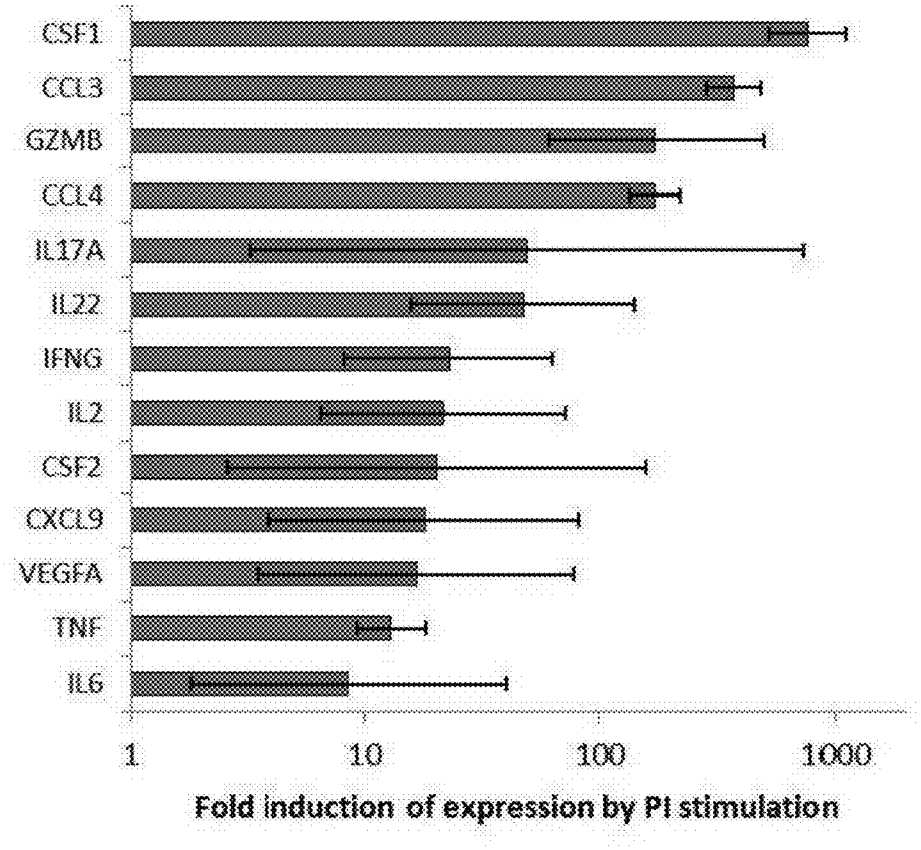

FIG. 6. Cytokine genes upregulated in activated Th* cells

Figure 7:
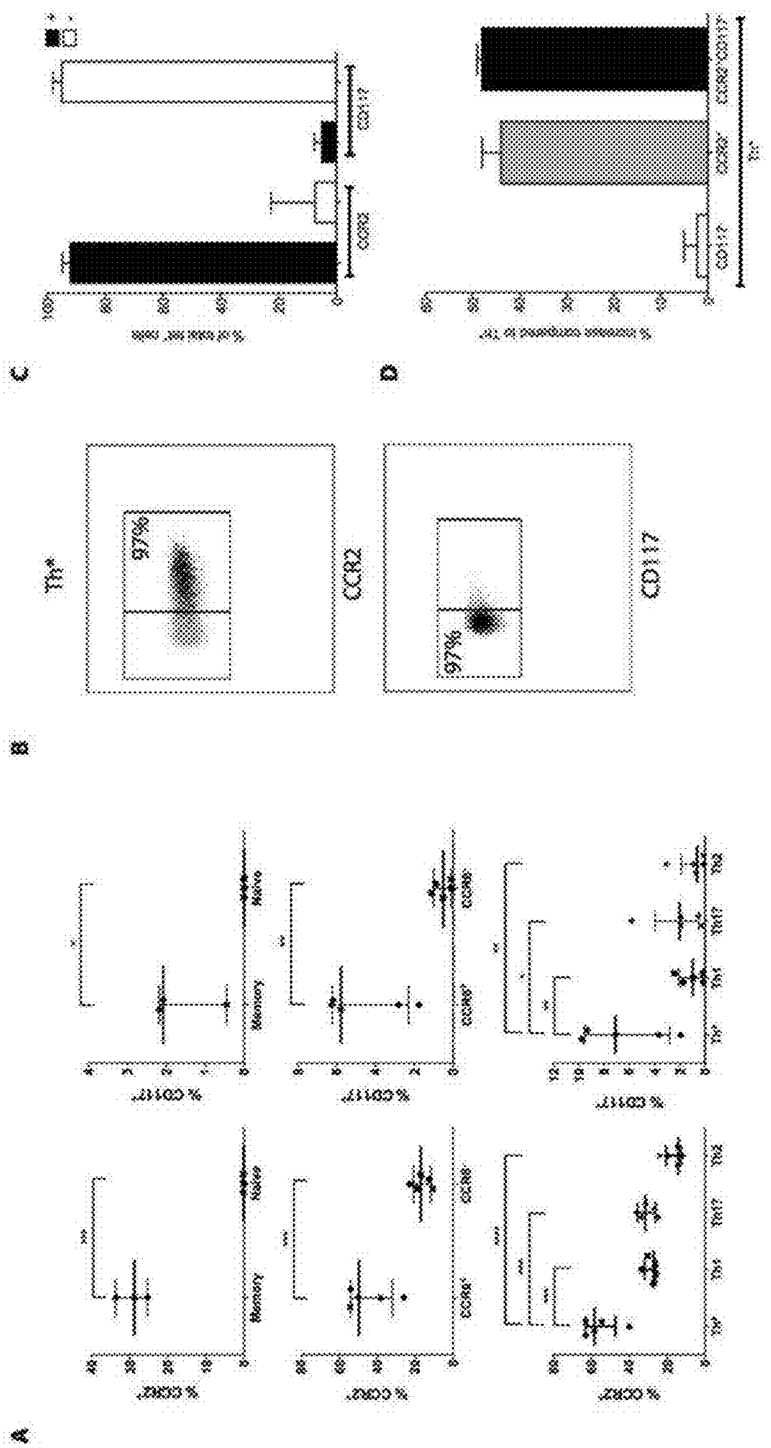

FIG. 7. The transcriptional profile of the Th* subset is reflected by a similar expression profile of proteins. (A) CD4+ T cells were stained for CCR2 and CD117 and expression was compared between different subsets. Top panel; memory vs. naïve T cells, middle panel; CCR6+ vs. CCR6−, bottom panel; Th*, Th1, Th17 and Th2. Each dot represents one donor, median±interquartile range is indicated. Unpaired one-tailed t test, *, $p<0.05$, , $p<0.01$, *, $p<0.001$, ****, $p<0.0001$. (B) CCR2 (top) and CD117 (bottom) expression in tet+Th* cells (black dots) compared to Th* (grey dots). (C) % of tet+Th* cells expressing CCR2 and CD117. Data represent median±interquartile range from 3 donors. (D) % increase in tetramer+ cells compared to Th* if CCR2+ and/or CD117− is included in the staining panel. Data represent median±interquartile range from 3 donors.

Figure 8:
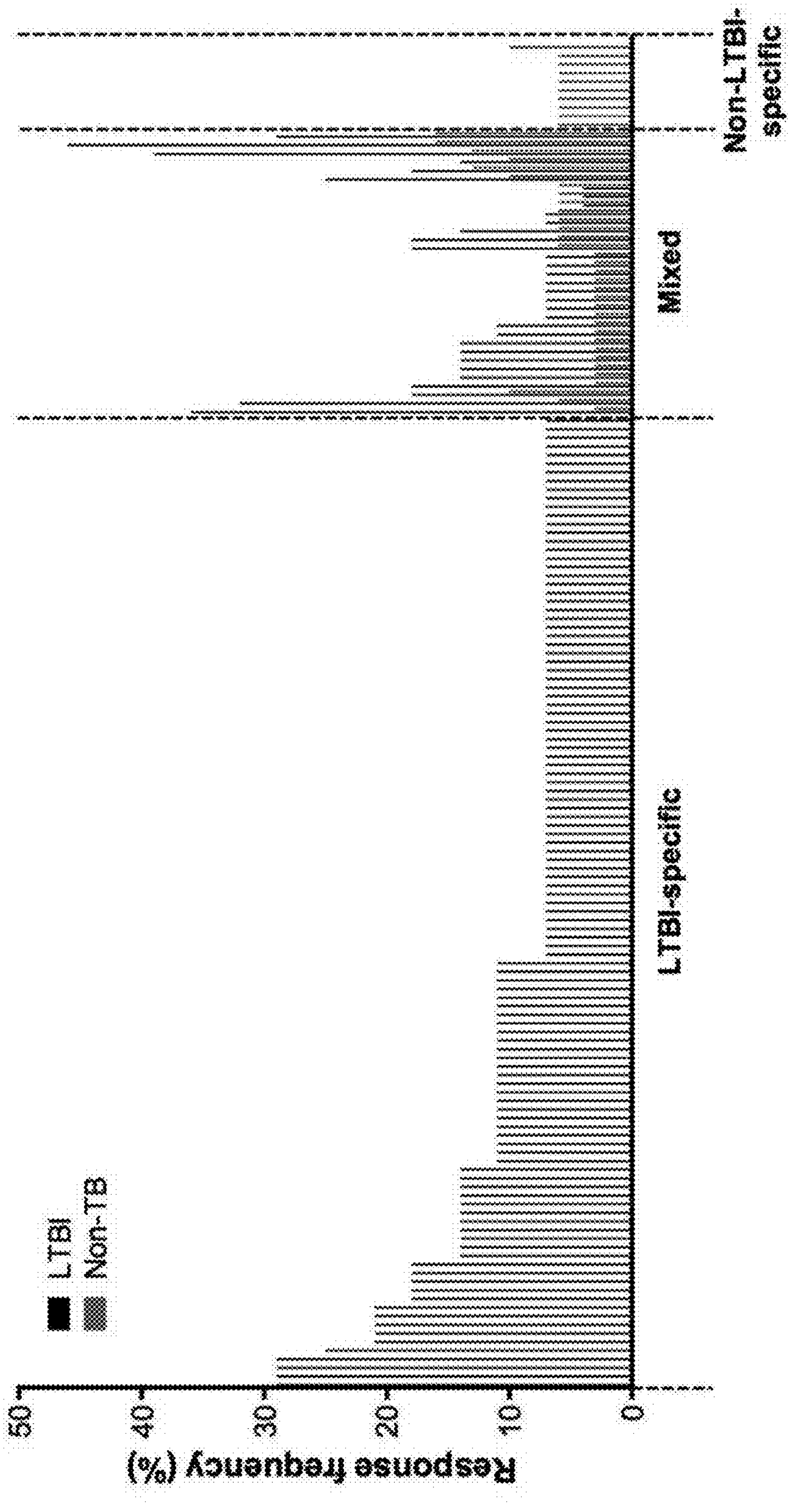

FIG. 8. Responses to MTB derived peptide pools in Non-TB donors. Epitopes recognized by 2 or more LTBI (black bars) and HC (red bars) donors divided into three categories of reactivity; LTBI-specific, mixed and non-LTBI-specific.

Figure 9:
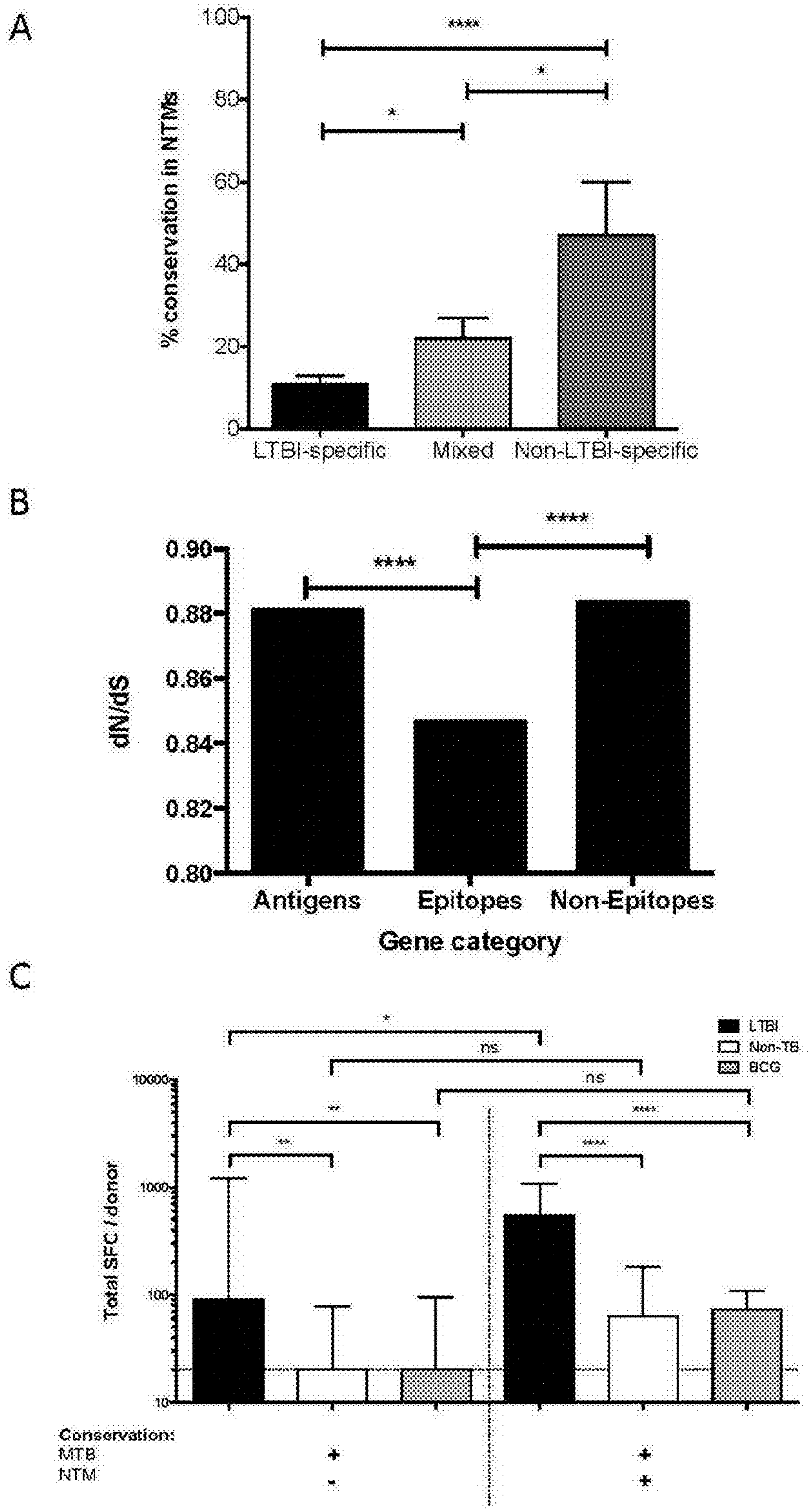

FIG. 9. Conservation of LTBIspecific, mixed and non-LTBI specific epitopes in 15 NTM. Unpaired t test, *, $p<0.05$, **, $p<0.0001$. (B) dN/dS in LTBIspecific epitopes compared to nonepitope regions and antigens as a whole. Epitope regions were found to be more conserved that non-epitopes and antigens. Mann-Whitney test, **, $p<0.0001$. (C) Magnitude of peptide pool responses following division based on conservation in MTB or MTB/NTM in LTBI (n=20), HC (n=20) and BCG (n=19). Median± interquartile range is indicated. One-tailed Mann Whitney test, *, $p<0.05$, , $p<0.01$, **, $p<0.0001$, ns, not significant. Dashed line at 20 SFC indicates threshold of positivity.

Figure 10:
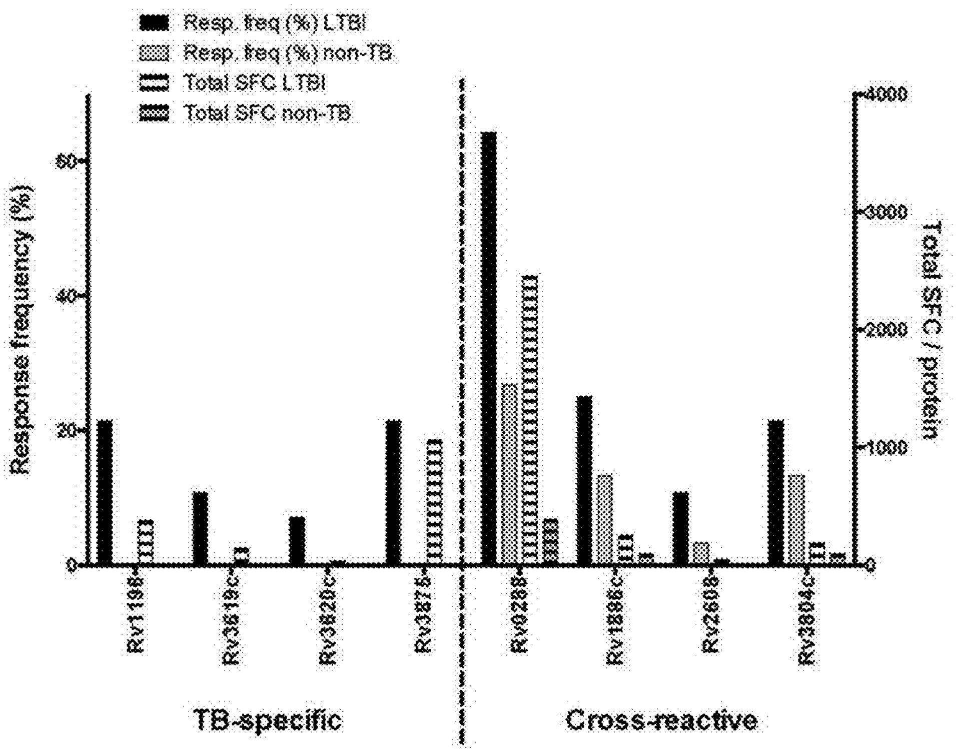

FIG. 10. Antigenic basis of differential reactivity

Figure 11:
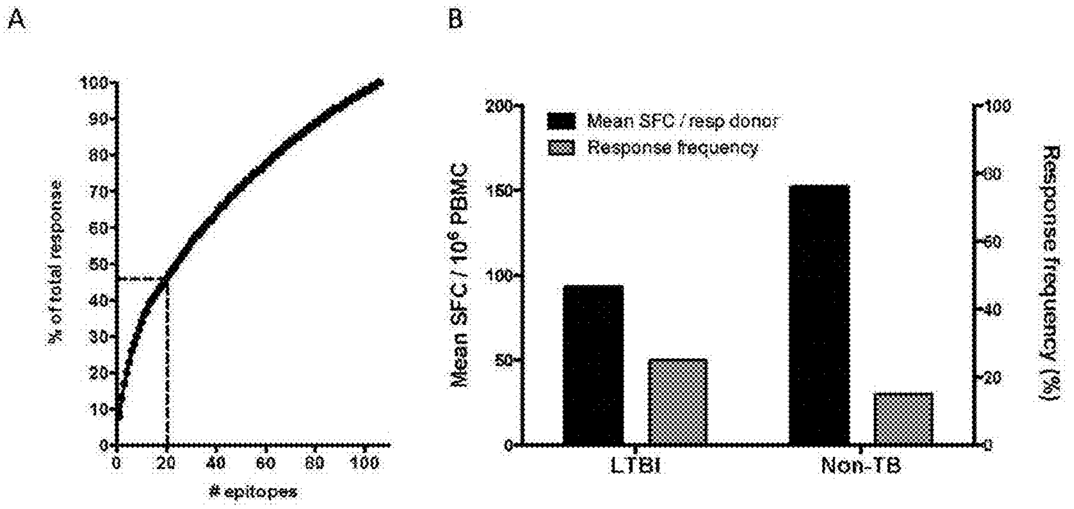

FIG. 11. Definition of NTM-specific epitopes. (A) Identified epitopes plotted as a function of the percentage of the total response. Black dashed lines indicate the top 20 epitopes. (B) T cell reactivity in LTBI and HC donors to the top 20 NTM-specific epitopes. Shown are the response frequency (Grey bars) and the average magnitude of response for responding donors (Black bars).

Figure 12:
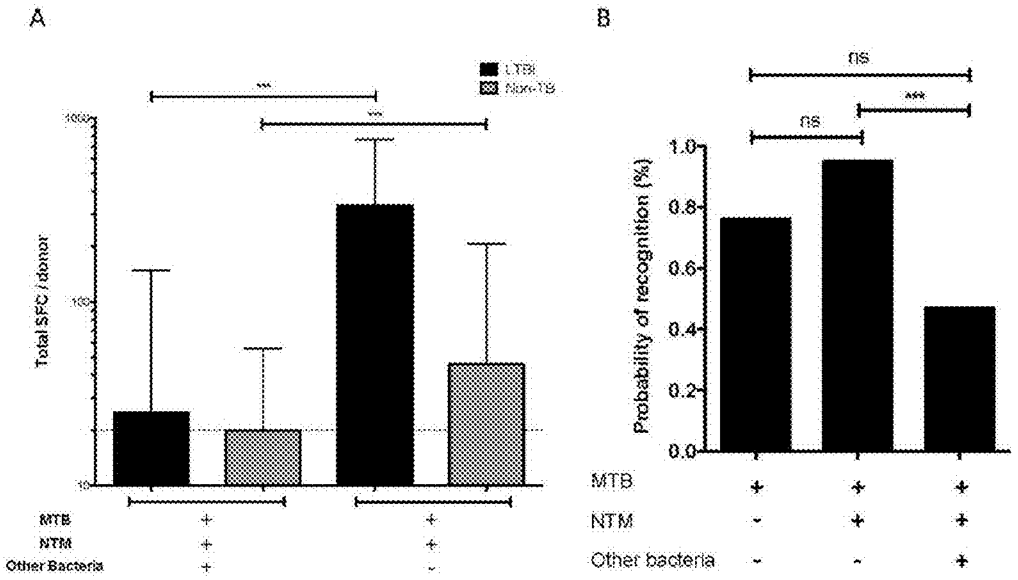

FIG. 12. Broadly conserved epitopes are recognized less frequently. (A) Magnitude of peptide pool responses following division based on conservation in MTB/NTM or broadly conserved in LTBI (n=19) and HC (n=26). Median±interquartile range is indicated. One-tailed Mann Whitney test, *, $p<0.001$. Dashed line at 20 SFC indicates threshold of positivity. (B) % Probability of recognition of peptides conserved in MTB, MTB/NTM or broadly conserved. Chi test, *, $p<0.001$, ns, not significant.

Figure 13:
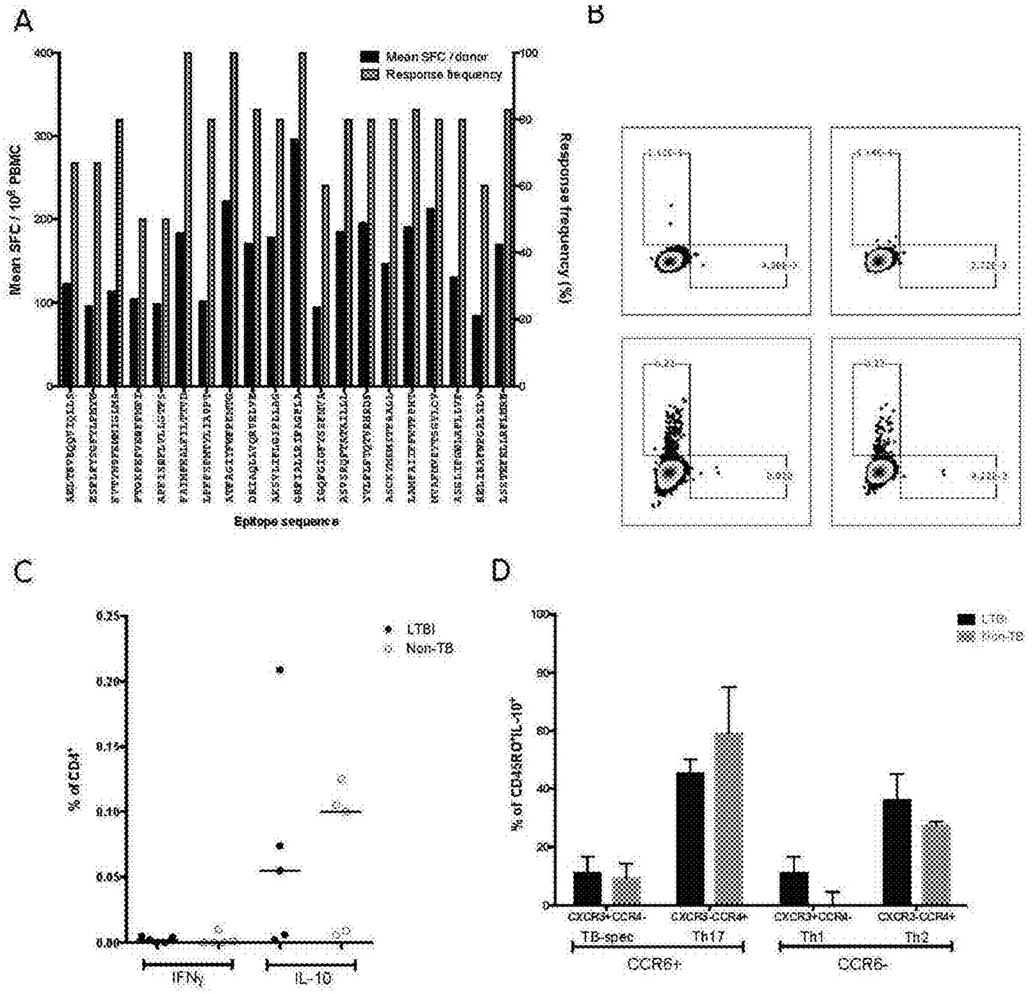

FIG. 13. (A) T cell reactivity in HC donors to the most frequently recognized IL-10 epitopes. Shown are the response frequency (Grey bars) and the average magnitude of response (Black bars). (B) IL-10 pool-specific IL-10 and IFNγ production by CD4+ T cells measured after 6 h stimulation. Representative FACS dot plots from LTBI (left panel) and HC donor (right panel). Plots are gated on total CD4+ T cells stimulated with media (control, top panel) or peptide pool (bottom panel). (C) % of responding CD4+ T cells expressing IFNγ or IL-10. Each dot represents one donor; median±interquartile range is indicated. (D) % of CD45RO+IL-10+ T cells divided into 4 Th subsets; CXCR3+CCR6+CCR4−, CXCR3+CCR6−CCR4− (Th1), CXCR3−CCR6+CCR4− (Th17), and CXCR3−CCR6−CCR4+ (Th2) cells. Data represent median±interquartile range from 5 LTBI donors (Black bars) and 5 HC donors (grey bars).

DETAILED DESCRIPTION

The invention is based, in part, on the discovery of differentially expressed genes/proteins that characterize a Th cell line denoted Th*. Such genes, and proteins encoded by the genes, are useful as targets for modulating an immune response, such as a response conferred or mediated, in part, by T cells such as Th* cells. In particular embodiments, the invention provides methods of modulating an immune response using an agent that binds to or regulates expression or activity of one or more proteins set forth in Table 1. Such agents include agonists, antagonists and null agents, e.g., agents that bind but may not exhibit detectable agonist or antagonist activity, e.g., may not affect expression, activity or function of a nucleic acid encoding a protein set forth in Table 1, or a protein set forth in Table 1.

The invention is also based, in part, on the discovery of novel *Mycobacterium tuberculosis* and non-tuberculosis *mycobacterium* T cell epitopes and use of such epitopes in treatment and vaccination methods and uses. In particular embodiments, the invention provides proteins and peptides comprising amino acid sequences of *Mycobacterium tuberculosis* and non-tuberculosis *mycobacterium* proteins, and subsequences, portions or modifications, and methods and compounds comprising such protein and peptides for the treatment, diagnosis and prevention of *Mycobacterium tuberculosis* and non-tuberculosis *mycobacterium* infection.

Compositions, methods and uses herein include full length polypeptides, and subsequences and fragments thereof. In one embodiment, a polypeptide subsequence or fragment is characterized as including or consisting of a full-length or a subsequence of a protein set forth in any of Tables 1-4. In another embodiment, a polypeptide, subsequence or fragment is characterized as including or consisting of a protein which serves as a target for immune response modulation (e.g. a protein or nucleic acid encoding a protein set forth in Table 1), or can itself function to modulate an immune response (e.g., as disclosed, for example, in the Examples herein). Such polypeptide sequences, subsequences/fragments, variants and derivatives, and polymorphisms as set forth herein, are also included as compositions, methods and uses.

As used herein, a "polypeptide" or "peptide" refers to two, or more, amino acids linked by an amide or equivalent bond. A polypeptide can also be referred to herein, inter alia, as a protein, or an amino acid sequence, or simply a sequence. Polypeptides include L- and D-isomers, and combinations of L- and D-isomers. Polypeptides can form intra or intermolecular disulfide bonds. Polypeptides can also form higher order structures, such as multimers or oligomers, with the same or different polypeptide, or other molecules. The polypeptides can include modifications typically associated with post-translational processing of proteins, for example, cyclization (e.g., disulfide bond), phosphorylation, glycosylation, carboxylation, ubiquitination, myristylation, acetylation (N-terminal), amidation (C-terminal), or lipidation. Polypeptides described herein further include compounds having amino acid structural and functional analogues, for example, peptidomimetics having synthetic or non-natural amino acids or amino acid analogues, so long as the mimetic has one or more functions or activities of a native polypeptide set forth herein. Non-natural and non-amide chemical bonds, and other coupling means can also be included, for example, glutaraldehyde, N-hydoxysuccinimide esters, bifunctional maleimides, or N, N'-dicyclohexylcarbodiimide (DCC). Non-amide bonds can include, for example, ketomethylene aminomethylene, olefin, ether, thioether and the like (see, e.g., Spatola (1983) in *Chemistry and Biochemistry of Amino Acids, Peptides and Proteins*, Vol. 7, pp 267-357, "Peptide and Backbone Modifications," Marcel Decker, NY).

A subsequence or fragment of polypeptide includes or consists of one or more amino acids less than full length polypeptide. The term "subsequence" or "fragment" means a portion of the full length molecule. A subsequence of a polypeptide sequence has one or more one or more internal or terminal amino acid deletions from either amino or carboxy-termini). Subsequences therefore can be any length up to the full length native molecule, provided said length is at least one amino acid less than full length native molecule.

Subsequences can vary in size, for example, from a polypeptide as small as an epitope capable of binding an antibody or binding/activating T cells (i.e., about five to about eight amino acids) up to a polypeptide that is one amino acid less than the entire length of a reference polypeptide. Non-limiting exemplary subsequences less than full length include, for example, a subsequence from about 5 to 10, 10 to 20, 20 to 30, 30 to 50, 50 to 100, 100 to 150, 150 to 200, 200 to 250, 250 to 300, 300 to 400, or 400 to 500, amino acids in length.

As used herein, subsequences may also include or consist of one or more amino acid additions or deletions, wherein the subsequence does not comprise full length sequence. Accordingly, total subsequence lengths can be greater than the length of full length native/wild type polypeptide, for example, where a subsequence is fused or forms a chimera with another heterologous polypeptide.

As used herein, the terms "polynucleotide" and "nucleic acid" are used interchangeably to refer to all forms of nucleic acid, oligonucleotides, primers, and probes, including deoxyribonucleic acid (DNA) and ribonucleic acid (RNA). Polynucleotides include genomic DNA, cDNA and antisense DNA, and spliced or unspliced mRNA, rRNA tRNA and antisense RNA (e.g., RNAi, si RNA, miRNA). Polynucleotides include naturally occurring, synthetic, and intentionally altered or modified polynucleotides as well as analogues and derivatives. Alterations can result in increased stability due to resistance to nuclease digestion, for example. Polynucleotides can be double, single or triplex, linear or circular, and can be of any length.

Polynucleotides include sequences that are degenerate as a result of the genetic code. There are 20 natural amino acids, most of which are specified by more than one codon.

Polynucleotide sequences include sequences having 15-20, 20-30, 30-40, 40-50, 50-75, 75-100, 100-150, 150-200, or more contiguous nucleotides. In additional aspects, the polynucleotide sequence includes a sequence having 200 or more, 250 or more, 300 or more, 400 or more, 500 or more, up to the full length coding sequence.

Polynucleotide sequences include complementary sequences such as antisense. Such sequences may optionally be encoded by a nucleic acid and such a nucleic acid may be operatively linked to an expression control element for expression of the encoded antisense in cells or in vivo.

Polynucleotides can be obtained using various standard cloning and chemical synthesis techniques. Purity of polynucleotides can be determined through sequencing, gel electrophoresis and the like. For example, nucleic acids can be isolated using hybridization as set forth herein or computer-based database screening techniques known in the art. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

As disclosed herein, methods and uses include modulating an immune response. Methods and uses can be performed in vivo, such as in a subject, in vitro, ex vivo, in a cell, in solution, in solid phase or in silica. In one embodiment, a method or use includes contacting an agent, such as an agonist, or antagonist of a gene encoding a protein, or a protein set forth in Table 1 sufficient to modulate the immune response. In another embodiment, a method or use includes contacting an agent, such as an agonist, or antagonist of a gene encoding a protein, or a protein set forth in Table 1 sufficient to modulate Th* cell function or activity.

As used herein, the term "modulate," means an alteration or effect of the term modified. For example, the term modulate can be used in various contexts to refer to an alteration or effect of an activity, a function, or expression of a polypeptide, gene or signaling pathway, or a physiological condition or response of an organism. Methods and uses include modulating one or more functions, activities or expression of a gene encoding a protein, or a protein set forth in Table 1, in solid phase, in a cell, in vitro, ex vivo or in vivo. Methods and uses also include modulating one or more functions, activities or expression of a T cell response, activity or function, for example, a Th* response, activity, function or numbers/proliferation.

Where the term "modulate" is used to modify the term "protein" this means that the referenced protein activity, function, or expression is altered or affected (e.g., decreased, reduced, inhibited, suppressed, limited, controlled or prevented, etc.). Where the term "modulate" is used to modify the term "T cell" or "Th* cell" this means that the T cell or Th* cell response, activity, function, or numbers/proliferation is altered or affected (e.g., decreased, reduced, inhibited, suppressed, limited, controlled or prevented, etc.). Detecting an alteration or an effect on protein activity, function or expression, or alteration of the T cell or Th* cell response, activity, function, or numbers/proliferation can be determined as set forth herein using assays, such as cell based, in vitro or in vivo assays.

Modulators, such as agonists and antagonists affect activity or function of immune response, such as a T cell response, activity or function, for example, a Th* cell response, activity or function. Th* cells are charcterized by a particular gene expression pattern. As set forth in Example 2, Th* cells are CXCR3+, CCR6+, CCR4−, and are distinguished from Th1, Th17 and Th2 cells. Table 1 lists a detailed gene set modulated in LTB1 donors. Differential gene expression occurs when the expression level is at least 2-fold higher or lower than the median expression level in Th1, Th17 or Th2 cells. Accordingly, non-limiting representative examples include modulators of one or more genes whose differential expression characterizes Th* cells compared to other T cells, e.g., as shown in Table 1 by Th*>all (genes typically upregulated in Th*), and Th*<all (genes typically downregulated in Th*), as compared to median expression level in Th1, Th17 or Th2 cells.

Non-limiting examples of immune response modulators include agents that have agonist or antagonist activity. Non limiting examples include small molecules, such as small organic molecules having a molecular weight of less than about 1,000 Daltons (1 kDa), for example around 500 Daltons.

Additional non limiting examples of immune response modulators include antibodies and subsequences/fragments that retain at least partial binding activity. The term "antibody" refers to a protein that binds to another molecule (antigen) via heavy and light chain variable domains, denoted $V_H$ and $V_L$, respectively. An antibody typically includes a constant and/or variable (e.g., hypervariable, such as CDR or FR) region. Regions in the CDRs (CDR1, CDR2, and/or CDR3) are considered to confer antigen binding specificity and/or affinity. "Antibody" may refer to any polyclonal or monoclonal immunoglobulin molecule, or mixtures thereof, such as IgM, IgG, IgA, IgE, IgD. Antibodies belong to any antibody class or subclass. Exemplary subclasses for IgG are $IgG_1$, $IgG_2$, $IgG_3$ and $IgG_4$.

"Monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

Antibodies include kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa and two lambda light chains. The primary difference between kappa and lambda light chains is in the sequences of the constant region.

An antibody that includes or consists of a Heavy (H) chain and/or Light (L) chain or fragment of a Heavy (H) chain or Light (L) chain can include a single H or L chain or a single H or L chain fragment, or a plurality (2, 3, 4 or more) of Heavy (H) chains and/or Light (L) chains, or a plurality of fragments of Heavy (H) chains and/or Light (L) chains. A fusion polypeptide that includes a Heavy (H) chain and/or Light (L) chain of an antibody or fragment can but is not required to include 2 Heavy (H) chains and 2 Light (L) chains and therefore fusion polypeptides as set forth herein. An antibody or fragment thereof may be an oligomeric (higher order or valent) forms, such as a trimer, tetramer, pentamer, hexamer, heptamer, and so forth, with other antibodies, fragments thereof, Heavy (H) chain, Light (L) chain, or polypeptides distinct from an antibody Heavy (H) or Light (L) chain.

An "antibody" subsequence refers to a functional fragment or subsequence of an immunoglobulin. Non-limiting examples of antibody subsequences include an Fab, Fab', $F(ab')_2$, Fv, Fd, single-chain Fv (scFv), disulfide-linked Fvs (sdFv), $V_L$, $V_H$, diabody ($(V_L\text{-}V_H)_2$ or $(V_H\text{—}V_L)_2$), triabody (trivalent), tetrabody (tetravalent), minibody ($(scF_V\text{-}C_H3)_2$), IgGdeltaCH2, scFv-Fc or $(scFv)_2$-Fc fragment. In particular aspects, an Fab, Fab', $F(ab')_2$, Fv, Fd, single-chain Fv (scFv), disulfide-linked Fvs (sdFv), $V_L$, $V_H$, diabody ($(V_L\text{—}V_H)_2$ or $(V_H\text{—}V_L)_2$), triabody (trivalent), tetrabody (tetravalent), minibody ($(scF_V\text{-}C_H{}^3)_2$), IgGdeltaCH2, scFv-Fc or $(scFv)_2$-Fc subsequence.

Antibody subsequences, including single-chain antibodies, can include all or a portion of heavy or light chain variable region(s) (e.g., CDR1, CDR2 or CDR3) alone or in combination with all or a portion of one or more of the following: hinge region, CH1, CH2, and CH3 domains. Also included are antigen-binding subsequences of any combination of heavy or light chain variable region(s) (e.g., CDR1, CDR2 or CDR3) with a hinge region, CH1, CH2, and CH3 domains.

Antibodies include mammalian, human, humanized, and primatized sequences. The term "human," in reference to an antibody means that the amino acid sequence is fully human. A "human antibody" therefore refers to an antibody having human immunoglobulin amino acid sequences, i.e., human heavy and light chain variable and constant regions that specifically bind to target. That is, all of the antibody amino acids are human or can or do exist in a human antibody. Thus, for example, an antibody that is non-human may be made fully human by substituting the non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest,* 4$^{th}$ Ed. US Department of Health and Human Services. Public Health Service (1987); and Chothia and Leski *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991)). Human antibodies therefore include antibodies in which one or more amino acid residues have been substituted with one or more amino acids present in another human antibody.

The term "humanized" when used in reference to an antibody, means that the amino acid sequence of the antibody has non-human amino acid residues (e.g., mouse, rat, goat, rabbit, non-human primate, etc.) of one or more determining regions (CDRs) that specifically bind to a target in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human FRs can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or FR sequences. For example, a FR substitution at a particular position that is not found in a human antibody or the donor non-human antibody may be predicted to improve binding affinity or specificity human antibody at that position.

Antibodies referred to as "primatized" are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

Antibodies can be generated using techniques including conventional hybridoma technology using splenocytes isolated from immunized animals that respond to the antigen and fused with myeloma cells, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Monoclonal antibodies can also be obtained by direct cloning of immunoglobulin sequences from animals, including primate or human subjects. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int Rev. Immunol.* 13:65 (1995)).

Transgenic animals with one or more human immunoglobulin genes (kappa or lambda) that do not express endogenous immunoglobulins are described, for example in, U.S. Pat. No. 5,939,598. Such animals can therefore be used to produce human antibodies. A specific non-limiting example is the human transchromosomic KM Mice™ (Tomizuka et al., *Proc. Natl. Acad. Sci. USA* 97:722 (2000); and Ishida et al., *Cloning Stem Cells* 4:91 (2004)) which can produce human immunoglobulin genes (WO02/43478) or HAC mice (WO02/092812).

Antibody subsequences can also be produced by proteolytic hydrolysis. An antibody, for example, can be digested with pepsin or papain. Antibody fragments produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used.

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) can be used to humanize antibodies (Carter et al., *Proc. Natl. Acad. Sci. USA* 89:4285 (1992); and Presta et al., *Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Additional non limiting examples of immune response modulators include inhibitory nucleic acids (e.g., inhibitory RNA). Such inhibitory nucleic acids can be readily incorporated into various vectors for introduction into cells using conventional methods known to one of skill in the art.

Inhibitory nucleic acids can be a single-stranded sequence, or form a double- or triple-stranded sequence. In particular aspects, an inhibitory nucleic acid is a micro-RNA (miRNA), siRNA, shRNA, trans-splicing RNA, antisense RNA or triplex forming RNA.

Inhibitory, antisense, siRNA (small interfering RNA), miRNA (micro RNA), shRNA (small hairpin RNA), RNAi and antisense oligonucleotides can modulate expression of a target protein encoding gene (e.g., as set forth in Table 1), thereby modulating an immune response, such as a T cell (e.g., Th* cell) response, activity or function. Such molecules include those able to inhibit expression of a target gene involved in mediation of a disease process, thereby reducing, inhibiting or alleviating one or more symptoms of a disease.

Antisense includes single, double or triple stranded polynucleotides and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., *Cell* 95:1017 (1998); and Fire et al., *Nature,* 391:806 (1998)). Double stranded RNA sequences from a target gene coding region may therefore be used to inhibit or prevent gene expression/transcription in accordance with the methods and uses of the invention. Antisense and RNAi can be produced based upon nucleic acids encoding target protein (e.g., as set forth in Table 1). For example, a single or double stranded nucleic acid (e.g., RNA) can target protein encoding gene (e.g., as in Table 1).

A "siRNA" refers to a therapeutic molecule involved in the RNA interference process for a sequence-specific post-transcriptional gene silencing or gene knockdown. siRNAs have homology with the sequence of the cognate mRNA of the targeted gene. Small interfering RNAs (siRNAs) can be synthesized in vitro or generated by ribonuclease III cleavage from longer dsRNA and are the mediators of sequence-specific mRNA degradation. siRNA or other such nucleic acids of the invention can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions.

Specific siRNA constructs for inhibiting mRNA of a target gene may be between 15-50 nucleotides in length, and more typically about 20-30 nucleotides in length. Such nucleic acid molecules can be readily incorporated into various vectors for introduction into cells using conventional methods known to one of skill in the art. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

A "fusion" or "chimera," when used in reference to a sequence, means that the sequence contains one or more portions that are based upon, derived from, or obtained or isolated from, two or more different proteins or nucleic acids, i.e. are heterologous with respect to each other. That is, for example, a portion of the sequence may be based upon or from one particular protein or nucleic acid, and another portion of the sequence may be based upon or from a different protein or nucleic acid. Thus, a fusion or chimeric sequence is a molecule in which different portions of the sequence are of different origins.

Modulators, such as agonists and antagonists can be identified by assays disclosed herein or known in the art. For example, the amount of activity can be assessed directly, such as measuring the particular activity (e.g., inhibitor activity, binding affinity, avidity, selectivity (specificity) or non-selectivity). For example, a Th* cell agonist or antagonist can be identified by inhibition or stimulation of Th* cell response, activity, or function, such as reflected by changes in gene expression (e.g., Table 1), cytokine production or cell numbers/proliferation. An agonist or antagonist can also be identified by changes in cell expression of a marker.

The term "isolated," when used as a modifier of a composition (e.g., polypeptide, nucleic acid, etc.), means that the composition is made by the hand of man or are separated, completely or at least in part, from their naturally occurring in vivo environment. Generally, an isolated composition is substantially free of one or more materials with which they normally associate with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. Thus, "isolated" does not exclude forms (e.g., pharmaceutical formulations and combination compositions) in which there are combinations therein, any one of which is produced by the hand of man.

An "isolated" composition can also be "purified" when free of most or all of the materials with which it typically associates with in nature. Thus, an isolated polypeptide that also is substantially pure or purified does not include polypeptides or polynucleotides present among millions of other sequences, such as in a polypeptide library or nucleic acids in a genomic or cDNA library, for example. A "purified" composition can be combined with one or more other molecules.

The term "bind," or "binding," when used in reference to an interaction between two entities means that there is a physical interaction at the molecular level or functional interaction. A functional interaction need not require physical binding. An inhibitor of binding partially or completely inhibits, reduces or decreases a physical interaction or a functional interaction between the referenced entities. Binding inhibition can be due to steric hinderance, occupation or obstruction or blocking of the site of physical or functional interaction or alteration of a modification or another factor that participates in binding between the referenced entities. A stimulator of binding can enhance or increase a physical interaction or a functional interaction between the referenced entities, or reduce, inhibit or decrease dissociation between the referenced entities. An example of a functional interaction is where an intermediate facilitates or mediates a change in binding activity of one entity by another entity, such as a signaling pathway where molecules within the pathway functionally interact but need not physically contact each other.

As used herein, the term "contact" and grammatical variations thereof means a physical or functional interaction between one entity and one or more other entities. An example of physical contact is a direct or indirect binding, such as between an agonist or antagonist and a target gene or protein (e.g., as in Table 1). An example of a functional interaction is where an intermediate facilitates or mediates a change in activity of one entity by another entity, such as a signaling pathway where molecules within the pathway functionally interact but need not physically contact each other. In the methods and uses herein, contact can occur in solution, in solid phase, in vitro, ex vivo or in vivo (i.e., in a subject).

Responses, disorders and diseases also include, without limitation, immune responses, disorders and diseases, inflammatory responses, disorders and diseases, and inflammation. Responses, disorders and diseases also include, without limitation, autoimmune responses, disorders and diseases. Responses additionally include T cell (e.g., Th* cell) response, function, activity, proliferation, or differentiation.

Responses, disorders and diseases treatable in accordance with embodiments include, but are not limited to, treatment of acute and chronic undesirable or aberrant immune responses, disorders or diseases, inflammatory responses, disorders or diseases or inflammation. Responses, disorders and diseases treatable in accordance with embodiments herein also include, but are not limited to treatment of acute and chronic autoimmune responses, disorders and diseases. Such responses, disorders and diseases may be antibody or cell mediated, or a combination of antibody and cell mediated.

As used herein, an "undesirable immune response" or "aberrant immune response" refers to any immune response, activity or function that is greater or less than desired or physiologically normal response, activity or function including, acute or chronic responses, activities or functions. "Undesirable immune response" is generally characterized as an undesirable or aberrant increased or inappropriate response, activity or function of the immune system. However, an undesirable immune response, function or activity can be a normal response, function or activity. Thus, normal immune responses so long as they are undesirable, even if not considered aberrant, are included within the meaning of these terms. An undesirable immune response, function or activity can also be an abnormal response, function or activity. An abnormal (aberrant) immune response, function or activity deviates from normal.

Undesirable or aberrant immune responses, inflammatory responses, or inflammation are characterized by many different physiological adverse symptoms or complications, which can be humoral, cell-mediated or a combination thereof. Responses, disorders and diseases that can be treated in accordance with embodiments herein include, but are not limited to, those that either directly or indirectly lead to or cause cell or tissue/organ damage in a subject. At the whole body, regional or local level, an immune response, inflammatory response, or inflammation can be characterized by swelling, pain, headache, fever, nausea, skeletal joint stiffness or lack of mobility, rash, redness or other discoloration. At the cellular level, an immune response, inflammatory response, or inflammation can be characterized by one or more of T cell activation and/or differentiation, cell infiltration of the region, production of antibodies, production of cytokines, lymphokines, chemokines, interferons and interleukins, cell growth and maturation factors (e.g., proliferation and differentiation factors), cell accumulation or migration and cell, tissue or organ damage. Thus, methods and uses include treatment of and an ameliorative effect upon any such physiological symptoms or cellular or biological responses characteristic of immune responses, inflammatory response, or inflammation.

Autoimmune responses, disorders and diseases are generally characterized as an undesirable or aberrant response, activity or function of the immune system characterized by increased or undesirable humoral or cell-mediated immune responsiveness or memory, or decreased or insufficient tolerance to self-antigens. Autoimmune responses, disorders and diseases that may be treated in accordance with embodiments herein include but are not limited to responses, disorders and diseases that cause cell or tissue/organ damage in the subject. The terms "immune disorder" and "immune disease" mean an immune function or activity, which is characterized by different physiological symptoms or abnormalities, depending upon the disorder or disease.

In particular embodiments, a method or use according to embodiments herein decreases, reduces, inhibits, suppresses, limits or controls an undesirable or aberrant immune response, immune disorder, inflammatory response, or inflammation in a subject. In additional particular embodiments, a method or use decreases, reduces, inhibits, suppresses, limits or controls an autoimmune response, disorder or disease in a subject. In further particular embodiments, a method or use decreases, reduces, inhibits, suppresses, limits or controls an adverse symptom of the undesirable or aberrant immune response, immune disorder, inflammatory response, or inflammation, or an adverse symptom of the autoimmune response, disorder or disease.

As used herein, the term "associated with," when used in reference to the relationship between a symptom and a condition, disorder or disease, means that the symptom is caused by the referenced condition, disorder or disease, or is a secondary effect of the referenced condition, disorder or disease. A symptom that is present in a subject may therefore be the direct result of or caused by the referenced condition, or may be due at least in part to the subject reacting or responding to the referenced condition, disorder or disease, e.g., a secondary effect.

As used herein, the term "subject" includes animals, typically mammalian animals, such as but not limited to humans (newborns, infants, toddlers, children, adults), non-human primates (apes, gibbons, chimpanzees, orangutans, macaques), domestic animals (dogs and cats), farm animals (horses, cows, goats, sheep, pigs), and experimental animals (mouse, rat, rabbit, guinea pig). Subjects include animal disease models. Subjects include naturally occurring or non-naturally occurring mutated or non-human genetically engineered (e.g., transgenic or knockout) animals. Subjects further include animals having or at risk of having a chronic or acute condition, disorder or disease.

Particular non-limiting examples of subjects include subjects having or at risk of having immune disorders and diseases as set forth herein. Such at risk subjects can be identified by a personal or family history, through genetic screening, tests appropriate for detection of increased risk, or exhibiting relevant symptoms indicating predisposition or susceptibility.

Methods of the invention include subjects contacted with or administered a modulator, such as agonist or antagonist prophylactically, e.g., prior to a sign or manifestation of an undesirable or aberrant immune response, disorder or disease, an inflammatory response, disorder or disease, inflammation or an autoimmune response, disorder or disease, or a symptom thereof.

In the methods of the invention in which a detectable result or beneficial effect is a desired outcome, such as a therapeutic benefit in a subject treated in accordance with the invention, compositions can be administered in sufficient or effective amounts. An "amount sufficient" or "amount effective" includes an amount that, in a given subject, can have a desired outcome or effect. The "amount sufficient" or "amount effective" can be an amount that provides, in single or multiple doses, alone or in combination with one or more other (second) compounds or agents (e.g., a drug), treatments or therapeutic regimens, a long or short term detectable response, a desired outcome or beneficial effect in a particular given subject of any measurable or detectable degree or duration (e.g., for minutes, hours, days, months, years, or cured).

An amount sufficient or an amount effective can but need not be provided in a single administration and can but need not be administered alone (i.e., without a second drug, agent, treatment or therapeutic regimen), or in combination with another compound, agent, treatment or therapeutic regimen. In addition, an amount sufficient or an amount effective need not be sufficient or effective if given in single or multiple doses without a second compound, agent, treatment or therapeutic regimen, since additional doses, amounts or duration above and beyond such doses, or additional drugs, agents, treatment or therapeutic regimens may be included in order to be effective or sufficient in a given subject. Further, an amount sufficient or an amount effective need not be effective in each and every subject, nor a majority of subjects in a given group or population. Thus, as some subjects may not benefit from such treatments an amount sufficient or an amount effective means sufficiency or effectiveness in a particular subject, not a group or the general population. As is typical for such methods, some subjects will exhibit a greater or less response to a method of the invention, including treatment/therapy.

Reducing, inhibiting decreasing, eliminating, delaying, halting or preventing a progression or worsening or an adverse symptom of the condition, disorder or disease is a satisfactory outcome. The dose amount, frequency or duration may be proportionally increased or reduced, as indicated by the status of the condition, disorder or disease being treated, or any adverse side effects of the treatment or therapy. Dose amounts, frequencies or duration also considered sufficient and effective are those that result in a reduction of the use of another drug, agent, treatment or therapeutic regimen or protocol. For example, there is a beneficial or therapeutic effect if contact, administration or delivery in vivo results in the use of a reduced amount, frequency or duration of another drug, agent, treatment or therapeutic regimen or protocol to treat the condition, disorder or disease, or an adverse symptom thereof.

An "amount sufficient" or "amount effective" includes reducing, preventing, delaying or inhibiting onset, reducing, inhibiting, delaying, preventing or halting the progression or worsening of, reducing, relieving, alleviating the severity, frequency, duration, susceptibility or probability of one or more adverse or undesirable symptoms associated with the condition, disorder or disease of the subject. In addition, hastening a subject's recovery from one or more adverse or undesirable symptoms associated with the condition, disorder or disease is considered to be an amount sufficient or effective. Various beneficial effects and indicia of therapeutic benefit are as set forth herein and are known to the skilled artisan.

An "amount sufficient" or "amount effective," in the appropriate context, can refer to therapeutic or prophylactic amounts. Therapeutically or prophylactically sufficient or effective amounts mean an amount that, in a given subject, detectably improves the condition, disorder or disease, such as an inflammatory condition, disorder or disease, as assessed by one or more objective or subjective clinical endpoints appropriate for the condition, disorder or disease. Sufficiency or effectiveness of a particular treatment can be ascertained by various clinical indicia and endpoints.

The terms "treat," "therapy" and grammatical variations thereof when used in reference to a method means the method provides an objective or subjective (perceived) improvement in a subjects' condition, disorder or disease, or an adverse symptom associated with the condition, disorder or disease. Non-limiting examples of an improvement can therefore reduce or decrease the probability, susceptibility or likelihood that the subject so treated will manifest one or more symptoms of the condition, disorder or disease.

Methods and uses of the invention therefore include providing a detectable or measurable beneficial effect or therapeutic benefit to a subject, or any objective or subjective transient or temporary, or longer-term improvement (e.g., cure) in the condition. Thus, a satisfactory clinical endpoint is achieved when there is an incremental improvement in the subjects condition or a partial reduction in the severity, frequency, duration or progression of one or more associated adverse symptoms or complications or inhibition, reduction, elimination, prevention or reversal of one or more of the physiological, biochemical or cellular manifestations or characteristics of the condition, disorder or disease. A therapeutic benefit or improvement ("ameliorate" is used synonymously) therefore need not be complete ablation of any or all adverse symptoms or complications associated with the condition, disorder or disease but is any measurable or detectable objectively or subjectively meaningful improvement in the condition, disorder or disease. For example, inhibiting a worsening or progression of the condition, disorder or disease, or an associated symptom (e.g., slowing or stabilizing one or more symptoms, complications or physiological or psychological effects or responses), even if only for a few days, weeks or months, even if complete ablation of the condition, disorder or disease, or an associated adverse symptom is not achieved is considered to be beneficial effect.

Prophylactic methods are included. "Prophylaxis" and grammatical variations thereof mean a method in accordance with the invention in which contact, administration or in vivo delivery to a subject is prior to manifestation or onset of a condition, disorder or disease (or an associated symptom or physiological or psychological response), such that it can eliminate, prevent, inhibit, decrease or reduce the probability, susceptibility, onset or frequency of having a condition, disorder or disease, or an associated symptom. Target subject's for prophylaxis can be one of increased risk (probability or susceptibility) of contracting the condition, disorder or disease, or an associated symptom, or recurrence of a previously diagnosed condition, disorder or disease, or an associated symptom, as set forth herein.

Any compound or agent (e.g., drug), therapy or treatment having a beneficial, additive, synergistic or complementary activity or effect (beneficial or therapeutic) can be used in combination with a binding agent in accordance with the invention. A "second compound" or "second agent" refers to any compound or agent (e.g., drug) that is not the first compound or agent of the recited composition.

Pharmaceutical compositions can be formulated to be compatible with a particular route of administration. Compositions for parenteral, intradermal, or subcutaneous administration can include a sterile diluent, such as water, saline, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin, can prolong absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, creams or patches.

Additional pharmaceutical formulations and delivery systems are known in the art and are applicable in the methods disclosed herein (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

The compositions, methods and uses in accordance with embodiments herein, including polypeptide sequences, subsequences, variants and derivatives, polymorphisms, treatments, therapies, combinations, agents, drugs and pharmaceutical formulations can be packaged in dosage unit form for ease of administration and uniformity of dosage. "Dosage unit form" as used herein refers to physically discrete units suited as unitary dosages treatment; each unit contains a quantity of the composition in association with the carrier, excipient, diluent, or vehicle calculated to produce the desired treatment or therapeutic (e.g., beneficial) effect. The unit dosage forms will depend on a variety of factors including, but not necessarily limited to, the particular composition employed, the effect to be achieved, and the pharmacodynamics and pharmacogenomics of the subject to be treated.

In some embodiments, there are provided kits including polypeptide sequences, subsequences, variants and derivatives, polymorphisms, combination compositions and pharmaceutical formulations thereof, packaged into suitable packaging material. Kits can be used in various in vitro, ex vivo and in vivo methods and uses, for example a treatment method or use as disclosed herein.

A kit typically includes a label or packaging insert including a description of the components or instructions for use in vitro, in vivo, or ex vivo, of the components therein. A kit can contain a collection of such components, e.g., a polypeptide sequence, alone, or in combination with another therapeutically useful composition (e.g., an immune modulatory drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods and uses, treatment protocols or therapeutic regimes set forth herein. Exemplary instructions include, instructions for treating an undesirable or aberrant immune response, disorder or disease, an inflammatory response, disorder or disease, inflammation, an autoimmune response, disorder or disease. Kits therefore can additionally include labels or instructions for practicing any of the methods and uses described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Kits can additionally include other components. Each component of the kit can be enclosed within an individual container and all of the various containers can be within a single package. Kits can be designed for cold storage. Kits can further be designed to contain polypeptide sequences, subsequences, variants and derivatives, polymorphisms, or combination compositions or pharmaceutical compositions.

Embodiments herein provide cell-free (e.g., in solution, in solid phase) and cell-based (e.g., in vitro or in vivo) methods of screening for, detecting and identifying agents that modulate an immune response, such as an undesirable or aberrant immune response, disorder or disease, an inflammatory response, disorder or disease, inflammation or an autoimmune response, disorder or disease. Embodiments herein also provide cell-free (e.g., in solution, in solid phase) and cell-based (e.g., in vitro or in vivo) methods of screening, detecting and identifying MTB or NTM infection, as well as agents for treatment/vaccination of MTB or NTM infection. The methods can be performed in solution, in solid phase, in silica, in vitro, in a cell, and in vivo.

In various embodiments, a method of screening for an agent includes contacting a candidate agent; and determining if the test agent modulates an immune response, e.g., Th* function, activity or numbers/proliferation. In another embodiment, a method of identifying an agent includes contacting a biological sample comprising T cells with a test agent and determining if the test agent modulates T cell, e.g., Th* cell function, activity or numbers/proliferation. A modulation of an immune response, T cell function, activity or numbers/proliferation, e.g., Th* cell function, activity or numbers/proliferation, identifies the test agent as such an agent.

In a further embodiment, a method of detecting a *M. tuberculosis* (MTB) or non-tuberculosis *mycobacterium* infection in a subject is provided. In one aspect, a method includes contacting a biological sample (e.g., PBMC) from the subject with a protein or peptide as set forth herein (e.g., in any of Tables 2-4), and measuring the cytokine response of the cells (e.g., T cells, such as Th* cells). The presence of a cytokine response detects the infection in the subject.

The terms "determining," "assaying" and "measuring" and grammatical variations thereof are used interchangeably herein and refer to either qualitative or quantitative determinations, assays, measurements or both qualitative and quantitative determinations. When the terms are used in reference to measurement or detection, any means of assessing the relative amount, including the various methods set forth herein and known in the art.

Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a protein" or "agent," "agonist" or "antagonist" includes a plurality of such proteins, subsequences, variants and derivatives, polymorphisms, agents, agonists, anatagonists, or combination compositions or pharmaceutical compositions, and reference to a "T cell" or a "Th* cell" response, activity or function can include reference to one or more T cell responses, activities or functions, and so forth.

As used herein, numerical values are often presented in a range format throughout this document. The use of a range format is merely for convenience and brevity and should not be construed as an inflexible limitation on the scope of the embodiments herein. Accordingly, the use of a range expressly includes all possible subranges, all individual numerical values within that range. Furthermore, all numerical values or numerical ranges include integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a ranges, such as 1-2, 5-10, 10-50, 50-100, 100-500, 100-1000, 500-1000, 1000-2000, 1000-5000, etc.

A series of range formats are used throughout this document. The use of a series of ranges includes combinations of the upper and lower ranges to provide a range. This construction applies regardless of the breadth of the range and in all contexts throughout this patent document. Thus, for example, reference to a series of ranges such as 5 to 10, 10 to 20, 20 to 30, 30, to 50, 50 to 100, 100 to 150, 150 to 200, 200 to 300, or 300 to 400, 400-500, 500-600, or 600-705, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-200, 50 to 200, 50 to 300, 50, to 400, 50 to 500, 100 to 300, 100 to 400, 100 to 500, 100 to 600, 200-400, 200-500, 200 to 600, 200 to 700, and so forth.

Embodiments herein are generally disclosed herein using affirmative language to describe the numerous embodiments. Embodiments herein also specifically include those in which particular subject matter is excluded, in full or in part, such as substances or materials, method steps and conditions, protocols, procedures, assays or analysis. Thus, even though embodiments herein are generally not expressed herein in terms of what they do not include aspects that are not expressly included in various embodiments are nevertheless disclosed herein.

A number of embodiments have been described. Nevertheless, it will be understood that various modifications may be made without departing from the spirit and scope of the embodiments. Accordingly, the following examples are intended to illustrate but not limit the scope of the embodiments described in the claims.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1: Definition and Phenotyping of a Specific T Cell Subset which Maintains Latent TB Infection (LTBI)

Latent tuberculosis infection (LTBI) is characterized by an often life-long containment of mycobacteria to granuloma in the lung that is mediated at least in part by IFNγ producing CD4+ T cells. The studies described in this example below highlight both methods to define, and the phenotype of, a subset of T cells that play a protective role in the maintenance of a latent status of TB infection. These studies identify a number of specific molecules including cell surface markers, chemokine receptors and molecular pathways, which alone or in combination, are up- and down-regulated in TB infection. These molecules may be targeted by various means (i.e. antibodies and/or small-molecules) to cure TB infection or minimally dampen inflammation associated with active TB infection or the cavitation phase of the disease. In addition, these molecules or pathways may also be targeted in diseases associated with inappropriate inflammation such as in autoimmune disorders like Rheumatoid Arthritis (RA).

Example 2: MTB-Epitope-Specific Memory T Cells are Predominantly Th* (CXCR3+CCR6+CCR4−)

A genome-wide screen for epitopes of TB-specific memory CD4+ T cells was performed. Phenotypic characterization of the responding cells showed that they were remarkably homogenous with more than 90% displaying a CCR4−CXCR3+CCR6+ phenotype (called Th* cells in the following).

MTB-specific memory T cells are predominantly CXCR3+CCR6+ using the T cell library method and MTB lysate and peptide pools. To measure the frequency and distribution of T cells specific for individual TB epitopes a CFP1052-66-DRB5*01:01 tetramer (CFP1052-66; QAAVVRFQEAANKQK) was used. Epitope-specific CD4+ memory T cell responses, based on CD45RA and CCR7 expression, were detected in 5 LTBI donors at frequencies 0.022 to 0.519% (median of 0.09, interquartile range 0.03-0.33). No epitope-specific cells were detected in the CD4+ naïve subset or in the CD4+ memory subset from MTB uninfected non-BCG vaccinated control donors (healthy controls, HC).

Next the frequency of epitope-specific CXCR3+CCR6+CCR4− (Th*), CXCR3+CCR6−CCR4− (Th1), CXCR3−CCR6+CCR4− (Th17), and CXCR3−CCR6−CCR4+ (Th2) cells was investigated. The epitope-specific CD4+ memory T cells predominantly consisted of Th* cells, median 92%, interquartile range 84-99% of tetramer+ cells. Only a minor fraction appeared to be CXCR3+CCR6−CCR4− (Th1, 0.5%, 0-5.6%), CXCR3−CCR6+CCR4− (Th17, 1.2%, 0.7-11%), or CXCR3−CCR6−CCR4+ (Th2, 0.3%, 0-2.3%) cells (FIG. 1A, B).

To examine the cytokine production profile of these cells, CD4+ T cells were stimulated with TB-specific peptides. These peptides were chosen based on reactivity in selected donors—all donors used were included in the previously described genome-wide epitope screen. FIGS. 1C and D shows that the responding CXCR3+CCR6+CCR4− (Th*) cells are multifunctional and produce IFNγ, TNFα, and IL-2 but not IL-17A (FIGS. 1C and D). The majority of Th* cells were IFNγ+TNFα+IL-2+(median 38% of cytokine producing cells), IFNγ+TNFα+(25%), TNFα+(18%), followed by TNFα+IL-2+(12%) and IFNγ+(3%) (FIG. 1D).

Example 3: Th* Memory T Cells are Increased in Subjects with LTBI

Figure 2:
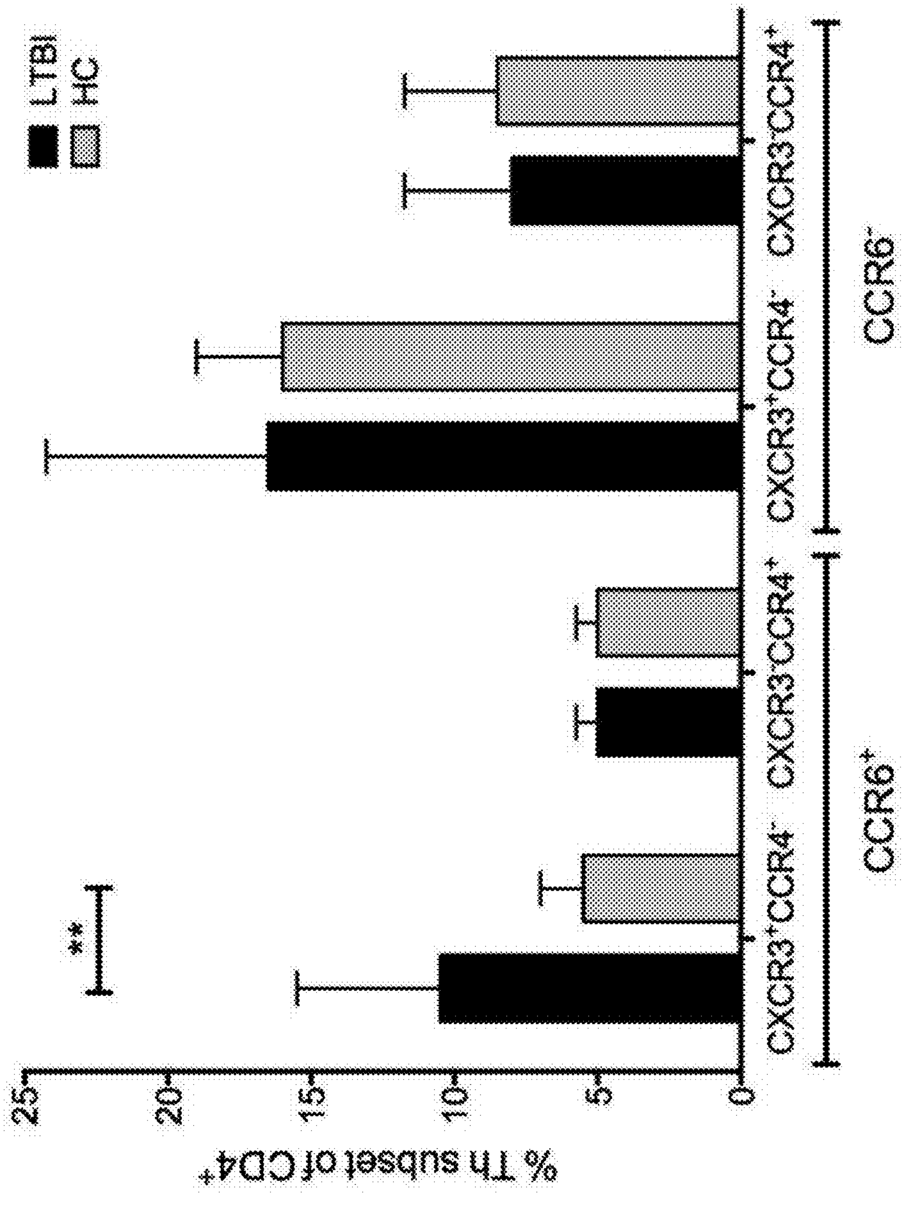
FIG. 2. The CXCR3, CCR6, CCR4− subset is increased in LTBI patients compared to non-TB individuals.

As MTB-specific memory T cells predominantly fall into the Th* population, this cell population could be increased in subjects with LTBI compared to healthy controls (HC). To address this the frequency of CXCR3+CCR6+CCR4− (Th*), CXCR3+CCR6−CCR4− (Th1), CXCR3−CCR6+ CCR4− (Th17), and CXCR3−CCR6−CCR4+ (Th2) cells in LTBI and HC donors were compared. As shown in FIG. 2, Th* cells were significantly (p=0.003) increased in LTBI donors with a median of 10.5% (8-15.5% interquartile range) compared to HC (median of 5.5%, (3.5-7%)). All other T cell subsets were seen with similar frequencies in the two cohorts; Th1; 16.5%, (13.3-24.3%, LTBI) and 16%, (8.8-19%, HC), Th2; 8%, (6-11.8%, LTBI) and 8.5%, (6-11.8%, HC), and Th17; 5%, (3.3-5.8%, LTBI) and 5%, (2.3-5.8%, HC) (FIG. 2).

Figure 3:
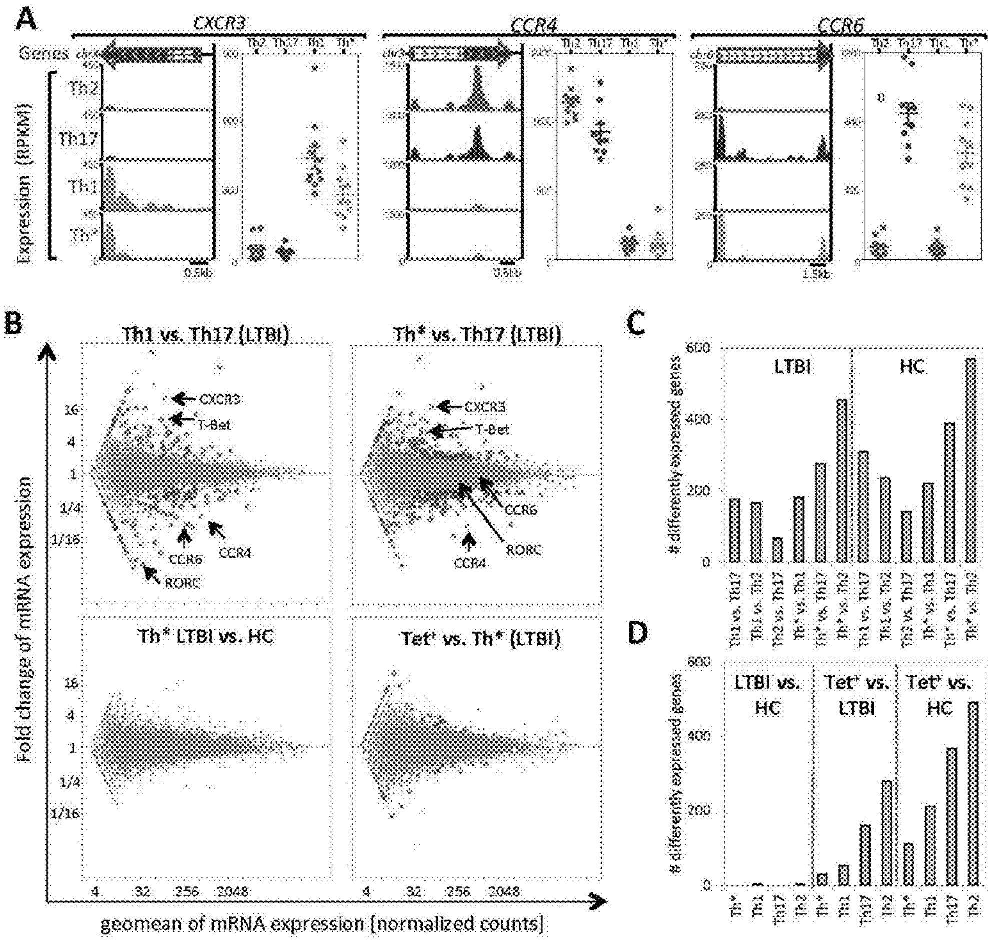
FIG. 3. The transcriptional program of TB-specific cells are conserved in the Th* compartment. (A) Mapping of short mRNA reads to CXCR3, CCR4 and CCR6 in Th2 (red), Th1 (green), Th17 (purple) and Th* (orange) cells.

Example 4: The Transcriptional Program of TB-Specific Memory T Cells is Found Conserved in the Th* Compartment of LTBI and HC Donors The transcriptional program in TB-specific memory T cells identified using tetramer staining were determined, and compared to the broader Th* subset, as well as conventional Th1, Th2 and Th17 cells using RNA-Seq. Mapping of short mRNA reads to the genome showed that transcripts of the phenotypic markers used for sorting (CXCR3, CCR6 and CCR4) were detectable and differences in expression magnitude were consistent with the sorting strategy (FIG. 3A). Gene expression values were quantile normalized and pairwise comparisons performed between groups of samples from 4-5 donors each using DESEQ. A gene was considered as differently expressed if the adjusted p-value was smaller than 0.05 and the change in magnitude of expression was at least two-fold. Significant differences of expression were detected for all sorting markers between the different cell types (FIG. 3B). Beyond the sorting markers, the expected behavior was observed for two key transcription factors, T-bet and RORgC, which are characteristic for Th1 and Th17 cells, respectively, but have both been shown to be expressed in Th* cells (FIG. 3B). This confirms that the sorting strategy and RNA profiling analysis could reliably detect differences in the mRNA transcription of different cell types.

Next, the divergence of the transcriptional profiles of different cell types and donor groups was quantified. A total of 177 genes met the conservative cutoffs for differential expression when comparing Th1 vs. Th17 cells in LTBI donors (red dots in FIG. 3B). A similar number of differences was found when comparing Th* cells to Th1, Th17 or Th2 cells in LTBI donors namely 181, 267 and 455, respectively (FIG. 3C). The same held true within HC donors (FIG. 3C). Thus, there are comparable or more differences in the transcriptional program of Th* cells compared to any conventional subset as there are between Th1 and Th17 cells. In contrast, when comparing gene expression in Th*, Th1, Th17 and Th2 cells between LTBI and HC donors, very few differences were detected, namely 0, 2, 0 and 2, respectively (FIG. 3D). Finally, when comparing gene expression in Tet+ cells to the different T cell subsets, the fewest number of differences were detected in Th* cells followed by Th1, Th17 and Th2 cells in either LTBI and HC donors (FIG. 3D). Overall it was concluded that Th* cells have a characteristic transcriptional program that distinguishes them from Th1, Th17 and Th2 cells, that these characteristics are conserved between LTBI and HC donors, and that TB-specific CD4+ T cells obtained by tetramer sorting in the absence of selection based on surface markers closely resemble Th* cells. Table 1 provides a detailed list of all genes that are modulated in this subset associated LTBI donors.

To further support this finding, the expression patterns of genes that distinguish Th*, Th1, Th17, Th2 and Tet+ cells were examined. A total of 1,670 genes were differentially expressed in the comparisons made between different cell types and donor groups shown in FIGS. 3C and D. FIG. 4A shows a heatmap of the expression level of these genes in the different individual samples. When grouping samples based on the similarity of their gene expression pattern by unsupervised clustering, samples from the same cell type fell together in separate clusters for Th1, Th2 and Th17 cells, and samples from donors with different disease states were intermixed within those clusters. Samples from Th* and Tet+ cells grouped together in one cluster, but there was a tendency of samples from LTBI donors and HC donors to separate within this cluster and for the Tet+ samples to be more similar to samples from LTBI donors. Given that the same donors were the source of Tet+ and Th* LTBI samples, caution has to be applied when interpreting the increased similarity of TB-specific Tet+ cells with Th* cells in TB infected individuals. Still, given the significant expansion of the Th* population in LTBI donors, it is possible that Tet+ cells constitute a specialized subset of cells within the Th* compartment that have a differential expression pattern for a subset of genes.

Example 5: Th* Cells Display Hallmarks of Both Th1 and Th17 Transcriptional Programs A total of 357 genes were differentially expressed in Th1 vs. Th17 cells when comparing groups of either HC or LTBI donors. When examining the expression pattern of these genes in Th* cells, most showed a polarization similar to Th1 cells (172 genes, 48%), a sizeable fraction showed an intermediate expression level (128 genes, 36%), and comparably few genes displayed a pattern similar to Th17 cells (57 genes, 16%). Notably, hallmark transcription factors TBX21 (T-Bet) and EOMES of Th1 cells were upregulated in both Th* and Th1 cells compared to Th17 cells, as well as IL33 receptor (IL1RL1), several cytotoxic factors such as granzymes (GZMA, GZMK) and perforin (PRF1). Yet, granzyme M (GZMM) was exclusively upregulated in Th1 cells. Conversely, the hallmark Th17 transcription factor RORgC was upregulated in both Th* and Th17 cells compared to Th1 cells along with other key genes such as ADAM12, PTPN13 and IL17RE, the receptor for IL17C. IL17RB (the receptor for IL17B and E) however, was exclusively upregulated in Th17 cells. Overall, this confirms that Th* cells show hallmarks of both Th1 and Th17 expression and that within the signature genes differentiating Th1 cells from Th17 cells, the expression pattern more closely resembles that of Th1 cells.

Example 6: Th* Cells have a Unique Transcriptional Program Including Genes Associated with TB Susceptibility and Enhanced T Cell Persistence Previously published analyses of the transcriptional program of Th* cells have focused on candidate genes of interest most of which were known to play a role in T cell development, such as RORgC and T-Bet. A global analysis was conducted to identify genes that are expressed differentially in Th* cells compared to the conventional memory helper T cells: Th1, Th17 and Th2 cells. A gene was considered to be differentially expressed in Th* cells if its median expression level was consistently at least 2-fold higher (or lower) than its median expression level in either Th1, Th17 or Th2 cells. Given that some differential expression patterns were detected between Th* cells from LTBI and HC donors, the genes were included in this list if they met these criteria in either set of donors. A total of 412 genes met this criteria with 203 increased and 209 decreased in Th* set compared to the other T cell subsets (FIG. 4). Pathway analysis of these genes shows enrichment of Cytokine:Receptor interactions (CCR2, IL12RB2, IL23R, CD117 (KIT), TNFSF13B). Importantly, mutations in both CCR2 and the IL12 receptor are known to cause increased susceptibility to TB. This supports that this T cells expression signature likely to be important for control of TB infection.

The list of genes that were downregulated in Th* cells includes TIGIT, a surface protein that has T-cell intrinsic regulatory inhibitory function. Loss of this function is associated with increased T cell persistence and immunoreactivity. As shown in FIG. 5, there is clearly reduced expression of TIGIT in Th* cells and Tet+ cells. As TIGIT forms a signaling axis with CD226, which enhances cytotoxic activity, the inventors examined how CD226 expression varied in these cell types. CD226 did not reach the cutoff for inclusion into the list of differentially expressed genes but upon plotting its level of expression along with TIGIT in the different cell types, within the Th* cells, there is an inverse pattern indicating that the most immune activated state (CD226 high, TIGIT low) is in the Tet+ cells, followed by Th* cells in LTBI donors, HC donors (FIG. 5). So the lower amount of TIGIT expressed in Th* cells in HC donors might partially be compensated by the concomitant reduction in CD226 expression.

Example 7: Th* Cells Produce a Broad Spectrum of Cytokines Upon Activation

Figure 1:
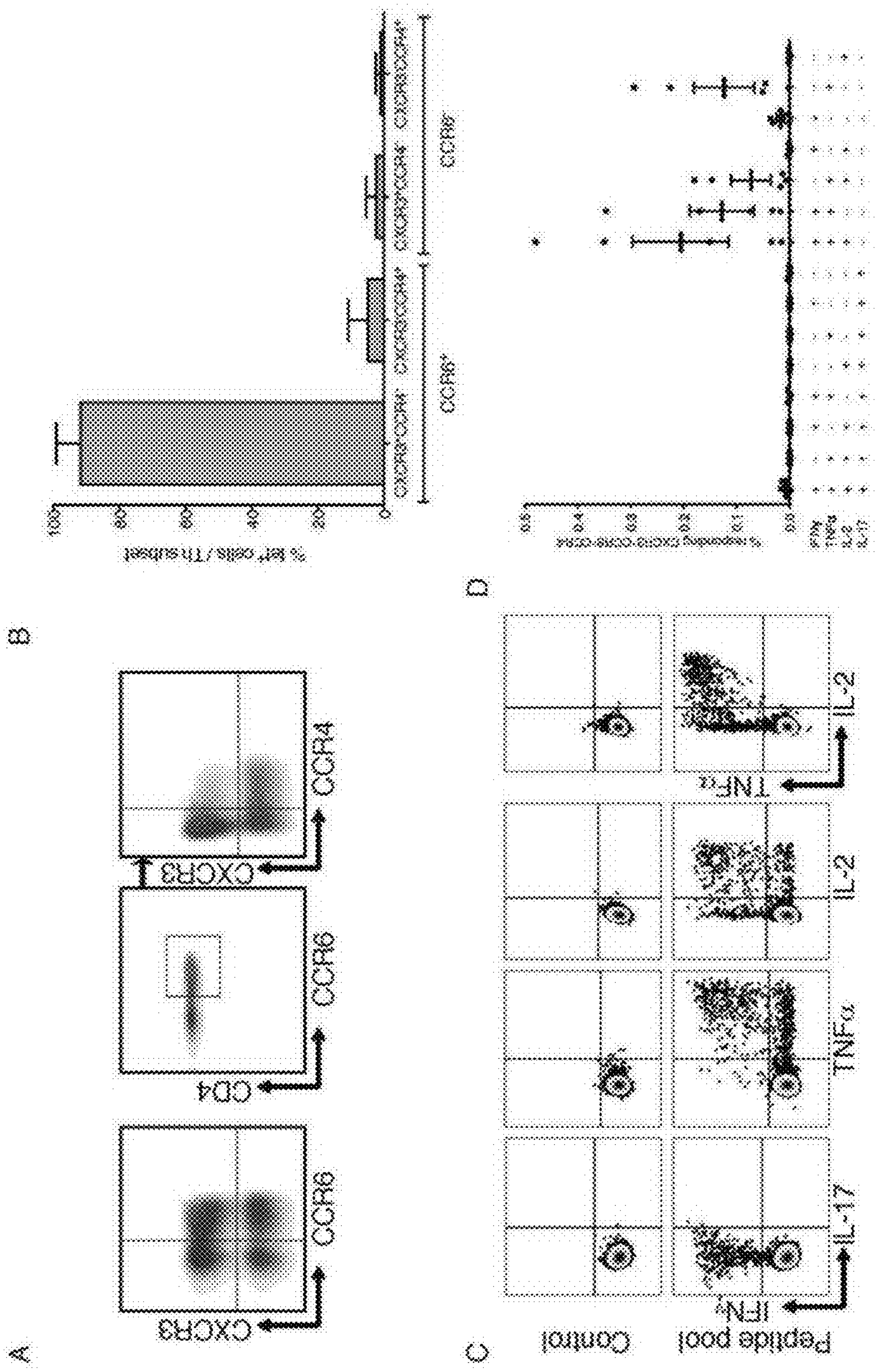
FIG. 1. Tet+ memory CD4 T cell responses to MTB are restricted to the CXCR3+, CCR6+, CCR4− T cell subset.

As shown in FIG. 1, upon stimulation with T cell epitopes from MTB, Th* cells from LTBI donors produced IFNγ, TNFα and IL-2. To more broadly examine the functional profile of these cells, Th* cells from three LTBI donors were stimulated with PMA/ionomycin (PI) and compared their transcriptional profile to resting Th* cells. The change of expression was specifically examined for a panel of 52 cytokines including those produced by human T cells in an epitope specific manner.

FIG. 6 shows all cytokines in the panel that showed a greater than 3-fold induction of expression after PI stimulation. As expected, the production of IFNγ, TNF and IL2 could reliably be detected also at the transcript level. In addition a large number of cytokines were produced upon stimulation by Th* cells namely CSF1/2, CCL3/4, GZMB, IL6/17a/22, CXCL9 and VEGFA. The large error bars for IL17A, CSF2 and IL6 were a result of these cytokines being absent in one donor sample, putting into question how robustly they are induced or if this donor represented an outlier. As for the robustly induced cytokines, interestingly, mutations in the CCL4 and IL22 loci have been associated with increased susceptibility to TB. Overall, these data reinforce that Th* cells are capable of producing a broad spectrum of cytokines that contribute to their ability to contain LTBI.

Example 8: Protein Expression Pattern of Th* Signature Genes

Next, it was determined if the unique transcriptional profile of Th* cells was reflected by a similar expression profile of proteins. CD4+ cells from HC and LTBI donors were stained for CCR2 and CD117. There was a significant higher level of expression of both markers in memory (CCR2 median 28.8% (interquartile range 25.4-33.7%), CD117 2.1% (0.5-2.2%)), vs. naïve (CCR2 0.2% (0.1-0.2%), CD117 0.01% (0.00-0.01%)) cells. The same was observed in CCR6+(CCR2 49.8% (32.1-54.1%), CD117 5.8% (2.3-6.2%)) vs. CCR6−(CCR2 17.0% (11.6-20.9%), CD117 0.5% (0.1-1.0%)) (FIG. 7A). Remarkably, it was found that there was a significant increased average level of expression in the CXCR3+CCR6+CCR4− cells (CCR2 58.4% (47.2-63.0%), CD117 7.1% (2.8-9.5%)) compared to the well characterized T cell subsets Th1 (CCR2 27.2% (26.2-31.9%), CD117 1.0% (0.2-2.1%)), Th17 (CCR2 31.7% (26.3-35.7%), CD117 2.0%(0.5-4.0%)) and Th2 (CCR2 14.2%(12.9-20.7%), CD117 0.6% (0.05-1.9%)), as was predicted from the transcriptional profile (FIG. 7A). No donor-specific pattern of expression was observed.

Next the expression of CCR2 and CD117 was investigated in TB-specific cells using the DRB5*01:01 CFP10 tetramer (FIG. 7B). Interestingly, the majority of TB-epitope-specific cells expressed CCR2 (92.0% (76.5-94.7%)), but was negative for CD117 (94.9% (92.5-98.0%)) (FIG. 7C). The inclusion of CCR2+ cells in addition to CXCR3+CCR6+CCR4− results in around 45% (34-48%) increase of tetramer+ and thus TB-specific cells (FIG. 7D). The exclusion of CD117 only had a minor effect, 2.3% (1.7-5.1%) increase and in combination with CCR2+ resulted in 48% (39-49%) increase. Thus, the transcriptional profiling defined additional markers expressed by the CXCR3+CCR6+CCR4− T cell subset and proved that this subset is a heterogeneous population that can be divided further.

Example 9: Conclusions

CD4+ memory T cell subsets are defined by the coordinate expression of select cytokines, chemokine receptors and transcription factors. The well characterized subsets Th1, Th2 and Th17 can be distinguished by their expression of CXCR3, CCR6 and CCR4. Using these chemokine receptors as markers a subset of cells that express CXCR3 and CCR6 but not CCR4 have been characterized. These cells have been shown to express the hallmark transcription factors of both Th1 and Th17 cells namely T-Bet and RORC, and have consequently been referred to as Th1*/Th17.1 or Th1/17 cells. However, in-depth analysis of the transcriptional signature of these cells suggests that they have a characteristic program that sets them apart from both Th1 and Th17 cells, and therefore designated these cells as Th*.

TB-specific T cells in LTBI donors fall nearly exclusively into the Th* subset. Th* cells are remarkable in that they can easily be detected directly ex vivo due to their ability to mount a strong multifunctional response to their cognate antigens. Multiple lines of evidence suggest that TB-specific memory cells are necessary for the often lifelong containment of MTB pathogens in latent TB infection. It was found that the number of cells in the Th* subset is greatly increased in LTBI (and by definition asymptomatic) donors. Furthermore, transcriptional analysis revealed that Th* cells preferentially express CCR2 and IL12 receptor and upon activation produce large amounts of CCL4 and IL-22, all of which have been implicated in higher susceptibility to TB infection. Understanding the characteristics of Th* cells that provide them with the ability to contain TB infection should in turn provide better correlates of efficacy for MTB vaccine development which are currently lacking.

Previous reports on Th* cells (or cells sorted on some but not all of the Th* markers CXCR3+, CCR6+ and CCR4−) have shown that such cells can produce IL17 upon in vitro expansion. However, there was no detection of IL-17 production of TB-specific Th* cells upon ex vivo antigen-specific stimulation. The lack of ability to detect TB-specific IL-17 producing Th* cells is in agreement with a previous study, in which Th* cells stimulated with TB protein extract (PPD) for five days did not produce IL-17, while Th* cells stimulated with *Candida* extract under identical conditions did. This suggests that a subset of Th* cells is responsible for IL-17 production, and the ability to detect IL-17 expression in bulk Th* cells from LTBI donors after PI stimulation is in agreement with this conclusion. Given that Th* cells showed a slight separation in the clustered gene expression profile between HC and LTBI donors supports that there might be a detectable difference in markers between Th* cells that do and those that do not produce IL-17, the latter being presumably enriched in LTBI donors. However, while there may be some differences between Th* cells in HC and LTBI donors, there are many more commonalities especially in comparison to conventional Th1, Th2 and Th17 cells, suggesting that there is an overarching shared transcriptional program in Th* cells.

Within the shared transcriptional program of Th* cells that distinguish them from other memory subsets, several genes were indicative of Th* cells showing increased immune-activation and persistence after prolonged stimulation. Th* cells express significantly higher levels of CCR2 and the TB-specific cells are almost exclusively CCR2 positive. CCR2 has been described as a marker of terminally differentiated T cells that is the result of multiple antigen encounters, which in the case of TB-specific cells is likely the outcome of chronic stimulation in LTBI donors. Th* cells selectively express MDR1 (ABCB1), which is associated with survival and longevity of cells. Furthermore, Th* cells lack expression of TIGIT which has been shown to result in hyperproliferative T cell responses. Finally, CD117 is expressed significantly higher on the Th* as compared to all other T cell subsets, and is associated with enhanced cell survival as is the transcription of TNFSF13B (BAFF). This expression profile is consistent with the hypothesis that Th* cells have undergone multiple rounds of antigen stimulation and in that course overcome intrinsic barriers that normally reduce the responsiveness and persistence of T cells, making them effective and long-term controllers of persistent or recurrent infections.

The studies herein indicate that Th* cells are important in controlling chronic/latent infections and also play a role in pathogenesis and drug resistance of autoimmune diseases. Furthermore, they represent a long-lived human T cell subset, thus may be important to understanding mechanisms of long-term immune memory and vaccine responses. These cells and their transcriptional signature may be exploited to improve diagnosis, characterization and treatment of not only TB patients but also patients with autoimmune diseases.

Example 10: The Identification and Characterization of CD4 T Cell Epitopes from Non-Tuberculose *Mycobacterium* that Modulate the Immune Response Against MTB In parallel to the results described above, disclosed herein are a number of epitopes and antigens that allow the differential diagnosis of MTB and Non-tuberculose mycobacteria (NTM) infection. These data have value in the design of both MTB specific and NTM/MTB cross-reactive or, "naturally boosted" vaccines. The NTM epitopes and antigens identified can additively be used to monitor the performance of NTM-based vaccines.

Finally, disclosed herein are a set of broadly cross-reactive T cell epitopes which elicit production of the anti-inflammatory cytokine, IL-10, that can be used to dampen inflammation associated with severe active TB cases as well as other infectious, auto-immune, and allergic disease. These epitopes and/or antigens can also be used to generate novel BCG vaccines where potentially anti-inflammatory antigens/epitopes can be removed to enhance the efficacy of BCG-based vaccines for MTB disease.

Conservation of TB epitope sequences within the MTB/NTM complexes and broadly within other bacteria, dictates mutually exclusive IFNg and IL10 reactivity in different human populations It is generally postulated that *M. tuberculosis* (MTB)-specific CD4+ T cell responses are not present in non-BCG vaccinated and non-MTB infected (i.e. non-exposed) individuals. The inventors have previously performed a detailed analysis of epitopes identified in an unbiased genome-wide analysis of CD4 MTB recognition using PBMCs from individuals latently infected with MTB (LTBI) or non-exposed individuals. This analysis revealed that surprisingly, some reactivity was detected in non-exposed individuals (FIG. 8). Specifically, the epitopes identified could be divided into 3 categories; LTBI-specific, Mixed and Non-LTBI-specific, based on whether they were exclusively recognized in LTBIs, recognized in both LTBIs and TB uninfected, non-BCG vaccinated donors (healthy controls, HC), or recognized exclusively in HC and not in LTBIs. For this purpose, the inventors analyzed the responses observed against epitopes that were recognized by at least 2 donors. As shown, totally LTBI-specific epitopes (those for which no reactivity was observed in any of the 31 HC donors tested) accounted for 72% of the epitopes, and 62% of the total reactivity. Mixed epitopes (for which some reactivity was observed in both TB and HC donors) accounted for 21% of the epitopes and 36% of the reactivity. Interestingly, some epitopes that accounted for 6% of the epitopes and 2% of the reactivity were only recognized by HC individuals.

The pattern of reactivity presented above might be due to exposure to NTMs and that the reactivity seen in controls are directed against epitopes totally or largely conserved in these strains. To test this hypothesis, representative NTM were chosen based on available genome sequences at the time of analysis (January 2012). A total of 15 NTM species were selected; *M. abscessus, M. avium* 104, *M. avium* subsps paratuberculosis k 10, *M. gilvum* PYR-GCK, *M. marinum* M, *M. smegmatis* str. MC2 155, M. sp. JDM601, M. sp. JLS, M. sp. KMS, M. sp. MCS, M. sp. Spyrl (*gilvum*), *M. ulcerans* Agy99, *M. vanbaalenii* PYR-1, *M. colombiense* CECT 3035, *M. parascrofulaceum* ATCC BAA-614. The sequence of the 155 epitopes recognized by 2 or more donors described above was next compared to these full genome sequences. The number of genomes in which each of the epitopes was conserved was tabulated for each of the epitope classifications from FIG. 1B. To allow for likely cross reactivity at the immunological level of closely related sequences, one single substitution was allowed per epitope.

The results of this analysis are shown in FIG. 9A. The LTBI-specific epitopes were clearly associated with low conservation (on average 1.7 (11%) of the 15 NTM genomes), while the mixed epitopes were conserved in a significantly higher number (3.3, 22%; p=0.0164). Finally, the non-LTBI-specific epitopes were conserved in almost 50% of the 15 genomes analyzed ($p<0.0001$).

The number of epitopes conserved in each strain appeared to correlate with how closely related the strains are in the phylogenetic tree. Highest numbers of instances of conservation were observed in *M. marinum* and *M. ulcerans* that are also most closely related to MTB (data not shown).

The degree of conservation of the 112 LTBI-specific epitopes was also evaluated. The dN/dS ratio was calculated using a similar methodology to that described by Comas et al. The relative degree of sequence conservation in the epitope and non-epitope regions was assessed by comparing non-synonymous and synonymous substitutions. Nucleotide sequence concatenates were made for epitope and non-epitope regions from the 21 MTB strains. The number of non-synonymous nucleotide substitutions per non-synonymous site (dN) and the number or synonymous nucleotide substitutions per synonymous site (dS) were calculated by the Nei-Gojobori method as implemented in the MEGA5 program. The dN/dS values for all regions were less than 1 (FIG. 9B), which indicated that purifying selection plays a major role in the evolution of these regions. When the dN/dS values were compared among different genomic regions, it was confirmed that epitopes are more conserved compared to antigens and non-epitopes (FIG. 9B). In conclusion, these results suggest that HC individuals cross-recognize MTB sequences and that this recognition correlates with conservation of those sequences in NTMs.

To further test whether the degree of conservation across different mycobacteria species directed the specificity of recognition in different donor cohorts, the sequences of the 155 epitopes were further analyzed. Based on the results of the conservancy analysis the epitopes were subdivided in; epitopes found only in MTB (55 epitopes) and epitopes also conserved in NTM (69 epitopes). Epitope conservation in additional bacteria other than Mycobacteria was also determined and these epitopes broadly conserved in non-Mycobacteria were excluded from the pools (see below).

Pools of approximately 20 epitopes each were prepared and then tested for reactivity in 20 LTBIs, 20 HC controls and 19 BCG vaccinated individuals. The results of this analysis are shown in FIG. 9C, and expressed as total response per donor observed for the two epitope categories.

As expected, significant higher reactivity was detected in LTBIs as compared to HC or BCG individuals, for both the MTB-only and the NTM-conserved pools. The highest discrimination in terms of magnitude was obtained with the pools of MTB/NTM sequences ($p<0.0001$).

In the case of LTBIs, significantly more of the reactivity was directed towards MTB/NTM-specific sequences, suggesting that NTM-exposure boosts the reactivity to conserved sequences. For HC and BCG individuals, a trend towards higher responses was also noted for the pools of epitopes conserved in NTM. In conclusion, these data confirms the hypothesis that reactivity of MTB sequences recognized by both LTBIs and HC individuals is explained by sequence conservation in NTM.

The data herein implies that preexisting immunity and occasional boosting might be provided by exposure to NTMs, in a low MTB-complex exposure population such as the one from the general San Diego area. This might be viewed as desirable, or alternatively contributing an undesired confounding factor in evaluation of vaccination strategies. Regardless, whether or not preexisting, non-TB-complex related reactivity is present in the general population is an important issue has implication for the development of vaccination strategies. To further investigate this issue, epitope reactivity data (Lindestamm-Arlehamn et al, 2012) was mapped back to the specific antigens from which the epitopes were derived. Antigens recognized by 2 or more donors were further categorized as LTBI-specific or crossreactive according to the following criteria; antigens were categorized as LTBI-specific if there was a lack of reactivity in HC individuals, or if the ratio between response frequency and total SFC for LTBI/HC were >4. All other antigens were categorized as crossreactive.

FIG. 10 shows the response frequency and magnitude of antigens that were recognized that are currently included in TB vaccines in clinical development. As can be seen, vaccine antigens Rv0288 (TB10.4/cfp7), Rv1886c (PPE42), Rv2608 (Ag 85B) and Rv3804c (Ag 85A) are widely cross-reactive, while antigens Rv1196, Rv3619c, Rv3620c and Rv3875 appear to be exclusively specific.

The data herein suggest that T cell reactivity can be detected in HC infected individuals, presumably induced by exposure to NTMs. As a corollary, it should be possible to identify NTM-specific epitopes. These epitopes could be utilized as a tool at the research and diagnostic level.

To address this point, all possible 15-mers from the 15 strains of NTM were selected (data not shown). Next, all peptides absent from 21 TB strains (allowing up to 2 substitutions) were selected. This resulted in a total of 11,532,048 peptides. All 15-mers conserved in 5 of the 15 strains were further selected, for a total of 116,070. This peptide set was used to predict binding affinity for a panel of 24 HLA class II alleles. A total of 1,583 promiscuous binders that bind 18 of the 25 alleles were selected, arranged in 159 pools of 10 peptides each, and the ex vivo production of IFNγ by PBMC from 30 HC individuals induced by each of the 159 pools was measured utilizing ELISPOT. Positive pools were deconvoluted and 106 individual NTM-epitopes were identified (FIG. 11A).

The top 20 epitopes account for 46% of the total response and are conserved on average in 40% of the 15 NTM strains. Individual donors recognized, on average, 7 epitopes (mean of 1, range 0-79), underlining the exposure rate of NTM in these individuals. The top 20 epitopes were pooled and tested in LTBI and HC donors (FIG. 11B). The response frequency to the NTM-specific peptide pool and the magnitude of response were comparable between the two donor cohorts. These results indicate that NTM-specific epitopes can be defined.

To further test whether the degree of conservation across different mycobacteria species directed the specificity of recognition in different donor cohorts, the sequences of the epitopes were further analyzed, by testing for their conservancy in the set of NTMs described above, and 44 classes of bacteria other than *Mycobacterium*. Based on the results of this and previous conservancy analysis, the epitopes were subdivided in; epitopes found in MTB and NTM (115 epitopes), and broadly conserved epitopes (53 epitopes). To maximize signal strength, these pools included all epitopes identified (Lindestamm-Arlehamn et al, 2012), and not just epitopes recognized by 2 donors or more. Pools of approximately 20 epitopes each were prepared and then tested for reactivity in 19 LTBIs and 26 HC controls. The total response per donor observed for the two epitope categories is shown in FIG. 12A. Interestingly, the detected reactivity against broadly conserved epitopes was significantly less than MTB/NTM-specific sequences for both LTBI and HC individuals.

The low reactivity of the broadly conserved epitopes was scrutinized further. The low reactivity might be either due to the fact that these sequences are relatively rare within the genome, or alternatively that broad expression and conservation amongst different bacterial classes might lead to tolerization of T cells specific for those sequences.

To address the first issue, the frequency of each of these sequence types in the original set of the 20,216 peptides screened for reactivity was calculated. TB specific sequences accounted for 8,717 of the peptides and account for 66 of the dominant epitopes. Thus the probability of any of these peptides of being an epitope is 0.76%. Similarly, sequences conserved in mycobacteria but not in other bacteria accounted for 7258 of the peptides and account for 69 of the epitopes. Thus, these sequences had a probability of recognition of 0.95%, only mildly higher than the ones found in the MTB complex only. However, the sequences also found broadly in other bacteria, were 4241, and accounted for 15 epitopes (0.47%). This difference is statistically significant, with a Chi Square value of 7.938 and a two tailed p=0.005 (p=0.18 for MTB-specific vs. MTB/NTM conserved; p=0.06 for MTB vs. broadly conserved) (FIG. 12B).

These data suggest that broad conservation in several bacterial classes leads to decreased reactivity of MTB sequences. This phenomenon was indeed traceable to conservation within bacteria, because less than 0.1% of the broadly conserved peptides were found to be conserved in the human genome. Table 4 provides a list of NTM epitopes which represent 46% of the spot forming cells (SFC) and a supplemental attached table provides a list of all NTM epitopes identified.

Example 11: Tolerance to Broadly Conserved Epitopes

The sequence conservation analysis disclosed herein suggested that the T cell repertoire recognizing broadly conserved epitopes could potentially be either deleted. Alternatively, T cells recognizing these epitopes might still exist but be associated with a regulatory phenotype, and perhaps produce IL-10 instead of IFNγ.

To test this hypothesis, the the HLA binding capacity of the 4241 broadly conserved peptides for common HLA class II alleles was predicted. Next peptides were selected predicted to bind with high affinity to alleles expressed in representative HC donors were tested for IL-10 production. Several frequently recognized IL-10 producing peptides could be identified (FIG. 13A), none of which produced a significant amount of IFNγ (FIG. 13B).

The phenotype of these TB-specific IL-10 producing was further investigated. Chemokine receptor expression patterns characteristic of all four well characterized Th subsets (Th1, Th2, Th17 and CXCR3+CCR6+) were observed. However, the majority of IL-10 producing cells were either Th17- or Th2-like (FIG. 13C). To further analyze whether the IL-10 producing cells also expressed classic markers of Tregs, CD25hiCD127loCD4+ and CD25loCD4+ cells were sorted and compared for IL-10 production (FIG. 13D). IL-10 could be detected from the CD25hi, indicating that regulatory T cells mediate the production of IL-10. Table 3 provides a list of the T cell epitopes identified that elicit this cytokine signature.

TABLE 1

| gene | th1 vs. th17 significant | th* up | th* down | heatmap grouping I | heatmap grouping II |
|---|---|---|---|---|---|
| A1BG | TRUE | FALSE | FALSE | Th* ~Th17 | |
| A2M | TRUE | FALSE | FALSE | Th* intermediate | |
| A2MP1 | FALSE | FALSE | FALSE | | remainder |
| AACS | TRUE | FALSE | FALSE | Th* ~Th1 | |
| AARS | FALSE | FALSE | FALSE | | remainder |
| AASS | FALSE | FALSE | FALSE | | remainder |
| ABCA1 | FALSE | FALSE | FALSE | | remainder |
| ABCA7 | FALSE | FALSE | TRUE | | Th* <all |
| ABCB1 | FALSE | TRUE | FALSE | | Th* >all |
| ABCC10 | FALSE | FALSE | FALSE | | remainder |
| ABCD2 | FALSE | FALSE | FALSE | | remainder |
| ABCD3 | FALSE | FALSE | FALSE | | remainder |
| ABCG2 | TRUE | TRUE | FALSE | Th* ~Th1 | Th* >all |
| ABHD10 | FALSE | FALSE | FALSE | | remainder |
| ABI3 | TRUE | FALSE | FALSE | Th* intermediate | |
| ACAD9 | FALSE | FALSE | FALSE | | remainder |
| ACAP1 | FALSE | FALSE | TRUE | | Th* <all |
| ACBD5 | FALSE | TRUE | FALSE | | Th* >all |
| ACCS | FALSE | FALSE | FALSE | | remainder |
| ACOT8 | FALSE | FALSE | TRUE | | Th* <all |
| ACOT9 | FALSE | FALSE | TRUE | | Th* <all |
| ACP5 | FALSE | FALSE | TRUE | | Th* <all |
| ACSM1 | TRUE | TRUE | FALSE | Th* ~Th1 | Th* >all |
| ACSS2 | FALSE | FALSE | FALSE | | remainder |
| ACTN1 | FALSE | FALSE | FALSE | | remainder |
| ACTN4 | FALSE | FALSE | FALSE | | remainder |
| ACVR1C | FALSE | FALSE | FALSE | | remainder |
| ACVR2A | FALSE | FALSE | FALSE | | remainder |
| ADAM12 | TRUE | FALSE | FALSE | Th* ~Th17 | |
| ADAM19 | TRUE | FALSE | FALSE | Th* intermediate | |
| ADAM23 | FALSE | TRUE | FALSE | | Th* >all |
| ADAMTS10 | TRUE | FALSE | FALSE | Th* intermediate | |
| ADAMTSL4 | FALSE | FALSE | TRUE | | Th* <all |
| ADAMTSL5 | FALSE | FALSE | TRUE | | Th* <all |
| ADHFE1 | FALSE | FALSE | TRUE | | Th* <all |
| ADPRH | TRUE | FALSE | FALSE | Th* ~Th1 | |
| ADRB2 | TRUE | TRUE | FALSE | Th* ~Th1 | Th* >all |
| AEBP1 | TRUE | FALSE | FALSE | Th* intermediate | |
| AFAP1 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| AFF2 | FALSE | FALSE | FALSE | | remainder |
| AGAP1 | TRUE | FALSE | FALSE | Th* ~Th1 | |
| AIG1 | FALSE | TRUE | FALSE | | Th* >all |
| AIM2 | FALSE | FALSE | FALSE | | remainder |
| AIRE | TRUE | FALSE | FALSE | Th* ~Th1 | |
| AK5 | FALSE | FALSE | FALSE | | remainder |
| AKAP12 | FALSE | FALSE | FALSE | | remainder |
| AKR7A2 | FALSE | FALSE | FALSE | | remainder |
| AKTIP | FALSE | FALSE | TRUE | | Th* <all |
| ALAS1 | FALSE | FALSE | FALSE | | remainder |
| ALDH6A1 | FALSE | FALSE | FALSE | | remainder |
| ALDOC | FALSE | FALSE | FALSE | | remainder |
| ALOX5 | FALSE | FALSE | FALSE | | remainder |
| ALOX5AP | TRUE | FALSE | FALSE | Th* intermediate | |
| ALOXE3 | FALSE | TRUE | FALSE | | Th* >all |
| ALPK3 | FALSE | FALSE | FALSE | | remainder |
| ALS2CL | FALSE | FALSE | FALSE | | remainder |
| AMICA1 | FALSE | FALSE | FALSE | | remainder |
| AMPD2 | TRUE | FALSE | FALSE | Th* intermediate | |
| AMY2B | FALSE | FALSE | FALSE | | remainder |
| ANAPC2 | FALSE | FALSE | TRUE | | Th* <all |
| ANK1 | TRUE | FALSE | FALSE | Th* ~Th17 | |
| ANKRD18A | FALSE | FALSE | FALSE | | remainder |
| ANKRD19P | FALSE | FALSE | FALSE | | remainder |
| ANKRD36 | FALSE | FALSE | TRUE | | Th* <all |
| ANKRD36BP2 | TRUE | FALSE | FALSE | Th* ~Th17 | |
| ANKRD55 | FALSE | FALSE | TRUE | | Th* <all |
| ANKS1B | FALSE | FALSE | FALSE | | remainder |
| ANKS6 | FALSE | FALSE | FALSE | | remainder |
| ANLN | FALSE | FALSE | FALSE | | remainder |
| ANO9 | FALSE | FALSE | FALSE | | remainder |
| ANXA2 | FALSE | FALSE | FALSE | | remainder |
| AP1G2 | FALSE | FALSE | FALSE | | remainder |
| AP3B1 | FALSE | FALSE | FALSE | | remainder |
| AP3M2 | FALSE | FALSE | FALSE | | remainder |
| APBA2 | TRUE | FALSE | FALSE | Th* ~Th1 | |
| APOBEC3H | FALSE | FALSE | FALSE | | remainder |
| AQP3 | TRUE | FALSE | FALSE | Th* ~Th17 | |
| AR | FALSE | FALSE | FALSE | | remainder |
| ARAP1 | FALSE | FALSE | TRUE | | Th* <all |
| ARAP3 | TRUE | FALSE | FALSE | Th* ~Th1 | |
| ARFGAP1 | FALSE | FALSE | FALSE | | remainder |
| ARFRP1 | FALSE | FALSE | FALSE | | remainder |
| ARHGAP21 | FALSE | FALSE | FALSE | | remainder |
| ARHGAP26 | TRUE | FALSE | FALSE | Th* intermediate | |
| ARHGAP31 | TRUE | FALSE | FALSE | Th* ~Th1 | |
| ARHGAP32 | FALSE | FALSE | FALSE | | remainder |
| ARHGEF1 | FALSE | FALSE | FALSE | | remainder |
| ARHGEF11 | FALSE | FALSE | FALSE | | remainder |
| ARHGEF4 | FALSE | FALSE | FALSE | | remainder |
| ARID5B | FALSE | FALSE | TRUE | | Th* <all |
| ARL4C | FALSE | FALSE | FALSE | | remainder |
| ARMC12 | TRUE | FALSE | FALSE | Th* ~Th1 | |
| ARMCX4 | FALSE | FALSE | FALSE | | remainder |
| ARPC5L | FALSE | FALSE | FALSE | | remainder |
| ARRDC1 | FALSE | FALSE | TRUE | | Th* <all |
| ASAP3 | FALSE | FALSE | TRUE | | Th* <all |
| ASNSD1 | FALSE | FALSE | FALSE | | remainder |
| ASPH | FALSE | FALSE | FALSE | | remainder |
| ASPM | FALSE | TRUE | TRUE | | Th* >all |
| ASTL | FALSE | FALSE | TRUE | | Th* <all |
| ATCAY | FALSE | FALSE | FALSE | | remainder |
| ATF7IP2 | FALSE | FALSE | FALSE | | remainder |
| ATG2A | FALSE | FALSE | FALSE | | remainder |
| ATG7 | FALSE | FALSE | FALSE | | remainder |
| ATL3 | FALSE | FALSE | FALSE | | remainder |
| ATP10A | TRUE | FALSE | FALSE | Th* intermediate | |
| ATP13A1 | FALSE | FALSE | TRUE | | Th* <all |
| ATP1A3 | FALSE | FALSE | TRUE | | Th* <all |
| ATP6V0A1 | FALSE | FALSE | FALSE | | remainder |
| ATP8B3 | TRUE | FALSE | TRUE | Th* ~Th1 | Th* <all |
| ATP9A | FALSE | FALSE | FALSE | | remainder |
| ATPAF1-AS1 | FALSE | TRUE | FALSE | | Th* >all |
| ATXN7L1 | FALSE | FALSE | FALSE | | remainder |
| ATXN7L3 | FALSE | TRUE | FALSE | | Th* >all |
| AURKAIP1 | FALSE | FALSE | FALSE | | remainder |
| AUTS2 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| AXIN2 | FALSE | FALSE | FALSE | | remainder |
| B2M | FALSE | FALSE | TRUE | | Th* <all |
| B3GALT2 | FALSE | FALSE | FALSE | | remainder |
| B3GALTL | FALSE | TRUE | FALSE | | Th* >all |
| B3GNT5 | TRUE | FALSE | FALSE | Th* ~Th17 | |
| B3GNTL1 | FALSE | FALSE | TRUE | | Th* <all |
| B4GALT5 | TRUE | FALSE | FALSE | Th* ~Th17 | |
| B7H6 | TRUE | FALSE | FALSE | Th* ~Th1 | |
| BABAM1 | FALSE | FALSE | FALSE | | remainder |
| BACE1 | FALSE | FALSE | TRUE | | Th* <all |
| BACH2 | TRUE | FALSE | FALSE | Th* ~Th1 | |
| BAD | FALSE | FALSE | TRUE | | Th* <all |
| BAI2 | FALSE | FALSE | FALSE | | remainder |
| BBC3 | FALSE | FALSE | FALSE | | remainder |
| BCAT1 | FALSE | FALSE | FALSE | | remainder |
| BCAT2 | FALSE | FALSE | FALSE | | remainder |
| BCL2 | FALSE | FALSE | FALSE | | remainder |
| BCL2A1 | TRUE | FALSE | FALSE | Th* ~Th1 | |
| BCL2L11 | FALSE | TRUE | FALSE | | Th* >all |
| BCL3 | FALSE | FALSE | FALSE | | remainder |
| BCL7A | TRUE | FALSE | FALSE | Th* ~Th17 | |
| BFSP2 | TRUE | FALSE | FALSE | Th* ~Th1 | |
| BHLHE40 | FALSE | FALSE | FALSE | | remainder |
| BIN1 | FALSE | FALSE | TRUE | | Th* <all |
| BLOC1S3 | FALSE | FALSE | FALSE | | remainder |
| BPGM | TRUE | FALSE | FALSE | Th* intermediate | |
| BRD4 | FALSE | FALSE | FALSE | | remainder |
| BSCL2 | FALSE | FALSE | FALSE | | remainder |
| BSG | FALSE | FALSE | TRUE | | Th* <all |
| BTBD11 | TRUE | FALSE | FALSE | Th* ~Th1 | |
| BTD | FALSE | FALSE | FALSE | | remainder |
| BTG1 | FALSE | FALSE | FALSE | | remainder |
| BUB1 | FALSE | FALSE | TRUE | | Th* <all |
| BUB1B | FALSE | FALSE | FALSE | | remainder |
| C10orf12 | FALSE | FALSE | FALSE | | remainder |
| C10orf128 | FALSE | FALSE | TRUE | | Th* <all |
| C11orf2 | FALSE | FALSE | TRUE | | Th* <all |
| C11orf21 | FALSE | FALSE | FALSE | | remainder |
| C11orf31 | FALSE | TRUE | FALSE | | Th* >all |
| C11orf35 | FALSE | FALSE | TRUE | | Th* <all |
| C11orf49 | FALSE | FALSE | TRUE | | Th* <all |
| C11orf75 | TRUE | TRUE | TRUE | Th* ~Th17 | Th* >all |
| C11orf9 | FALSE | FALSE | FALSE | | remainder |
| C12orf33 | TRUE | TRUE | FALSE | Th* ~Th1 | Th* >all |
| C12orf53 | FALSE | TRUE | FALSE | | Th* >all |
| C12orf57 | FALSE | FALSE | TRUE | | Th* <all |
| C12orf75 | FALSE | FALSE | FALSE | | remainder |
| C14orf129 | FALSE | FALSE | FALSE | | remainder |
| C14orf132 | FALSE | FALSE | FALSE | | remainder |
| C14orf135 | FALSE | FALSE | FALSE | | remainder |
| C14orf28 | FALSE | TRUE | FALSE | | Th* >all |
| C14orf49 | TRUE | FALSE | FALSE | Th* ~Th1 | |
| C14orf64 | FALSE | FALSE | FALSE | | remainder |
| C15orf44 | FALSE | FALSE | FALSE | | remainder |
| C15orf53 | TRUE | FALSE | FALSE | Th* ~Th1 | |
| C16orf45 | FALSE | FALSE | FALSE | | remainder |
| C16orf48 | FALSE | TRUE | FALSE | | Th* >all |
| C16orf74 | FALSE | FALSE | FALSE | | remainder |
| C17orf50 | FALSE | TRUE | FALSE | | Th* >all |
| C17orf66 | TRUE | FALSE | FALSE | Th* intermediate | |
| C17orf89 | FALSE | FALSE | FALSE | | remainder |
| C19orf55 | FALSE | FALSE | FALSE | | remainder |
| C19orf6 | FALSE | FALSE | FALSE | | remainder |
| C19orf60 | FALSE | FALSE | TRUE | | Th* <all |
| C19orf70 | FALSE | FALSE | TRUE | | Th* <all |
| C1orf162 | TRUE | FALSE | FALSE | Th* ~Th1 | |
| C1orf177 | FALSE | FALSE | FALSE | | remainder |
| C1orf200 | FALSE | TRUE | FALSE | | Th* >all |
| C1orf21 | FALSE | FALSE | FALSE | | remainder |
| C1orf95 | FALSE | TRUE | TRUE | | Th* >all |
| C1orf96 | TRUE | FALSE | FALSE | Th* intermediate | |
| C20orf3 | FALSE | FALSE | FALSE | | remainder |
| C21orf56 | FALSE | FALSE | TRUE | | Th* <all |
| C21orf63 | FALSE | FALSE | FALSE | | remainder |
| C22orf25 | FALSE | FALSE | FALSE | | remainder |
| C22orf32 | FALSE | FALSE | FALSE | | remainder |
| C2orf76 | FALSE | FALSE | TRUE | | Th* <all |

TABLE 1-continued

| gene | th1 vs. th17 significant | th* up | th* down | heatmap grouping I | heatmap grouping II |
|---|---|---|---|---|---|
| C3AR1 | FALSE | TRUE | FALSE | | Th* >all |
| C3orf52 | FALSE | FALSE | TRUE | | Th* <all |
| C3orf67 | FALSE | FALSE | FALSE | | remainder |
| C4orf32 | TRUE | FALSE | FALSE | Th* intermediate | |
| C4orf34 | FALSE | FALSE | FALSE | | remainder |
| C4orf44 | FALSE | TRUE | FALSE | | Th* >all |
| C5orf25 | FALSE | FALSE | FALSE | | remainder |
| C5orf62 | FALSE | FALSE | FALSE | | remainder |
| C6orf228 | FALSE | TRUE | FALSE | | Th* >all |
| C6orf25 | FALSE | TRUE | FALSE | | Th* >all |
| C7orf43 | FALSE | FALSE | FALSE | | remainder |
| C7orf55 | FALSE | FALSE | FALSE | | remainder |
| C8orf83 | FALSE | TRUE | FALSE | | Th* >all |
| C9orf103 | FALSE | FALSE | FALSE | | remainder |
| C9orf142 | FALSE | FALSE | FALSE | | remainder |
| C9orf16 | FALSE | FALSE | TRUE | | Th* <all |
| CABIN1 | FALSE | FALSE | FALSE | | remainder |
| CACNA1C | FALSE | TRUE | FALSE | | Th* >all |
| CACNA1H | FALSE | FALSE | TRUE | | Th* <all |
| CACNA1I | FALSE | FALSE | FALSE | | remainder |
| CACNA2D2 | FALSE | FALSE | FALSE | | remainder |
| CACNA2D4 | FALSE | FALSE | FALSE | | remainder |
| CADM1 | FALSE | FALSE | TRUE | | Th* <all |
| CAMK1D | FALSE | TRUE | FALSE | | Th* >all |
| CAMK2N1 | FALSE | TRUE | FALSE | | Th* >all |
| CAMSAP2 | TRUE | FALSE | FALSE | Th* ~Th1 | |
| CAMTA1 | TRUE | FALSE | FALSE | Th* intermediate | |
| CAPG | TRUE | FALSE | FALSE | Th* intermediate | |
| CAPN5 | FALSE | FALSE | FALSE | | remainder |
| CARKD | FALSE | FALSE | FALSE | | remainder |
| CARS2 | FALSE | FALSE | FALSE | | remainder |
| CASP7 | FALSE | FALSE | FALSE | | remainder |
| CASS4 | FALSE | FALSE | FALSE | | remainder |
| CASZ1 | FALSE | FALSE | FALSE | | remainder |
| CATSPERB | FALSE | TRUE | FALSE | | Th* >all |
| CBLB | FALSE | FALSE | FALSE | | remainder |
| CBR4 | FALSE | TRUE | FALSE | | Th* >all |
| CCDC112 | FALSE | FALSE | FALSE | | remainder |
| CCDC124 | FALSE | FALSE | TRUE | | Th* <all |
| CCDC130 | FALSE | FALSE | FALSE | | remainder |
| CCDC141 | FALSE | FALSE | TRUE | | Th* <all |
| CCDC50 | FALSE | FALSE | FALSE | | remainder |
| CCDC65 | FALSE | FALSE | FALSE | | remainder |
| CCL20 | FALSE | TRUE | FALSE | | Th* >all |
| CCL4 | FALSE | FALSE | FALSE | | remainder |
| CCL5 | TRUE | FALSE | FALSE | Th* ~Th1 | |
| CCNB1 | TRUE | FALSE | FALSE | Th* intermediate | |
| CCNB2 | FALSE | FALSE | TRUE | | Th* <all |
| CCND1 | FALSE | FALSE | FALSE | | remainder |
| CCNG2 | TRUE | FALSE | FALSE | Th* ~Th17 | |
| CCNI | FALSE | FALSE | FALSE | | remainder |
| CCR10 | TRUE | FALSE | FALSE | Th* ~Th1 | |
| CCR2 | FALSE | TRUE | FALSE | | Th* >all |
| CCR4 | TRUE | FALSE | FALSE | Th* ~Th1 | |
| CCR5 | TRUE | FALSE | FALSE | Th* intermediate | |
| CCR6 | TRUE | FALSE | FALSE | Th* ~Th17 | |
| CCR8 | TRUE | FALSE | FALSE | Th* ~Th1 | |
| CCR9 | FALSE | TRUE | FALSE | | Th* >all |
| CD101 | TRUE | FALSE | FALSE | Th* ~Th1 | |
| CD109 | FALSE | FALSE | TRUE | | Th* <all |
| CD160 | FALSE | TRUE | FALSE | | Th* >all |
| CD1C | FALSE | TRUE | FALSE | | Th* >all |
| CD200 | FALSE | FALSE | FALSE | | remainder |
| CD200R1 | FALSE | FALSE | FALSE | | remainder |
| CD226 | FALSE | FALSE | FALSE | | remainder |
| CD27 | FALSE | FALSE | FALSE | | remainder |
| CD300A | TRUE | FALSE | FALSE | Th* intermediate | |
| CD37 | FALSE | FALSE | TRUE | | Th* <all |
| CD5 | FALSE | FALSE | FALSE | | remainder |
| CD52 | FALSE | FALSE | FALSE | | remainder |
| CD58 | FALSE | FALSE | TRUE | | Th* <all |
| CD79A | FALSE | FALSE | TRUE | | Th* <all |
| CD81 | FALSE | FALSE | FALSE | | remainder |
| CD82 | FALSE | FALSE | FALSE | | remainder |
| CDC42BPB | TRUE | FALSE | TRUE | Th* ~Th1 | Th* <all |
| CDC42BPG | FALSE | FALSE | TRUE | | Th* <all |
| CDC42EP3 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| CDC6 | FALSE | FALSE | FALSE | | remainder |
| CDCA7 | FALSE | FALSE | TRUE | | Th* <all |
| CDCA7L | TRUE | FALSE | FALSE | Th* ~Th1 | |
| CDHR3 | FALSE | FALSE | FALSE | | remainder |
| CDK2AP2 | FALSE | FALSE | FALSE | | remainder |
| CDK6 | FALSE | FALSE | FALSE | | remainder |
| CDKN2D | FALSE | FALSE | FALSE | | remainder |
| CDKN3 | FALSE | FALSE | TRUE | | Th* <all |
| CDO1 | FALSE | FALSE | FALSE | | remainder |
| CDS1 | FALSE | TRUE | FALSE | | Th* >all |
| CEBPB | TRUE | FALSE | FALSE | Th* ~Th1 | |
| CEBPD | FALSE | TRUE | FALSE | | Th* >all |
| CECR5 | FALSE | FALSE | FALSE | | remainder |
| CELA1 | FALSE | FALSE | FALSE | | remainder |
| CENPF | FALSE | FALSE | TRUE | | Th* <all |
| CENPV | FALSE | FALSE | FALSE | | remainder |
| CEP128 | FALSE | FALSE | FALSE | | remainder |
| CERKL | FALSE | FALSE | FALSE | | remainder |
| CERS6 | FALSE | FALSE | FALSE | | remainder |
| CFB | FALSE | FALSE | TRUE | | Th* <all |
| CFH | FALSE | TRUE | FALSE | | Th* >all |
| CHCHD10 | FALSE | FALSE | FALSE | | remainder |
| CHCHD4 | FALSE | FALSE | TRUE | | Th* <all |
| CHDH | TRUE | FALSE | FALSE | Th* ~Th1 | |
| CHERP | FALSE | FALSE | TRUE | | Th* <all |
| CHGB | FALSE | FALSE | FALSE | | remainder |
| CHI3L2 | FALSE | FALSE | FALSE | | remainder |
| CHML | FALSE | FALSE | FALSE | | remainder |
| CHN1 | TRUE | FALSE | FALSE | Th* ~Th17 | |
| CHN2 | TRUE | FALSE | FALSE | Th* intermediate | |
| CHRNA6 | FALSE | FALSE | FALSE | | remainder |
| CHRNB2 | FALSE | FALSE | TRUE | | Th* <all |
| CHST2 | FALSE | FALSE | FALSE | | remainder |
| CIITA | FALSE | FALSE | TRUE | | Th* <all |
| CIRH1A | FALSE | FALSE | FALSE | | remainder |
| CISH | FALSE | TRUE | FALSE | | Th* >all |
| CIT | FALSE | FALSE | FALSE | | remainder |
| CKS1B | FALSE | FALSE | FALSE | | remainder |
| CKS2 | FALSE | FALSE | TRUE | | Th* <all |
| CLASRP | FALSE | FALSE | FALSE | | remainder |
| CLDND1 | FALSE | FALSE | FALSE | | remainder |
| CLEC2B | FALSE | FALSE | FALSE | | remainder |
| CLIC4 | FALSE | TRUE | FALSE | | Th* >all |
| CLIP3 | FALSE | FALSE | FALSE | | remainder |
| CLPP | FALSE | FALSE | TRUE | | Th* <all |
| CLTB | FALSE | FALSE | TRUE | | Th* <all |
| CLU | TRUE | FALSE | FALSE | Th* ~Th1 | |
| CMC1 | TRUE | FALSE | FALSE | Th* intermediate | |
| CMIP | FALSE | FALSE | FALSE | | remainder |
| CMTM6 | FALSE | FALSE | FALSE | | remainder |
| CNTNAP1 | TRUE | FALSE | FALSE | Th* ~Th1 | |
| COIL | FALSE | FALSE | FALSE | | remainder |
| COL17A1 | FALSE | FALSE | FALSE | | remainder |
| COL1A1 | FALSE | FALSE | TRUE | | Th* <all |
| COL24A1 | FALSE | TRUE | FALSE | | Th* >all |
| COL5A1 | TRUE | FALSE | FALSE | Th* intermediate | |
| COL5A3 | TRUE | TRUE | FALSE | Th* ~Th17 | Th* >all |
| COL6A2 | TRUE | FALSE | FALSE | Th* ~Th17 | |
| COL6A3 | FALSE | FALSE | TRUE | | Th* <all |
| COL9A2 | FALSE | TRUE | FALSE | | Th* >all |
| COLQ | FALSE | TRUE | FALSE | | Th* >all |
| COMMD3 | FALSE | FALSE | FALSE | | remainder |
| COMMD6 | FALSE | FALSE | TRUE | | Th* <all |
| COPE | FALSE | FALSE | TRUE | | Th* <all |
| COPS5 | FALSE | FALSE | FALSE | | remainder |
| COQ5 | FALSE | FALSE | FALSE | | remainder |
| CORO1A | FALSE | FALSE | TRUE | | Th* <all |
| CORO1B | FALSE | FALSE | FALSE | | remainder |
| CORO2A | FALSE | FALSE | FALSE | | remainder |
| COTL1 | FALSE | FALSE | TRUE | | Th* <all |
| COX16 | FALSE | FALSE | TRUE | | Th* <all |
| COX6B1 | FALSE | FALSE | FALSE | | remainder |
| CPA5 | FALSE | TRUE | TRUE | | Th* >all |
| CPEB2 | FALSE | FALSE | FALSE | | remainder |
| CPLX2 | FALSE | FALSE | FALSE | | remainder |
| CPNE2 | FALSE | FALSE | FALSE | | remainder |
| CPNE7 | TRUE | FALSE | FALSE | Th* ~Th1 | |

TABLE 1-continued

| gene | th1 vs. th17 significant | th* up | th* down | heatmap grouping I | heatmap grouping II |
|---|---|---|---|---|---|
| CPSF1 | FALSE | FALSE | TRUE | | Th* <all |
| CPSF3L | FALSE | FALSE | TRUE | | Th* <all |
| CR1 | FALSE | TRUE | FALSE | | Th* >all |
| CREBBP | FALSE | FALSE | FALSE | | remainder |
| CRIP1 | TRUE | FALSE | FALSE | Th* ~Th1 | |
| CRIP2 | TRUE | FALSE | TRUE | Th* ~Th1 | Th* <all |
| CRMP1 | FALSE | FALSE | FALSE | | remainder |
| CROCCP2 | FALSE | FALSE | FALSE | | remainder |
| CRTC1 | FALSE | FALSE | TRUE | | Th* <all |
| CRY1 | TRUE | FALSE | FALSE | Th* intermediate | |
| CSF2RB | TRUE | FALSE | FALSE | Th* ~Th1 | |
| CSGALNACT1 | TRUE | FALSE | FALSE | Th* ~Th1 | |
| CST7 | TRUE | FALSE | FALSE | Th* intermediate | |
| CTDNEP1 | FALSE | FALSE | FALSE | | remainder |
| CTLA4 | TRUE | FALSE | TRUE | Th* ~Th1 | Th* <all |
| CTNNBIP1 | FALSE | FALSE | FALSE | | remainder |
| CTPS2 | FALSE | FALSE | FALSE | | remainder |
| CTSH | TRUE | FALSE | FALSE | Th* ~Th17 | |
| CTSL1 | FALSE | FALSE | FALSE | | remainder |
| CTSW | TRUE | FALSE | FALSE | Th* intermediate | |
| CTTNBP2NL | FALSE | FALSE | FALSE | | remainder |
| CUBN | FALSE | FALSE | FALSE | | remainder |
| CUX1 | FALSE | FALSE | FALSE | | remainder |
| CXCR3 | TRUE | FALSE | FALSE | Th* ~Th1 | |
| CXCR6 | FALSE | TRUE | FALSE | | Th* >all |
| CYB561 | FALSE | FALSE | FALSE | | remainder |
| CYBA | FALSE | FALSE | TRUE | | Th* <all |
| CYBRD1 | FALSE | FALSE | FALSE | | remainder |
| CYFIP1 | FALSE | TRUE | FALSE | | Th* >all |
| CYP24A1 | FALSE | FALSE | FALSE | | remainder |
| CYP2E1 | FALSE | TRUE | FALSE | | Th* >all |
| CYP4F12 | FALSE | FALSE | FALSE | | remainder |
| CYSLTR1 | FALSE | FALSE | TRUE | | Th* <all |
| CYSLTR2 | FALSE | FALSE | FALSE | | remainder |
| CYTH3 | FALSE | FALSE | FALSE | | remainder |
| D4S234E | FALSE | TRUE | FALSE | | Th* >all |
| DAAM1 | FALSE | FALSE | FALSE | | remainder |
| DAB1 | FALSE | TRUE | FALSE | | Th* >all |
| DAGLA | FALSE | FALSE | FALSE | | remainder |
| DBNDD1 | FALSE | FALSE | FALSE | | remainder |
| DBR1 | FALSE | FALSE | FALSE | | remainder |
| DCBLD1 | FALSE | FALSE | FALSE | | remainder |
| DCHS1 | FALSE | FALSE | FALSE | | remainder |
| DCHS2 | TRUE | FALSE | FALSE | Th* ~Th1 | |
| DCLRE1B | FALSE | FALSE | FALSE | | remainder |
| DECR2 | FALSE | FALSE | TRUE | | Th* <all |
| DENND3 | FALSE | FALSE | FALSE | | remainder |
| DENND5A | FALSE | FALSE | FALSE | | remainder |
| DFNB31 | TRUE | FALSE | FALSE | Th* intermediate | |
| DGCR10 | FALSE | FALSE | FALSE | | remainder |
| DGCR14 | FALSE | FALSE | FALSE | | remainder |
| DGKA | FALSE | FALSE | FALSE | | remainder |
| DGKZ | FALSE | FALSE | FALSE | | remainder |
| DHRS11 | FALSE | FALSE | FALSE | | remainder |
| DHRS3 | TRUE | FALSE | FALSE | Th* intermediate | |
| DIMT1 | FALSE | FALSE | FALSE | | remainder |
| DIP2B | FALSE | FALSE | FALSE | | remainder |
| DIP2C | FALSE | FALSE | TRUE | | Th* <all |
| DKFZP586I1420 | FALSE | FALSE | FALSE | | remainder |
| DKFZp779M0652 | FALSE | FALSE | FALSE | | remainder |
| DKK3 | FALSE | TRUE | FALSE | | Th* >all |
| DLG5 | FALSE | FALSE | FALSE | | remainder |
| DLGAP5 | FALSE | FALSE | FALSE | | remainder |
| DMAP1 | FALSE | FALSE | FALSE | | remainder |
| DMTF1 | FALSE | FALSE | FALSE | | remainder |
| DMWD | FALSE | FALSE | TRUE | | Th* <all |
| DNAJC1 | FALSE | FALSE | FALSE | | remainder |
| DNAJC17 | FALSE | FALSE | TRUE | | Th* <all |
| DNAJC19 | FALSE | FALSE | TRUE | | Th* <all |
| DNAJC6 | FALSE | FALSE | FALSE | | remainder |
| DNMBP | FALSE | FALSE | FALSE | | remainder |
| DOCK3 | FALSE | FALSE | FALSE | | remainder |
| DOM3Z | FALSE | FALSE | FALSE | | remainder |
| DOT1L | FALSE | FALSE | FALSE | | remainder |
| DPF3 | FALSE | FALSE | FALSE | | remainder |
| DPM3 | FALSE | FALSE | TRUE | | Th* <all |
| DPP4 | FALSE | TRUE | FALSE | | Th* >all |

TABLE 1-continued

| gene | th1 vs. th17 significant | th* up | th* down | heatmap grouping I | heatmap grouping II |
|---|---|---|---|---|---|
| DPY30 | FALSE | FALSE | FALSE | | remainder |
| DPYD | FALSE | FALSE | FALSE | | remainder |
| DRG2 | FALSE | FALSE | FALSE | | remainder |
| DRP2 | FALSE | FALSE | FALSE | | remainder |
| DSE | TRUE | FALSE | FALSE | Th* ~Th1 | |
| DST | TRUE | FALSE | FALSE | Th* ~Th17 | |
| DTHD1 | TRUE | FALSE | FALSE | Th* ~Th17 | |
| DTL | TRUE | FALSE | FALSE | Th* ~Th17 | |
| DUS3L | FALSE | FALSE | TRUE | | Th* <all |
| DUSP2 | FALSE | FALSE | FALSE | | remainder |
| DUSP4 | TRUE | FALSE | TRUE | Th* ~Th1 | Th* <all |
| DYNLL1 | FALSE | FALSE | FALSE | | remainder |
| DZIP3 | FALSE | FALSE | TRUE | | Th* <all |
| E2F2 | TRUE | FALSE | FALSE | Th* ~Th1 | |
| E2F3 | TRUE | FALSE | FALSE | Th* intermediate | |
| EBF1 | FALSE | FALSE | FALSE | | remainder |
| EDA | FALSE | FALSE | FALSE | | remainder |
| EDAR | TRUE | FALSE | FALSE | Th* intermediate | |
| EDF1 | FALSE | FALSE | TRUE | | Th* <all |
| EDN1 | FALSE | TRUE | FALSE | | Th* >all |
| EED | FALSE | FALSE | FALSE | | remainder |
| EEF1DP3 | TRUE | FALSE | FALSE | Th* ~Th1 | |
| EEPD1 | TRUE | FALSE | FALSE | Th* intermediate | |
| EGR2 | FALSE | FALSE | FALSE | | remainder |
| EGR3 | FALSE | FALSE | TRUE | | Th* <all |
| EHBP1 | FALSE | FALSE | FALSE | | remainder |
| EHBP1L1 | FALSE | FALSE | FALSE | | remainder |
| EHD4 | TRUE | FALSE | FALSE | Th* intermediate | |
| EIF2B5 | FALSE | FALSE | FALSE | | remainder |
| EIF2C4 | FALSE | FALSE | FALSE | | remainder |
| EIF3I | FALSE | FALSE | FALSE | | remainder |
| ELK3 | TRUE | FALSE | FALSE | Th* intermediate | |
| ELOVL4 | TRUE | TRUE | FALSE | Th* ~Th17 | Th* >all |
| ELOVL6 | FALSE | TRUE | FALSE | | Th* >all |
| EML3 | FALSE | FALSE | TRUE | | Th* <all |
| EMP3 | FALSE | FALSE | FALSE | | remainder |
| EMR1 | FALSE | FALSE | FALSE | | remainder |
| EMR4P | FALSE | FALSE | TRUE | | Th* <all |
| ENC1 | TRUE | FALSE | FALSE | Th* intermediate | |
| ENG | TRUE | FALSE | FALSE | Th* intermediate | |
| ENO2 | FALSE | FALSE | FALSE | | remainder |
| ENPP1 | FALSE | TRUE | FALSE | | Th* >all |
| ENPP4 | FALSE | FALSE | FALSE | | remainder |
| ENPP5 | TRUE | FALSE | FALSE | Th* ~Th1 | |
| EOMES | TRUE | FALSE | FALSE | Th* ~Th1 | |
| EPB41L2 | FALSE | FALSE | FALSE | | remainder |
| EPB41L3 | TRUE | FALSE | FALSE | Th* ~Th17 | |
| EPB41L4A-AS1 | FALSE | TRUE | FALSE | | Th* >all |
| EPHA1 | FALSE | FALSE | FALSE | | remainder |
| EPHA4 | FALSE | FALSE | FALSE | | remainder |
| EPHB6 | FALSE | FALSE | FALSE | | remainder |
| EPS8 | FALSE | FALSE | TRUE | | Th* <all |
| ERCC5 | FALSE | FALSE | FALSE | | remainder |
| ETFDH | FALSE | FALSE | FALSE | | remainder |
| EVC | TRUE | FALSE | TRUE | Th* ~Th1 | Th* <all |
| EVC2 | TRUE | FALSE | TRUE | Th* ~Th1 | Th* <all |
| EVL | FALSE | FALSE | TRUE | | Th* <all |
| EXOSC7 | FALSE | FALSE | FALSE | | remainder |
| EXT1 | FALSE | FALSE | FALSE | | remainder |
| EZH2 | TRUE | FALSE | FALSE | Th* ~Th1 | |
| F2R | TRUE | FALSE | FALSE | Th* intermediate | |
| F5 | TRUE | FALSE | FALSE | Th* ~Th1 | |
| FAAH2 | FALSE | FALSE | TRUE | | Th* <all |
| FAM108A1 | FALSE | FALSE | TRUE | | Th* <all |
| FAM113B | FALSE | FALSE | FALSE | | remainder |
| FAM117B | FALSE | FALSE | FALSE | | remainder |
| FAM124B | TRUE | FALSE | FALSE | Th* ~Th1 | |
| FAM125B | FALSE | FALSE | FALSE | | remainder |
| FAM129A | TRUE | FALSE | FALSE | Th* ~Th1 | |
| FAM129B | FALSE | FALSE | FALSE | | remainder |
| FAM13A | FALSE | FALSE | FALSE | | remainder |
| FAM13A-AS1 | FALSE | FALSE | TRUE | | Th* <all |
| FAM169A | FALSE | FALSE | FALSE | | remainder |
| FAM179A | FALSE | FALSE | TRUE | | Th* <all |
| FAM195B | FALSE | FALSE | TRUE | | Th* <all |
| FAM209B | FALSE | TRUE | FALSE | | Th* >all |

TABLE 1-continued

| gene | th1 vs. th17 significant | th* up | th* down | heatmap grouping I | heatmap grouping II |
|---|---|---|---|---|---|
| FAM26F | FALSE | TRUE | FALSE | | Th* >all |
| FAM49A | TRUE | FALSE | FALSE | Th* ~Th17 | |
| FAM50B | FALSE | TRUE | FALSE | | Th* >all |
| FAM53B | FALSE | FALSE | FALSE | | remainder |
| FAM65A | FALSE | FALSE | FALSE | | remainder |
| FANCI | FALSE | FALSE | FALSE | | remainder |
| FANK1 | TRUE | FALSE | TRUE | Th* ~Th1 | Th* <all |
| FARS2 | FALSE | FALSE | FALSE | | remainder |
| FAS | FALSE | FALSE | FALSE | | remainder |
| FBLN5 | FALSE | FALSE | FALSE | | remainder |
| FBP1 | TRUE | FALSE | FALSE | Th* intermediate | |
| FBXL14 | FALSE | FALSE | FALSE | | remainder |
| FBXO10 | FALSE | FALSE | TRUE | | Th* <all |
| FBXW5 | FALSE | FALSE | TRUE | | Th* <all |
| FCER1G | FALSE | TRUE | FALSE | | Th* >all |
| FCHO2 | FALSE | FALSE | FALSE | | remainder |
| FCRL3 | FALSE | FALSE | TRUE | | Th* <all |
| FCRL6 | TRUE | FALSE | FALSE | Th* intermediate | |
| FGD2 | FALSE | TRUE | FALSE | | Th* >all |
| FGF9 | FALSE | TRUE | FALSE | | Th* >all |
| FGFBP2 | FALSE | FALSE | FALSE | | remainder |
| FGFR1 | FALSE | FALSE | FALSE | | remainder |
| FGFR2 | FALSE | FALSE | FALSE | | remainder |
| FHIT | FALSE | FALSE | TRUE | | Th* <all |
| FHL1 | FALSE | FALSE | FALSE | | remainder |
| FILIP1L | FALSE | TRUE | FALSE | | Th* >all |
| FIS1 | FALSE | FALSE | FALSE | | remainder |
| FKBP11 | FALSE | FALSE | FALSE | | remainder |
| FKBP8 | FALSE | FALSE | TRUE | | Th* <all |
| FLJ10038 | FALSE | FALSE | FALSE | | remainder |
| FLJ21408 | FALSE | FALSE | FALSE | | remainder |
| FLJ45513 | FALSE | FALSE | TRUE | | Th* <all |
| FLJ45983 | FALSE | FALSE | FALSE | | remainder |
| FLNA | FALSE | FALSE | FALSE | | remainder |
| FLNB | FALSE | FALSE | FALSE | | remainder |
| FLT4 | TRUE | FALSE | FALSE | Th* intermediate | |
| FN3K | FALSE | FALSE | FALSE | | remainder |
| FNBP1L | TRUE | FALSE | FALSE | Th* intermediate | |
| FNDC3B | FALSE | FALSE | FALSE | | remainder |
| FNIP2 | FALSE | FALSE | FALSE | | remainder |
| FOXD2 | FALSE | FALSE | TRUE | | Th* <all |
| FOXM1 | FALSE | FALSE | TRUE | | Th* <all |
| FOXP3 | TRUE | FALSE | FALSE | Th* ~Th1 | |
| FOXP4 | FALSE | FALSE | FALSE | | remainder |
| FRG1 | FALSE | FALSE | FALSE | | remainder |
| FRMD8 | FALSE | TRUE | FALSE | | Th* >all |
| FRY | TRUE | FALSE | FALSE | Th* ~Th17 | |
| FUBP3 | FALSE | FALSE | FALSE | | remainder |
| FURIN | TRUE | FALSE | FALSE | Th* ~Th17 | |
| FUT7 | TRUE | FALSE | FALSE | Th* intermediate | |
| FXYD5 | FALSE | FALSE | FALSE | | remainder |
| FYCO1 | FALSE | FALSE | FALSE | | remainder |
| FZD8 | FALSE | TRUE | TRUE | | Th* >all |
| GAB1 | TRUE | TRUE | FALSE | Th* ~Th17 | Th* >all |
| GAB2 | FALSE | FALSE | FALSE | | remainder |
| GAB3 | FALSE | FALSE | FALSE | | remainder |
| GABARAPL2 | FALSE | FALSE | FALSE | | remainder |
| GABBR1 | TRUE | FALSE | FALSE | Th* intermediate | |
| GADD45GIP1 | FALSE | FALSE | FALSE | | remainder |
| GALC | FALSE | FALSE | FALSE | | remainder |
| GALNT10 | FALSE | FALSE | FALSE | | remainder |
| GALT | FALSE | FALSE | FALSE | | remainder |
| GAPDH | FALSE | FALSE | FALSE | | remainder |
| GAS6 | FALSE | FALSE | TRUE | | Th* <all |
| GAS7 | FALSE | FALSE | FALSE | | remainder |
| GATA3 | FALSE | FALSE | FALSE | | remainder |
| GBGT1 | FALSE | FALSE | FALSE | | remainder |
| GBP4 | TRUE | FALSE | FALSE | Th* intermediate | |
| GBP5 | TRUE | FALSE | FALSE | Th* ~Th1 | |
| GCET2 | FALSE | FALSE | FALSE | | remainder |
| GCH1 | FALSE | FALSE | FALSE | | remainder |
| GCNT1 | FALSE | FALSE | FALSE | | remainder |
| GCNT4 | FALSE | FALSE | TRUE | | Th* <all |
| GDPD5 | FALSE | FALSE | FALSE | | remainder |
| GFI1 | TRUE | FALSE | FALSE | Th* ~Th1 | |
| GHDC | FALSE | FALSE | FALSE | | remainder |
| GIMAP2 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| GINS2 | FALSE | FALSE | TRUE | | Th* <all |
| GLB1 | FALSE | FALSE | FALSE | | remainder |
| GLI4 | FALSE | FALSE | TRUE | | Th* <all |
| GLIPR1 | TRUE | FALSE | FALSE | Th* ~Th1 | |
| GLOD4 | FALSE | FALSE | FALSE | | remainder |
| GLRX2 | FALSE | TRUE | TRUE | | Th* >all |
| GLUL | TRUE | FALSE | FALSE | Th* intermediate | |
| GMNN | FALSE | FALSE | TRUE | | Th* <all |
| GNA15 | TRUE | FALSE | FALSE | Th* intermediate | |
| GNB2 | FALSE | FALSE | FALSE | | remainder |
| GNG4 | FALSE | FALSE | TRUE | | Th* <all |
| GNGT2 | TRUE | FALSE | FALSE | Th* ~Th1 | |
| GNLY | TRUE | FALSE | FALSE | Th* intermediate | |
| GNRH1 | FALSE | FALSE | TRUE | | Th* <all |
| GOLGA6L5 | FALSE | TRUE | FALSE | | Th* >all |
| GOLGA7B | FALSE | FALSE | FALSE | | remainder |
| GOT2 | FALSE | FALSE | FALSE | | remainder |
| GPA33 | FALSE | FALSE | TRUE | | Th* <all |
| GPC3 | TRUE | FALSE | FALSE | Th* ~Th1 | |
| GPD1L | FALSE | FALSE | FALSE | | remainder |
| GPR114 | FALSE | FALSE | FALSE | | remainder |
| GPR146 | TRUE | FALSE | FALSE | Th* intermediate | |
| GPR15 | TRUE | FALSE | TRUE | Th* ~Th1 | Th* <all |
| GPR160 | FALSE | TRUE | FALSE | | Th* >all |
| GPR172A | FALSE | FALSE | TRUE | | Th* <all |
| GPR56 | TRUE | FALSE | FALSE | Th* intermediate | |
| GPR75 | FALSE | FALSE | FALSE | | remainder |
| GPS1 | FALSE | FALSE | FALSE | | remainder |
| GPX1 | TRUE | FALSE | FALSE | Th* ~Th17 | |
| GPX4 | FALSE | FALSE | FALSE | | remainder |
| GRAPL | FALSE | FALSE | TRUE | | Th* <all |
| GREM2 | FALSE | TRUE | FALSE | | Th* >all |
| GRHL2 | FALSE | TRUE | FALSE | | Th* >all |
| GRHPR | FALSE | FALSE | FALSE | | remainder |
| GRIP1 | FALSE | FALSE | FALSE | | remainder |
| GSDMD | FALSE | FALSE | TRUE | | Th* <all |
| GTF2IRD1 | TRUE | FALSE | FALSE | Th* ~Th1 | |
| GUCA1B | FALSE | FALSE | FALSE | | remainder |
| GUSBP4 | FALSE | FALSE | TRUE | | Th* <all |
| GYG1 | FALSE | FALSE | FALSE | | remainder |
| GZMA | TRUE | FALSE | FALSE | Th* ~Th1 | |
| GZMB | TRUE | FALSE | FALSE | Th* ~Th17 | |
| GZMH | TRUE | FALSE | FALSE | Th* intermediate | |
| GZMK | TRUE | FALSE | FALSE | Th* ~Th1 | |
| GZMM | TRUE | FALSE | TRUE | Th* ~Th17 | Th* <all |
| H1FX | FALSE | FALSE | FALSE | | remainder |
| H2AFZ | FALSE | FALSE | FALSE | | remainder |
| HAPLN3 | FALSE | FALSE | FALSE | | remainder |
| HAVCR1 | FALSE | FALSE | FALSE | | remainder |
| HCG18 | TRUE | FALSE | FALSE | Th* ~Th1 | |
| HCLS1 | FALSE | FALSE | TRUE | | Th* <all |
| HCST | FALSE | FALSE | TRUE | | Th* <all |
| HDAC10 | FALSE | FALSE | TRUE | | Th* <all |
| HDDC3 | FALSE | FALSE | FALSE | | remainder |
| HDHD1 | FALSE | FALSE | FALSE | | remainder |
| HDHD3 | FALSE | TRUE | FALSE | | Th* >all |
| HEATR7A | FALSE | FALSE | TRUE | | Th* <all |
| HERC6 | FALSE | FALSE | FALSE | | remainder |
| HHLA3 | FALSE | FALSE | FALSE | | remainder |
| HIF1AN | FALSE | FALSE | FALSE | | remainder |
| HINFP | FALSE | FALSE | FALSE | | remainder |
| HIP1R | FALSE | FALSE | FALSE | | remainder |
| HIVEP3 | FALSE | FALSE | FALSE | | remainder |
| HK1 | FALSE | FALSE | FALSE | | remainder |
| HLA-DOA | TRUE | FALSE | FALSE | Th* ~Th1 | |
| HLA-DQB1 | TRUE | FALSE | FALSE | Th* ~Th1 | |
| HLF | TRUE | FALSE | FALSE | Th* intermediate | |
| HN1 | TRUE | FALSE | FALSE | Th* intermediate | |
| HNF1A | FALSE | FALSE | FALSE | | remainder |
| HNRNPA0 | FALSE | FALSE | FALSE | | remainder |
| HNRNPA1 | FALSE | TRUE | FALSE | | Th* >all |
| HOMER1 | FALSE | TRUE | FALSE | | Th* >all |
| HOPX | TRUE | FALSE | FALSE | Th* ~Th1 | |
| HPCAL1 | FALSE | FALSE | FALSE | | remainder |
| HPGD | TRUE | FALSE | FALSE | Th* intermediate | |
| HPGDS | FALSE | FALSE | FALSE | | remainder |
| HPS6 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| HPX | FALSE | FALSE | FALSE | | remainder |
| HRH2 | FALSE | FALSE | TRUE | | Th* <all |
| HRH4 | TRUE | FALSE | FALSE | Th* intermediate | |
| HSBP1L1 | FALSE | FALSE | FALSE | | remainder |
| HSD17B7P2 | FALSE | TRUE | FALSE | | Th* >all |
| HSD17B8 | FALSE | FALSE | FALSE | | remainder |
| HSF4 | TRUE | FALSE | FALSE | Th* intermediate | |
| HSPB1 | FALSE | FALSE | TRUE | | Th* <all |
| HSPE1 | FALSE | TRUE | FALSE | | Th* >all |
| HTR2B | FALSE | FALSE | TRUE | | Th* <all |
| HVCN1 | FALSE | FALSE | FALSE | | remainder |
| ICAM2 | FALSE | FALSE | FALSE | | remainder |
| ICOS | FALSE | FALSE | FALSE | | remainder |
| ID2 | TRUE | FALSE | FALSE | Th* ~Th1 | |
| ID3 | FALSE | FALSE | TRUE | | Th* <all |
| IDH2 | FALSE | FALSE | FALSE | | remainder |
| IDH3B | FALSE | FALSE | FALSE | | remainder |
| IER5 | FALSE | TRUE | FALSE | | Th* >all |
| IFI27 | TRUE | FALSE | FALSE | Th* ~Th17 | |
| IFI30 | FALSE | FALSE | FALSE | | remainder |
| IFI44 | FALSE | FALSE | FALSE | | remainder |
| IFI44L | FALSE | TRUE | FALSE | | Th* >all |
| IFI6 | FALSE | FALSE | FALSE | | remainder |
| IFNG | TRUE | FALSE | FALSE | Th* ~Th1 | |
| IFNGR2 | TRUE | FALSE | FALSE | Th* intermediate | |
| IGF1R | TRUE | FALSE | FALSE | Th* intermediate | |
| IGFBP3 | TRUE | FALSE | FALSE | Th* ~Th1 | |
| IGFBP4 | FALSE | FALSE | FALSE | | remainder |
| IGSF9B | TRUE | FALSE | TRUE | Th* ~Th1 | Th* <all |
| IKBKB | FALSE | FALSE | FALSE | | remainder |
| IKBKE | FALSE | FALSE | FALSE | | remainder |
| IKZF2 | TRUE | FALSE | FALSE | Th* ~Th1 | |
| IKZF3 | FALSE | FALSE | FALSE | | remainder |
| IL10RB | FALSE | FALSE | TRUE | | Th* <all |
| IL12RB2 | TRUE | TRUE | FALSE | Th* ~Th1 | Th* >all |
| IL15 | FALSE | FALSE | FALSE | | remainder |
| IL17RB | TRUE | FALSE | FALSE | Th* intermediate | |
| IL17RE | TRUE | FALSE | FALSE | Th* intermediate | |
| IL18R1 | FALSE | TRUE | FALSE | | Th* >all |
| IL18RAP | TRUE | TRUE | FALSE | Th* ~Th1 | Th* >all |
| IL1R1 | TRUE | FALSE | FALSE | Th* intermediate | |
| IL1RL1 | FALSE | TRUE | FALSE | | Th* >all |
| IL2 | FALSE | FALSE | FALSE | | remainder |
| IL23A | FALSE | FALSE | FALSE | | remainder |
| IL23R | FALSE | TRUE | FALSE | | Th* >all |
| IL2RA | TRUE | FALSE | FALSE | Th* intermediate | |
| IL32 | FALSE | TRUE | FALSE | | Th* >all |
| IL4I1 | TRUE | FALSE | FALSE | Th* ~Th17 | |
| IL4R | FALSE | FALSE | FALSE | | remainder |
| IL5RA | FALSE | FALSE | FALSE | | remainder |
| IL6R | FALSE | FALSE | FALSE | | remainder |
| IL6ST | FALSE | FALSE | FALSE | | remainder |
| ILK | FALSE | FALSE | FALSE | | remainder |
| IMMP2L | FALSE | TRUE | FALSE | | Th* >all |
| IMP4 | FALSE | FALSE | FALSE | | remainder |
| IMPA2 | FALSE | FALSE | TRUE | | Th* <all |
| INCENP | FALSE | FALSE | FALSE | | remainder |
| INF2 | FALSE | FALSE | TRUE | | Th* <all |
| INPP5F | FALSE | FALSE | TRUE | | Th* <all |
| INTS1 | FALSE | FALSE | TRUE | | Th* <all |
| INVS | FALSE | FALSE | FALSE | | remainder |
| IPP | FALSE | FALSE | FALSE | | remainder |
| IRF2BPL | FALSE | FALSE | FALSE | | remainder |
| IRF4 | FALSE | FALSE | TRUE | | Th* <all |
| IRF8 | FALSE | FALSE | FALSE | | remainder |
| IRS2 | FALSE | FALSE | FALSE | | remainder |
| ISG15 | FALSE | FALSE | TRUE | | Th* <all |
| ISM1 | FALSE | FALSE | FALSE | | remainder |
| ISOC1 | FALSE | TRUE | FALSE | | Th* >all |
| ISYNA1 | FALSE | FALSE | TRUE | | Th* <all |
| ITFG3 | FALSE | FALSE | TRUE | | Th* <all |
| ITGA1 | TRUE | FALSE | FALSE | Th* ~Th1 | |
| ITGA4 | TRUE | FALSE | FALSE | Th* ~Th1 | |
| ITGAE | FALSE | FALSE | FALSE | | remainder |
| ITGAM | TRUE | FALSE | TRUE | Th* ~Th17 | Th* <all |
| ITGB1BP1 | FALSE | TRUE | FALSE | | Th* >all |
| ITGB3BP | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| ITGB7 | FALSE | FALSE | FALSE | | remainder |
| ITIH4 | FALSE | FALSE | FALSE | | remainder |
| ITM2C | FALSE | FALSE | FALSE | | remainder |
| ITPK1 | FALSE | FALSE | FALSE | | remainder |
| ITPRIP | FALSE | FALSE | FALSE | | remainder |
| ITPRIPL1 | FALSE | FALSE | FALSE | | remainder |
| JAK2 | FALSE | FALSE | FALSE | | remainder |
| JAKMIP1 | TRUE | FALSE | FALSE | Th* ~Th17 | |
| JAKMIP2 | FALSE | FALSE | FALSE | | remainder |
| JUNB | FALSE | FALSE | TRUE | | Th* <all |
| JUND | FALSE | FALSE | FALSE | | remainder |
| KALRN | FALSE | FALSE | TRUE | | Th* <all |
| KANK1 | TRUE | FALSE | TRUE | Th* ~Th1 | Th* <all |
| KATNAL1 | TRUE | FALSE | FALSE | Th* ~Th1 | |
| KCNA6 | TRUE | FALSE | FALSE | Th* ~Th1 | |
| KCNC3 | FALSE | FALSE | FALSE | | remainder |
| KCNH2 | FALSE | FALSE | FALSE | | remainder |
| KCNN4 | TRUE | FALSE | FALSE | Th* ~Th17 | |
| KCNQ1OT1 | FALSE | FALSE | TRUE | | Th* <all |
| KCNQ3 | FALSE | TRUE | FALSE | | Th* >all |
| KCNQ5 | TRUE | FALSE | FALSE | Th* intermediate | |
| KCTD15 | FALSE | FALSE | FALSE | | remainder |
| KDM6B | FALSE | FALSE | FALSE | | remainder |
| KDSR | FALSE | FALSE | FALSE | | remainder |
| KHSRP | FALSE | FALSE | FALSE | | remainder |
| KIAA0101 | FALSE | FALSE | TRUE | | Th* <all |
| KIAA0182 | TRUE | FALSE | FALSE | Th* intermediate | |
| KIAA0556 | FALSE | FALSE | FALSE | | remainder |
| KIAA1279 | FALSE | FALSE | FALSE | | remainder |
| KIAA1328 | FALSE | FALSE | FALSE | | remainder |
| KIAA1671 | TRUE | FALSE | FALSE | Th* intermediate | |
| KIAA1683 | FALSE | FALSE | TRUE | | Th* <all |
| KIF13A | FALSE | FALSE | FALSE | | remainder |
| KIF26A | TRUE | FALSE | FALSE | Th* intermediate | |
| KIF5C | TRUE | FALSE | FALSE | Th* ~Th17 | |
| KIFC2 | TRUE | FALSE | FALSE | Th* intermediate | |
| KIT | FALSE | TRUE | FALSE | | Th* >all |
| KLF10 | FALSE | FALSE | FALSE | | remainder |
| KLF2 | FALSE | FALSE | FALSE | | remainder |
| KLF7 | FALSE | FALSE | FALSE | | remainder |
| KLF8 | TRUE | FALSE | FALSE | Th* intermediate | |
| KLHL21 | FALSE | FALSE | FALSE | | remainder |
| KLHL3 | FALSE | FALSE | FALSE | | remainder |
| KLRB1 | FALSE | FALSE | FALSE | | remainder |
| KLRG1 | TRUE | FALSE | FALSE | Th* ~Th1 | |
| KRT1 | FALSE | FALSE | TRUE | | Th* <all |
| KRT72 | TRUE | FALSE | TRUE | Th* intermediate | Th* <all |
| KRT73 | TRUE | FALSE | FALSE | Th* ~Th17 | |
| L1CAM | TRUE | FALSE | FALSE | Th* ~Th1 | |
| LAG3 | TRUE | FALSE | FALSE | Th* ~Th17 | |
| LAIR1 | TRUE | FALSE | FALSE | Th* ~Th17 | |
| LAMA2 | FALSE | TRUE | FALSE | | Th* >all |
| LAMP3 | TRUE | FALSE | FALSE | Th* intermediate | |
| LAPTM4B | FALSE | TRUE | FALSE | | Th* >all |
| LATS2 | FALSE | TRUE | FALSE | | Th* >all |
| LBH | FALSE | FALSE | FALSE | | remainder |
| LCMT2 | FALSE | FALSE | TRUE | | Th* <all |
| LEF1 | FALSE | FALSE | FALSE | | remainder |
| LENG1 | FALSE | FALSE | FALSE | | remainder |
| LENG8 | FALSE | FALSE | FALSE | | remainder |
| LFNG | FALSE | FALSE | FALSE | | remainder |
| LGALS1 | TRUE | FALSE | FALSE | Th* ~Th1 | |
| LGALS3 | TRUE | FALSE | FALSE | Th* intermediate | |
| LGALS9 | FALSE | FALSE | FALSE | | remainder |
| LGR6 | TRUE | FALSE | FALSE | Th* ~Th17 | |
| LIMA1 | FALSE | FALSE | FALSE | | remainder |
| LIMD2 | FALSE | FALSE | TRUE | | Th* <all |
| LIME1 | FALSE | FALSE | TRUE | | Th* <all |
| LIMS2 | FALSE | FALSE | FALSE | | remainder |
| LIN28A | FALSE | FALSE | TRUE | | Th* <all |
| LINC00173 | FALSE | FALSE | TRUE | | Th* <all |
| LINC00299 | TRUE | FALSE | FALSE | Th* ~Th17 | |
| LINC00341 | FALSE | FALSE | FALSE | | remainder |
| LINC00426 | FALSE | FALSE | FALSE | | remainder |
| LINC00511 | FALSE | FALSE | FALSE | | remainder |
| LINC00526 | FALSE | TRUE | FALSE | | Th* >all |
| LINGO4 | TRUE | FALSE | FALSE | Th* ~Th17 | |

TABLE 1-continued

| gene | th1 vs. th17 significant | th* up | th* down | heatmap grouping I | heatmap grouping II |
|---|---|---|---|---|---|
| LIX1L | FALSE | FALSE | FALSE | | remainder |
| LMF1 | FALSE | FALSE | FALSE | | remainder |
| LMF2 | FALSE | FALSE | FALSE | | remainder |
| LMNA | TRUE | FALSE | FALSE | Th* intermediate | |
| LMO4 | TRUE | FALSE | FALSE | Th* intermediate | |
| LOC100128420 | FALSE | FALSE | FALSE | | remainder |
| LOC100129034 | FALSE | FALSE | FALSE | | remainder |
| LOC100131176 | TRUE | FALSE | FALSE | Th* intermediate | |
| LOC100132077 | FALSE | TRUE | FALSE | | Th* >all |
| LOC100132891 | TRUE | FALSE | FALSE | Th* intermediate | |
| LOC100288123 | FALSE | FALSE | TRUE | | Th* <all |
| LOC100499405 | TRUE | FALSE | FALSE | Th* ~Th1 | |
| LOC100499467 | FALSE | FALSE | FALSE | | remainder |
| LOC100499489 | FALSE | TRUE | FALSE | | Th* >all |
| LOC100505483 | FALSE | FALSE | FALSE | | remainder |
| LOC100505648 | FALSE | FALSE | FALSE | | remainder |
| LOC100505696 | FALSE | FALSE | FALSE | | remainder |
| LOC100505738 | FALSE | FALSE | FALSE | | remainder |
| LOC100505746 | FALSE | FALSE | TRUE | | Th* <all |
| LOC100505806 | FALSE | FALSE | FALSE | | remainder |
| LOC100505839 | FALSE | FALSE | FALSE | | remainder |
| LOC100506776 | FALSE | FALSE | FALSE | | remainder |
| LOC100506801 | TRUE | FALSE | FALSE | Th* ~Th1 | |
| LOC100506804 | FALSE | FALSE | FALSE | | remainder |
| LOC100506866 | FALSE | FALSE | TRUE | | Th* <all |
| LOC100507050 | TRUE | FALSE | FALSE | Th* ~Th1 | |
| LOC100507421 | FALSE | TRUE | FALSE | | Th* >all |
| LOC100507582 | FALSE | FALSE | FALSE | | remainder |
| LOC100652846 | TRUE | FALSE | FALSE | Th* ~Th1 | |
| LOC144571 | TRUE | FALSE | FALSE | Th* intermediate | |
| LOC145474 | FALSE | TRUE | TRUE | | Th* >all |
| LOC148696 | FALSE | FALSE | TRUE | | Th* <all |
| LOC220729 | FALSE | FALSE | TRUE | | Th* <all |
| LOC254100 | FALSE | FALSE | TRUE | | Th* <all |
| LOC256021 | TRUE | FALSE | FALSE | Th* intermediate | |
| LOC283174 | TRUE | FALSE | FALSE | Th* ~Th17 | |
| LOC284385 | FALSE | FALSE | FALSE | | remainder |
| LOC285074 | FALSE | FALSE | FALSE | | remainder |
| LOC285740 | TRUE | FALSE | FALSE | Th* intermediate | |
| LOC338799 | FALSE | FALSE | TRUE | | Th* <all |
| LOC339894 | FALSE | FALSE | FALSE | | remainder |
| LOC348761 | FALSE | FALSE | TRUE | | Th* <all |
| LOC388152 | FALSE | FALSE | FALSE | | remainder |
| LOC388796 | FALSE | FALSE | FALSE | | remainder |
| LOC541471 | FALSE | FALSE | TRUE | | Th* <all |
| LOC613037 | FALSE | FALSE | FALSE | | remainder |
| LOC619207 | FALSE | FALSE | FALSE | | remainder |
| LOC643529 | FALSE | TRUE | FALSE | | Th* >all |
| LOC646329 | TRUE | FALSE | FALSE | Th* ~Th1 | |
| LOC653075 | FALSE | FALSE | FALSE | | remainder |
| LOC653160 | FALSE | FALSE | FALSE | | remainder |
| LOC728875 | FALSE | FALSE | FALSE | | remainder |
| LOC729041 | FALSE | TRUE | FALSE | | Th* >all |
| LOC90834 | FALSE | FALSE | FALSE | | remainder |
| LOC93622 | FALSE | TRUE | FALSE | | Th* >all |
| LONRF1 | FALSE | FALSE | FALSE | | remainder |
| LONRF2 | TRUE | FALSE | FALSE | Th* ~Th1 | |
| LOXL1 | TRUE | FALSE | TRUE | Th* ~Th1 | Th* <all |
| LPAR2 | FALSE | FALSE | FALSE | | remainder |
| LPAR3 | FALSE | TRUE | FALSE | | Th* >all |
| LPAR5 | FALSE | FALSE | TRUE | | Th* <all |
| LPAR6 | TRUE | FALSE | FALSE | Th* ~Th1 | |
| LRCH3 | FALSE | FALSE | FALSE | | remainder |
| LRFN1 | FALSE | FALSE | FALSE | | remainder |
| LRP12 | TRUE | FALSE | FALSE | Th* ~Th17 | |
| LRP5L | FALSE | FALSE | FALSE | | remainder |
| LRRC16B | FALSE | TRUE | FALSE | | Th* >all |
| LRRC32 | TRUE | FALSE | FALSE | Th* ~Th1 | |
| LRRC33 | TRUE | FALSE | FALSE | Th* ~Th1 | |
| LRRC6 | FALSE | FALSE | FALSE | | remainder |
| LRRC8D | FALSE | FALSE | FALSE | | remainder |
| LRRTM2 | FALSE | TRUE | FALSE | | Th* >all |
| LSM1 | FALSE | FALSE | FALSE | | remainder |
| LSM5 | FALSE | TRUE | FALSE | | Th* >all |
| LST1 | TRUE | FALSE | FALSE | Th* ~Th17 | |
| LTB | FALSE | TRUE | FALSE | | Th* >all |
| LTBP3 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| LTK | TRUE | FALSE | FALSE | Th* ~Th17 | |
| LUZP1 | TRUE | FALSE | FALSE | Th* ~Th1 | |
| LY6E | FALSE | FALSE | TRUE | | Th* <all |
| LY6G5B | FALSE | FALSE | TRUE | | Th* <all |
| LYAR | TRUE | FALSE | FALSE | Th* ~Th1 | |
| LYPD3 | FALSE | FALSE | TRUE | | Th* <all |
| LYSMD2 | FALSE | FALSE | FALSE | | remainder |
| LZTFL1 | FALSE | TRUE | FALSE | | Th* >all |
| LZTS2 | FALSE | FALSE | TRUE | | Th* <all |
| MAF | TRUE | FALSE | FALSE | Th* ~Th1 | |
| MAGOH | FALSE | FALSE | FALSE | | remainder |
| MAN1A1 | FALSE | TRUE | FALSE | | Th* >all |
| MAN1B1 | FALSE | FALSE | TRUE | | Th* <all |
| MAN2A1 | FALSE | FALSE | FALSE | | remainder |
| MAP1S | FALSE | FALSE | TRUE | | Th* <all |
| MAP2K2 | FALSE | FALSE | TRUE | | Th* <all |
| MAP3K4 | TRUE | FALSE | FALSE | Th* intermediate | |
| MAP3K8 | FALSE | FALSE | FALSE | | remainder |
| MAPK11 | FALSE | FALSE | FALSE | | remainder |
| MAPK3 | FALSE | FALSE | TRUE | | Th* <all |
| MAPKBP1 | FALSE | FALSE | FALSE | | remainder |
| MAPRE3 | FALSE | FALSE | FALSE | | remainder |
| MARCKSL1 | FALSE | FALSE | FALSE | | remainder |
| MARS | FALSE | FALSE | FALSE | | remainder |
| MAST4 | FALSE | FALSE | FALSE | | remainder |
| MATL2963 | FALSE | FALSE | FALSE | | remainder |
| MATN2 | TRUE | FALSE | FALSE | Th* ~Th17 | |
| MBD3 | FALSE | FALSE | FALSE | | remainder |
| MBD6 | FALSE | FALSE | FALSE | | remainder |
| MCAM | TRUE | FALSE | FALSE | Th* ~Th17 | |
| MCART6 | TRUE | FALSE | FALSE | Th* ~Th17 | |
| MCF2L2 | TRUE | FALSE | FALSE | Th* intermediate | |
| MCOLN2 | TRUE | FALSE | FALSE | Th* ~Th1 | |
| MCRS1 | FALSE | FALSE | FALSE | | remainder |
| MCTP2 | TRUE | FALSE | FALSE | Th* ~Th1 | |
| MDS2 | FALSE | FALSE | FALSE | | remainder |
| ME1 | FALSE | TRUE | FALSE | | Th* >all |
| ME3 | TRUE | FALSE | FALSE | Th* ~Th1 | |
| MED15 | FALSE | FALSE | FALSE | | remainder |
| MED16 | FALSE | FALSE | TRUE | | Th* <all |
| MED22 | FALSE | FALSE | TRUE | | Th* <all |
| MEOX1 | FALSE | FALSE | TRUE | | Th* <all |
| MESDC1 | FALSE | TRUE | FALSE | | Th* >all |
| METTL21A | FALSE | FALSE | FALSE | | remainder |
| METTL21B | FALSE | FALSE | FALSE | | remainder |
| MFHAS1 | FALSE | FALSE | FALSE | | remainder |
| MGC12982 | FALSE | FALSE | FALSE | | remainder |
| MGLL | TRUE | FALSE | FALSE | Th* intermediate | |
| MIA | FALSE | TRUE | FALSE | | Th* >all |
| MIAT | FALSE | FALSE | TRUE | | Th* <all |
| MICAL2 | TRUE | FALSE | FALSE | Th* intermediate | |
| MICALCL | TRUE | FALSE | FALSE | Th* intermediate | |
| MID1IP1 | FALSE | FALSE | FALSE | | remainder |
| MIDN | FALSE | FALSE | FALSE | | remainder |
| MIR221 | FALSE | FALSE | TRUE | | Th* <all |
| MIR22HG | TRUE | FALSE | FALSE | Th* intermediate | |
| MIR31HG | FALSE | TRUE | FALSE | | Th* >all |
| MIR3916 | FALSE | TRUE | FALSE | | Th* >all |
| MIR4298 | FALSE | TRUE | FALSE | | Th* >all |
| MIR4440 | FALSE | FALSE | FALSE | | remainder |
| MKI67 | FALSE | FALSE | TRUE | | Th* <all |
| MKL2 | FALSE | FALSE | FALSE | | remainder |
| MLF1 | FALSE | FALSE | TRUE | | Th* <all |
| MLL2 | FALSE | FALSE | FALSE | | remainder |
| MLLT3 | FALSE | FALSE | FALSE | | remainder |
| MLLT4 | FALSE | FALSE | FALSE | | remainder |
| MMP24 | FALSE | FALSE | FALSE | | remainder |
| MNF1 | FALSE | FALSE | FALSE | | remainder |
| MOB2 | FALSE | FALSE | TRUE | | Th* <all |
| MOB3C | FALSE | FALSE | FALSE | | remainder |
| MORC2 | FALSE | FALSE | FALSE | | remainder |
| MORC4 | FALSE | FALSE | FALSE | | remainder |
| MOSPD2 | FALSE | FALSE | FALSE | | remainder |
| MPPE1 | FALSE | FALSE | TRUE | | Th* <all |
| MPV17 | FALSE | FALSE | FALSE | | remainder |
| MRC2 | TRUE | FALSE | TRUE | Th* ~Th1 | Th* <all |
| MRP63 | FALSE | FALSE | TRUE | | Th* <all |

TABLE 1-continued

| gene | th1 vs. th17 significant | th* up | th* down | heatmap grouping I | heatmap grouping II |
|---|---|---|---|---|---|
| MRPL10 | FALSE | FALSE | FALSE | | remainder |
| MRPL23 | FALSE | FALSE | TRUE | | Th* <all |
| MRPL34 | FALSE | FALSE | FALSE | | remainder |
| MRPL41 | TRUE | FALSE | FALSE | Th* ~Th1 | |
| MRS2P2 | FALSE | FALSE | FALSE | | remainder |
| MS4A1 | TRUE | FALSE | TRUE | Th* intermediate | Th* <all |
| MSH2 | FALSE | FALSE | FALSE | | remainder |
| MTSS1 | FALSE | FALSE | FALSE | | remainder |
| MTUS1 | FALSE | FALSE | FALSE | | remainder |
| MTUS2 | FALSE | TRUE | FALSE | | Th* >all |
| MUC16 | FALSE | FALSE | FALSE | | remainder |
| MVP | FALSE | FALSE | FALSE | | remainder |
| MXD4 | FALSE | FALSE | FALSE | | remainder |
| MYB | FALSE | FALSE | TRUE | | Th* <all |
| MYBL1 | FALSE | FALSE | FALSE | | remainder |
| MYLIP | FALSE | FALSE | FALSE | | remainder |
| MYO15B | FALSE | FALSE | FALSE | | remainder |
| MYO16 | FALSE | FALSE | TRUE | | Th* <all |
| MYO18A | FALSE | FALSE | FALSE | | remainder |
| MYO1G | FALSE | FALSE | FALSE | | remainder |
| MYO7A | TRUE | FALSE | FALSE | Th* ~Th1 | |
| MZT2A | FALSE | FALSE | TRUE | | Th* <all |
| NACA2 | FALSE | TRUE | FALSE | | Th* >all |
| NAF1 | FALSE | FALSE | FALSE | | remainder |
| NAP1L3 | FALSE | FALSE | FALSE | | remainder |
| NBEA | FALSE | FALSE | FALSE | | remainder |
| NBEAL2 | FALSE | FALSE | FALSE | | remainder |
| NBPF15 | FALSE | FALSE | FALSE | | remainder |
| NBPF9 | FALSE | FALSE | FALSE | | remainder |
| NCALD | TRUE | FALSE | FALSE | Th* ~Th1 | |
| NCAPG2 | FALSE | TRUE | FALSE | | Th* >all |
| NCAPH | TRUE | FALSE | FALSE | Th* ~Th1 | |
| NCF4 | FALSE | FALSE | FALSE | | remainder |
| NCKAP1 | FALSE | FALSE | TRUE | | Th* <all |
| NDFIP2 | FALSE | FALSE | TRUE | | Th* <all |
| NDUFA11 | FALSE | FALSE | TRUE | | Th* <all |
| NDUFA13 | FALSE | FALSE | TRUE | | Th* <all |
| NDUFA3 | FALSE | FALSE | TRUE | | Th* <all |
| NDUFB3 | FALSE | FALSE | FALSE | | remainder |
| NDUFB7 | FALSE | FALSE | TRUE | | Th* <all |
| NDUFC1 | FALSE | FALSE | FALSE | | remainder |
| NDUFS7 | FALSE | FALSE | TRUE | | Th* <all |
| NDUFV3 | FALSE | FALSE | FALSE | | remainder |
| NEDD4L | TRUE | FALSE | FALSE | Th* ~Th1 | |
| NEFL | TRUE | FALSE | FALSE | Th* intermediate | |
| NEK6 | FALSE | FALSE | FALSE | | remainder |
| NELF | TRUE | FALSE | TRUE | Th* ~Th1 | Th* <all |
| NELL2 | FALSE | FALSE | FALSE | | remainder |
| NENF | FALSE | FALSE | FALSE | | remainder |
| NEO1 | FALSE | FALSE | FALSE | | remainder |
| NET1 | FALSE | FALSE | FALSE | | remainder |
| NEURL4 | FALSE | FALSE | FALSE | | remainder |
| NFATC2 | FALSE | FALSE | FALSE | | remainder |
| NFIC | FALSE | FALSE | FALSE | | remainder |
| NGDN | FALSE | FALSE | FALSE | | remainder |
| NHLRC3 | FALSE | FALSE | TRUE | | Th* <all |
| NHSL2 | FALSE | FALSE | FALSE | | remainder |
| NINJ2 | FALSE | FALSE | TRUE | | Th* <all |
| NIPAL2 | FALSE | FALSE | TRUE | | Th* <all |
| NIT2 | FALSE | TRUE | FALSE | | Th* >all |
| NKG7 | TRUE | FALSE | FALSE | Th* ~Th1 | |
| NLRP1 | FALSE | FALSE | TRUE | | Th* <all |
| NLRP2 | FALSE | FALSE | TRUE | | Th* <all |
| NME6 | FALSE | FALSE | TRUE | | Th* <all |
| NMRAL1 | FALSE | FALSE | TRUE | | Th* <all |
| NOMO2 | FALSE | FALSE | FALSE | | remainder |
| NOP14-AS1 | FALSE | FALSE | FALSE | | remainder |
| NOSIP | FALSE | FALSE | FALSE | | remainder |
| NPDC1 | TRUE | FALSE | FALSE | Th* intermediate | |
| NPHP4 | TRUE | FALSE | FALSE | Th* intermediate | |
| NPM3 | FALSE | TRUE | FALSE | | Th* >all |
| NPRL2 | FALSE | FALSE | FALSE | | remainder |
| NQO2 | FALSE | FALSE | TRUE | | Th* <all |
| NR1D1 | TRUE | FALSE | FALSE | Th* intermediate | |
| NR4A3 | FALSE | FALSE | FALSE | | remainder |
| NRADDP | FALSE | FALSE | TRUE | | Th* <all |
| NRBP2 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| NRIP1 | FALSE | FALSE | FALSE | | remainder |
| NRIP3 | FALSE | FALSE | FALSE | | remainder |
| NRN1 | FALSE | FALSE | FALSE | | remainder |
| NT5E | FALSE | FALSE | FALSE | | remainder |
| NTN4 | FALSE | TRUE | FALSE | | Th* >all |
| NTRK2 | TRUE | FALSE | FALSE | Th* ~Th1 | |
| NUAK2 | FALSE | FALSE | FALSE | | remainder |
| NUCB2 | FALSE | FALSE | FALSE | | remainder |
| NUDCD2 | FALSE | FALSE | FALSE | | remainder |
| NUP133 | FALSE | FALSE | FALSE | | remainder |
| NUSAP1 | FALSE | FALSE | TRUE | | Th* <all |
| NXN | TRUE | FALSE | FALSE | Th* intermediate | |
| OAF | TRUE | FALSE | FALSE | Th* ~Th1 | |
| OBFC2A | FALSE | FALSE | TRUE | | Th* <all |
| OBSCN | FALSE | FALSE | FALSE | | remainder |
| OCEL1 | FALSE | TRUE | FALSE | | Th* >all |
| OCIAD2 | FALSE | FALSE | FALSE | | remainder |
| OGFRL1 | FALSE | FALSE | FALSE | | remainder |
| OGG1 | FALSE | FALSE | FALSE | | remainder |
| OPA3 | FALSE | FALSE | FALSE | | remainder |
| OR1F2P | TRUE | FALSE | FALSE | Th* ~Th17 | |
| OR2L1P | TRUE | FALSE | FALSE | Th* ~Th17 | |
| OSBPL1A | TRUE | FALSE | FALSE | Th* intermediate | |
| OSGEPL1 | TRUE | FALSE | FALSE | Th* ~Th17 | |
| OTUB1 | FALSE | FALSE | TRUE | | Th* <all |
| P2RX5 | TRUE | FALSE | FALSE | Th* ~Th1 | |
| P2RX7 | FALSE | FALSE | TRUE | | Th* <all |
| PABPC1 | FALSE | TRUE | FALSE | | Th* >all |
| PABPC3 | FALSE | FALSE | FALSE | | remainder |
| PACS1 | FALSE | FALSE | FALSE | | remainder |
| PACSIN1 | TRUE | FALSE | FALSE | Th* intermediate | |
| PACSIN2 | FALSE | FALSE | FALSE | | remainder |
| PAF1 | FALSE | FALSE | FALSE | | remainder |
| PAFAH1B3 | FALSE | FALSE | FALSE | | remainder |
| PAM | FALSE | FALSE | FALSE | | remainder |
| PAR5 | FALSE | FALSE | FALSE | | remainder |
| PARD6A | FALSE | TRUE | FALSE | | Th* >all |
| PARP12 | FALSE | FALSE | FALSE | | remainder |
| PARP2 | FALSE | FALSE | FALSE | | remainder |
| PARP3 | FALSE | FALSE | FALSE | | remainder |
| PARVB | FALSE | FALSE | FALSE | | remainder |
| PASK | FALSE | FALSE | FALSE | | remainder |
| PATL2 | FALSE | FALSE | FALSE | | remainder |
| PCBP4 | FALSE | FALSE | FALSE | | remainder |
| PCNXL3 | FALSE | FALSE | FALSE | | remainder |
| PCSK7 | FALSE | FALSE | FALSE | | remainder |
| PDCD5 | TRUE | FALSE | FALSE | Th* ~Th1 | |
| PDCD7 | FALSE | FALSE | FALSE | | remainder |
| PDCL | FALSE | FALSE | FALSE | | remainder |
| PDE4D | FALSE | TRUE | FALSE | | Th* >all |
| PDE8A | FALSE | FALSE | TRUE | | Th* <all |
| PDE9A | FALSE | FALSE | FALSE | | remainder |
| PDGFB | FALSE | FALSE | FALSE | | remainder |
| PDGFD | TRUE | FALSE | FALSE | Th* ~Th17 | |
| PDHX | FALSE | TRUE | FALSE | | Th* >all |
| PDLIM1 | FALSE | FALSE | TRUE | | Th* <all |
| PDZD2 | TRUE | TRUE | FALSE | Th* intermediate | Th* >all |
| PDZD8 | TRUE | FALSE | FALSE | Th* ~Th1 | |
| PELI2 | FALSE | FALSE | FALSE | | remainder |
| PELI3 | FALSE | TRUE | FALSE | | Th* >all |
| PER3 | TRUE | FALSE | FALSE | Th* intermediate | |
| PERP | FALSE | FALSE | FALSE | | remainder |
| PEX26 | FALSE | FALSE | FALSE | | remainder |
| PFKFB3 | FALSE | FALSE | FALSE | | remainder |
| PFKL | FALSE | FALSE | FALSE | | remainder |
| PFN1 | FALSE | FALSE | FALSE | | remainder |
| PFN1P2 | FALSE | FALSE | FALSE | | remainder |
| PFN2 | FALSE | FALSE | FALSE | | remainder |
| PGM2L1 | FALSE | FALSE | FALSE | | remainder |
| PHLDA1 | TRUE | FALSE | FALSE | Th* ~Th1 | |
| PHLDB3 | FALSE | FALSE | FALSE | | remainder |
| PHTF2 | FALSE | FALSE | FALSE | | remainder |
| PI16 | TRUE | FALSE | FALSE | Th* intermediate | |
| PIDD | FALSE | FALSE | TRUE | | Th* <all |
| PIEZO1 | FALSE | FALSE | TRUE | | Th* <all |
| PIGF | FALSE | FALSE | TRUE | | Th* <all |
| PIGV | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| PIM1 | FALSE | FALSE | FALSE | | remainder |
| PIM3 | FALSE | FALSE | FALSE | | remainder |
| PION | FALSE | FALSE | FALSE | | remainder |
| PITPNC1 | FALSE | FALSE | FALSE | | remainder |
| PITPNM1 | FALSE | FALSE | TRUE | | Th* <all |
| PJA1 | FALSE | FALSE | TRUE | | Th* <all |
| PKIA | TRUE | FALSE | FALSE | Th* ~Th1 | |
| PKN1 | FALSE | FALSE | FALSE | | remainder |
| PKP2 | FALSE | FALSE | FALSE | | remainder |
| PLAC8 | TRUE | FALSE | FALSE | Th* intermediate | |
| PLBD2 | FALSE | FALSE | FALSE | | remainder |
| PLCB1 | TRUE | FALSE | FALSE | Th* ~Th1 | |
| PLCD1 | FALSE | FALSE | TRUE | | Th* <all |
| PLCH2 | FALSE | FALSE | TRUE | | Th* <all |
| PLCL1 | TRUE | FALSE | FALSE | Th* intermediate | |
| PLCXD2 | FALSE | FALSE | FALSE | | remainder |
| PLD1 | TRUE | FALSE | FALSE | Th* ~Th1 | |
| PLEC | TRUE | FALSE | TRUE | Th* ~Th1 | Th* <all |
| PLEKHA7 | FALSE | FALSE | FALSE | | remainder |
| PLEKHF1 | FALSE | FALSE | FALSE | | remainder |
| PLEKHG1 | TRUE | FALSE | FALSE | Th* intermediate | |
| PLEKHN1 | FALSE | TRUE | FALSE | | Th* >all |
| PLK1 | TRUE | FALSE | FALSE | Th* ~Th1 | |
| PLP2 | TRUE | FALSE | FALSE | Th* intermediate | |
| PLSCR1 | FALSE | FALSE | FALSE | | remainder |
| PLXDC1 | FALSE | FALSE | FALSE | | remainder |
| PLXNA4 | FALSE | FALSE | FALSE | | remainder |
| PLXNC1 | FALSE | FALSE | FALSE | | remainder |
| PLXND1 | FALSE | FALSE | FALSE | | remainder |
| PMS2P4 | FALSE | FALSE | TRUE | | Th* <all |
| PMVK | FALSE | FALSE | FALSE | | remainder |
| PNKP | FALSE | FALSE | TRUE | | Th* <all |
| PNPLA6 | FALSE | FALSE | FALSE | | remainder |
| POLR1A | FALSE | FALSE | FALSE | | remainder |
| POLR1C | FALSE | FALSE | FALSE | | remainder |
| POLR2I | FALSE | FALSE | TRUE | | Th* <all |
| POLR2J | FALSE | FALSE | TRUE | | Th* <all |
| POLR2L | FALSE | FALSE | TRUE | | Th* <all |
| POLR3F | FALSE | FALSE | FALSE | | remainder |
| POLR3H | TRUE | FALSE | FALSE | Th* intermediate | |
| POLR3K | FALSE | FALSE | FALSE | | remainder |
| POP5 | FALSE | FALSE | FALSE | | remainder |
| POR | FALSE | FALSE | FALSE | | remainder |
| PPARG | TRUE | FALSE | FALSE | Th* ~Th1 | |
| PPBP | FALSE | TRUE | FALSE | | Th* >all |
| PPIA | FALSE | TRUE | FALSE | | Th* >all |
| PPIB | FALSE | FALSE | TRUE | | Th* <all |
| PPP1CA | FALSE | FALSE | FALSE | | remainder |
| PPP1R14B | FALSE | FALSE | FALSE | | remainder |
| PPP1R26 | FALSE | FALSE | FALSE | | remainder |
| PPP1R3D | FALSE | FALSE | FALSE | | remainder |
| PPP1R3F | FALSE | FALSE | FALSE | | remainder |
| PPP2R2A | FALSE | FALSE | FALSE | | remainder |
| PPP2R2B | FALSE | FALSE | FALSE | | remainder |
| PPP2R5E | FALSE | FALSE | TRUE | | Th* <all |
| PPP5C | FALSE | FALSE | FALSE | | remainder |
| PPP6R1 | FALSE | FALSE | TRUE | | Th* <all |
| PPT1 | FALSE | FALSE | FALSE | | remainder |
| PRADC1 | FALSE | FALSE | TRUE | | Th* <all |
| PRC1 | FALSE | FALSE | FALSE | | remainder |
| PRDX3 | FALSE | FALSE | FALSE | | remainder |
| PRDX4 | FALSE | FALSE | FALSE | | remainder |
| PREP | FALSE | TRUE | FALSE | | Th* >all |
| PRF1 | FALSE | TRUE | FALSE | | Th* >all |
| PRKCA | FALSE | FALSE | FALSE | | remainder |
| PRKCI | FALSE | FALSE | FALSE | | remainder |
| PRO1768 | FALSE | TRUE | FALSE | | Th* >all |
| PROCR | FALSE | TRUE | FALSE | | Th* >all |
| PROK2 | FALSE | TRUE | FALSE | | Th* >all |
| PRPSAP1 | FALSE | FALSE | FALSE | | remainder |
| PRR11 | FALSE | FALSE | TRUE | | Th* <all |
| PRR5L | FALSE | FALSE | TRUE | | Th* <all |
| PRRC2A | FALSE | FALSE | FALSE | | remainder |
| PRUNE2 | FALSE | FALSE | FALSE | | remainder |
| PSEN2 | FALSE | FALSE | FALSE | | remainder |
| PSMB5 | FALSE | TRUE | FALSE | | Th* >all |
| PSMC5 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| PSMD4 | FALSE | FALSE | FALSE | | remainder |
| PSMG3 | FALSE | TRUE | FALSE | | Th* >all |
| PSTPIP1 | FALSE | FALSE | TRUE | | Th* <all |
| PTCH1 | TRUE | FALSE | FALSE | Th* ~Th1 | |
| PTGDR | TRUE | FALSE | FALSE | Th* ~Th1 | |
| PTGDR2 | FALSE | FALSE | FALSE | | remainder |
| PTGS2 | FALSE | TRUE | FALSE | | Th* >all |
| PTK2 | FALSE | FALSE | TRUE | | Th* <all |
| PTK6 | FALSE | FALSE | TRUE | | Th* <all |
| PTPN12 | FALSE | FALSE | FALSE | | remainder |
| PTPN13 | TRUE | FALSE | FALSE | Th* ~Th17 | |
| PTPN4 | FALSE | FALSE | FALSE | | remainder |
| PTPRF | FALSE | TRUE | FALSE | | Th* >all |
| PTPRM | TRUE | FALSE | FALSE | Th* intermediate | |
| PTPRN2 | FALSE | FALSE | TRUE | | Th* <all |
| PVRL3 | FALSE | FALSE | FALSE | | remainder |
| PVT1 | FALSE | FALSE | FALSE | | remainder |
| PWP2 | FALSE | FALSE | TRUE | | Th* <all |
| PYGM | FALSE | FALSE | FALSE | | remainder |
| PZP | TRUE | FALSE | FALSE | Th* ~Th1 | |
| QDPR | FALSE | FALSE | FALSE | | remainder |
| QRICH1 | FALSE | FALSE | FALSE | | remainder |
| RAB11B | FALSE | FALSE | FALSE | | remainder |
| RAB11FIP1 | FALSE | FALSE | FALSE | | remainder |
| RAB11FIP5 | TRUE | FALSE | FALSE | Th* ~Th1 | |
| RAB12 | FALSE | TRUE | FALSE | | Th* >all |
| RAB1B | FALSE | FALSE | TRUE | | Th* <all |
| RAB25 | FALSE | FALSE | FALSE | | remainder |
| RAB30 | TRUE | FALSE | FALSE | Th* intermediate | |
| RAB34 | FALSE | FALSE | FALSE | | remainder |
| RAB8B | FALSE | FALSE | FALSE | | remainder |
| RABAC1 | FALSE | FALSE | TRUE | | Th* <all |
| RAD54B | FALSE | TRUE | FALSE | | Th* >all |
| RAI14 | FALSE | TRUE | FALSE | | Th* >all |
| RAMP3 | FALSE | FALSE | FALSE | | remainder |
| RAPH1 | TRUE | FALSE | FALSE | Th* ~Th1 | |
| RARG | TRUE | FALSE | FALSE | Th* intermediate | |
| RASA2 | FALSE | FALSE | FALSE | | remainder |
| RASGEF1A | TRUE | FALSE | FALSE | Th* intermediate | |
| RASGEF1B | TRUE | FALSE | FALSE | Th* intermediate | |
| RASGRF2 | TRUE | FALSE | FALSE | Th* ~Th1 | |
| RASSF1 | FALSE | FALSE | FALSE | | remainder |
| RAVER1 | FALSE | FALSE | FALSE | | remainder |
| RBM11 | TRUE | FALSE | TRUE | Th* ~Th1 | Th* <all |
| RBM38 | FALSE | FALSE | FALSE | | remainder |
| RBM47 | FALSE | FALSE | FALSE | | remainder |
| RCAN2 | TRUE | FALSE | FALSE | Th* ~Th17 | |
| RCBTB2 | TRUE | FALSE | FALSE | Th* ~Th1 | |
| RELT | FALSE | FALSE | FALSE | | remainder |
| REREP3 | TRUE | FALSE | FALSE | Th* intermediate | |
| RFX8 | FALSE | FALSE | FALSE | | remainder |
| RFXANK | FALSE | FALSE | FALSE | | remainder |
| RG9MTD1 | FALSE | FALSE | FALSE | | remainder |
| RGMB | TRUE | FALSE | FALSE | Th* ~Th1 | |
| RGS1 | FALSE | FALSE | TRUE | | Th* <all |
| RGS12 | FALSE | FALSE | TRUE | | Th* <all |
| RGS18 | TRUE | FALSE | FALSE | Th* ~Th17 | |
| RHBDD1 | FALSE | FALSE | FALSE | | remainder |
| RHBDD2 | FALSE | FALSE | FALSE | | remainder |
| RHBDF2 | FALSE | FALSE | FALSE | | remainder |
| RHOB | FALSE | FALSE | FALSE | | remainder |
| RHOC | FALSE | FALSE | FALSE | | remainder |
| RHOF | FALSE | FALSE | TRUE | | Th* <all |
| RHOU | FALSE | TRUE | FALSE | | Th* >all |
| RIN3 | FALSE | FALSE | TRUE | | Th* <all |
| RIPK2 | FALSE | TRUE | FALSE | | Th* >all |
| RLN2 | FALSE | TRUE | FALSE | | Th* >all |
| RLTPR | FALSE | FALSE | TRUE | | Th* <all |
| RNF122 | FALSE | FALSE | FALSE | | remainder |
| RNF166 | FALSE | FALSE | FALSE | | remainder |
| RNF214 | FALSE | FALSE | FALSE | | remainder |
| RNH1 | FALSE | FALSE | FALSE | | remainder |
| ROGDI | TRUE | FALSE | FALSE | Th* intermediate | |
| RORA | FALSE | FALSE | FALSE | | remainder |
| RORC | TRUE | FALSE | FALSE | Th* ~Th17 | |
| RP2 | TRUE | FALSE | FALSE | Th* ~Th1 | |
| RPA1 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| RPL17 | FALSE | TRUE | FALSE | | Th* >all |
| RPL18 | FALSE | FALSE | TRUE | | Th* <all |
| RPL18A | FALSE | FALSE | TRUE | | Th* <all |
| RPL22L1 | FALSE | FALSE | FALSE | | remainder |
| RPL23P8 | FALSE | FALSE | FALSE | | remainder |
| RPL27A | FALSE | FALSE | FALSE | | remainder |
| RPL28 | FALSE | FALSE | TRUE | | Th* <all |
| RPL31P11 | FALSE | TRUE | FALSE | | Th* >all |
| RPL36A | FALSE | FALSE | FALSE | | remainder |
| RPL37 | FALSE | FALSE | FALSE | | remainder |
| RPL37A | FALSE | FALSE | FALSE | | remainder |
| RPL38 | FALSE | FALSE | TRUE | | Th* <all |
| RPL39 | FALSE | TRUE | FALSE | | Th* >all |
| RPLP2 | FALSE | FALSE | TRUE | | Th* <all |
| RPS29 | FALSE | FALSE | FALSE | | remainder |
| RPS5 | FALSE | FALSE | FALSE | | remainder |
| RPS6KA2 | FALSE | FALSE | FALSE | | remainder |
| RPS9 | FALSE | FALSE | FALSE | | remainder |
| RRAGD | FALSE | TRUE | FALSE | | Th* >all |
| RRBP1 | FALSE | FALSE | FALSE | | remainder |
| RRP12 | FALSE | FALSE | FALSE | | remainder |
| RRP9 | FALSE | FALSE | FALSE | | remainder |
| RTKN2 | TRUE | FALSE | FALSE | Th* ~Th1 | |
| RUNX1-IT1 | FALSE | FALSE | TRUE | | Th* <all |
| RUNX2 | FALSE | TRUE | FALSE | | Th* >all |
| RUSC2 | TRUE | FALSE | FALSE | Th* ~Th17 | |
| S100A11 | TRUE | FALSE | FALSE | Th* ~Th1 | |
| S100A4 | TRUE | FALSE | FALSE | Th* intermediate | |
| S100A6 | FALSE | FALSE | FALSE | | remainder |
| S100B | FALSE | TRUE | FALSE | | Th* >all |
| S100PBP | TRUE | FALSE | FALSE | Th* intermediate | |
| SAMD12 | TRUE | FALSE | FALSE | Th* ~Th17 | |
| SAMD12-AS1 | FALSE | TRUE | FALSE | | Th* >all |
| SAMD3 | TRUE | FALSE | FALSE | Th* ~Th1 | |
| SAP30 | FALSE | FALSE | FALSE | | remainder |
| SARDH | FALSE | FALSE | TRUE | | Th* <all |
| SASH1 | FALSE | TRUE | FALSE | | Th* >all |
| SAT2 | FALSE | TRUE | FALSE | | Th* >all |
| SATB1 | FALSE | FALSE | FALSE | | remainder |
| SBF1 | FALSE | FALSE | FALSE | | remainder |
| SBF2 | FALSE | FALSE | FALSE | | remainder |
| SBK1 | FALSE | FALSE | FALSE | | remainder |
| SBNO2 | FALSE | FALSE | TRUE | | Th* <all |
| SCAP | FALSE | FALSE | FALSE | | remainder |
| SCARNA17 | FALSE | FALSE | FALSE | | remainder |
| SCD | TRUE | FALSE | FALSE | Th* ~Th1 | |
| SCML1 | FALSE | FALSE | FALSE | | remainder |
| SCNN1A | TRUE | FALSE | FALSE | Th* ~Th17 | |
| SCRN1 | FALSE | FALSE | FALSE | | remainder |
| SCYL1 | FALSE | FALSE | TRUE | | Th* <all |
| SDC4 | FALSE | FALSE | FALSE | | remainder |
| SDHB | FALSE | FALSE | FALSE | | remainder |
| SDK2 | FALSE | FALSE | FALSE | | remainder |
| SEC14L2 | FALSE | FALSE | FALSE | | remainder |
| SEC24C | FALSE | FALSE | FALSE | | remainder |
| SEC61B | FALSE | FALSE | FALSE | | remainder |
| SELL | FALSE | FALSE | FALSE | | remainder |
| SELP | FALSE | FALSE | TRUE | | Th* <all |
| SEMA3G | TRUE | FALSE | FALSE | Th* ~Th1 | |
| SEMA5A | TRUE | FALSE | TRUE | Th* ~Th1 | Th* <all |
| SEPN1 | FALSE | FALSE | FALSE | | remainder |
| SEPT10 | FALSE | FALSE | TRUE | | Th* <all |
| SEPT11 | TRUE | FALSE | FALSE | Th* ~Th1 | |
| SEPT4 | FALSE | TRUE | FALSE | | Th* >all |
| SERPINB6 | TRUE | FALSE | FALSE | Th* ~Th1 | |
| SESN1 | FALSE | FALSE | FALSE | | remainder |
| SESN3 | TRUE | FALSE | FALSE | Th* ~Th17 | |
| SETD7 | TRUE | FALSE | FALSE | Th* ~Th17 | |
| SF3A2 | FALSE | FALSE | FALSE | | remainder |
| SFXN5 | FALSE | FALSE | TRUE | | Th* <all |
| SGK223 | FALSE | FALSE | FALSE | | remainder |
| SGSM3 | FALSE | FALSE | FALSE | | remainder |
| SH2D2A | FALSE | FALSE | FALSE | | remainder |
| SH2D3C | FALSE | FALSE | FALSE | | remainder |
| SH2D4A | FALSE | FALSE | TRUE | | Th* <all |
| SH3PXD2A | FALSE | FALSE | FALSE | | remainder |
| SH3RF3 | FALSE | FALSE | FALSE | | remainder |

TABLE 1-continued

| gene | th1 vs. th17 significant | th* up | th* down | heatmap grouping I | heatmap grouping II |
|---|---|---|---|---|---|
| SH3TC1 | TRUE | FALSE | TRUE | Th* ~Th1 | Th* <all |
| SHMT2 | FALSE | FALSE | FALSE | | remainder |
| SIAE | FALSE | FALSE | FALSE | | remainder |
| SIAH1 | FALSE | FALSE | FALSE | | remainder |
| SIGIRR | FALSE | FALSE | FALSE | | remainder |
| SIGLECP3 | FALSE | FALSE | FALSE | | remainder |
| SIL1 | FALSE | FALSE | TRUE | | Th* <all |
| SIPA1 | TRUE | FALSE | FALSE | Th* intermediate | |
| SIPA1L2 | FALSE | TRUE | FALSE | | Th* >all |
| SIVA1 | FALSE | FALSE | TRUE | | Th* <all |
| SKI | FALSE | FALSE | FALSE | | remainder |
| SLAMF1 | FALSE | FALSE | FALSE | | remainder |
| SLAMF7 | TRUE | FALSE | FALSE | Th* ~Th1 | |
| SLC14A1 | FALSE | FALSE | FALSE | | remainder |
| SLC17A3 | FALSE | TRUE | FALSE | | Th* >all |
| SLC22A15 | FALSE | TRUE | FALSE | | Th* >all |
| SLC22A23 | FALSE | FALSE | FALSE | | remainder |
| SLC22A3 | TRUE | FALSE | FALSE | Th* ~Th1 | |
| SLC25A28 | FALSE | FALSE | FALSE | | remainder |
| SLC25A33 | FALSE | FALSE | FALSE | | remainder |
| SLC25A45 | FALSE | FALSE | TRUE | | Th* <all |
| SLC27A3 | TRUE | FALSE | FALSE | Th* intermediate | |
| SLC2A3 | FALSE | FALSE | FALSE | | remainder |
| SLC35B1 | FALSE | FALSE | FALSE | | remainder |
| SLC36A1 | FALSE | FALSE | TRUE | | Th* <all |
| SLC40A1 | FALSE | FALSE | FALSE | | remainder |
| SLC4A10 | FALSE | TRUE | FALSE | | Th* >all |
| SLC4A4 | TRUE | FALSE | FALSE | Th* ~Th1 | |
| SLC9A7 | FALSE | FALSE | TRUE | | Th* <all |
| SLC9A9 | FALSE | FALSE | FALSE | | remainder |
| SLFN11 | FALSE | FALSE | FALSE | | remainder |
| SLFN14 | FALSE | TRUE | FALSE | | Th* >all |
| SLFN5 | FALSE | FALSE | FALSE | | remainder |
| SMA4 | FALSE | FALSE | FALSE | | remainder |
| SMAD3 | TRUE | FALSE | FALSE | Th* ~Th1 | |
| SMAD7 | FALSE | FALSE | FALSE | | remainder |
| SMAGP | TRUE | FALSE | FALSE | Th* ~Th1 | |
| SMARCD3 | FALSE | FALSE | FALSE | | remainder |
| SMNDC1 | FALSE | FALSE | FALSE | | remainder |
| SND1-IT1 | FALSE | TRUE | FALSE | | Th* >all |
| SNED1 | FALSE | FALSE | FALSE | | remainder |
| SNHG10 | FALSE | FALSE | FALSE | | remainder |
| SNHG12 | FALSE | TRUE | FALSE | | Th* >all |
| SNHG8 | FALSE | TRUE | FALSE | | Th* >all |
| SNORA12 | FALSE | FALSE | FALSE | | remainder |
| SNORA23 | FALSE | TRUE | FALSE | | Th* >all |
| SNORA25 | FALSE | TRUE | FALSE | | Th* >all |
| SNORA56 | FALSE | TRUE | FALSE | | Th* >all |
| SNORA8 | FALSE | TRUE | FALSE | | Th* >all |
| SNORD100 | FALSE | TRUE | FALSE | | Th* >all |
| SNORD50A | FALSE | TRUE | FALSE | | Th* >all |
| SNTB1 | TRUE | FALSE | FALSE | Th* intermediate | |
| SNX9 | FALSE | FALSE | FALSE | | remainder |
| SOAT2 | FALSE | FALSE | FALSE | | remainder |
| SOCS2 | TRUE | FALSE | FALSE | Th* ~Th17 | |
| SOCS5 | FALSE | TRUE | FALSE | | Th* >all |
| SORL1 | FALSE | FALSE | FALSE | | remainder |
| SOS1 | TRUE | FALSE | FALSE | Th* intermediate | |
| SOWAHC | FALSE | FALSE | FALSE | | remainder |
| SOX13 | TRUE | FALSE | FALSE | Th* ~Th1 | |
| SPAG7 | FALSE | FALSE | FALSE | | remainder |
| SPATA7 | FALSE | FALSE | FALSE | | remainder |
| SPATS2L | FALSE | FALSE | FALSE | | remainder |
| SPCS3 | FALSE | TRUE | FALSE | | Th* >all |
| SPG20 | FALSE | FALSE | FALSE | | remainder |
| SPNS1 | FALSE | FALSE | FALSE | | remainder |
| SPON1 | FALSE | TRUE | FALSE | | Th* >all |
| SPSB1 | TRUE | FALSE | TRUE | Th* ~Th1 | Th* <all |
| SRGAP2P2 | FALSE | FALSE | FALSE | | remainder |
| SRGAP3 | FALSE | FALSE | FALSE | | remainder |
| SRSF2 | FALSE | TRUE | FALSE | | Th* >all |
| SRSF9 | FALSE | TRUE | FALSE | | Th* >all |
| SSBP3 | FALSE | FALSE | FALSE | | remainder |
| SSBP4 | FALSE | FALSE | TRUE | | Th* <all |
| SSR4 | FALSE | FALSE | FALSE | | remainder |
| ST3GAL5 | FALSE | FALSE | FALSE | | remainder |
| ST6GALNAC1 | FALSE | FALSE | TRUE | | Th* <all |

TABLE 1-continued

| gene | th1 vs. th17 significant | th* up | th* down | heatmap grouping I | heatmap grouping II |
|---|---|---|---|---|---|
| ST6GALNAC2 | FALSE | FALSE | TRUE | | Th* <all |
| ST8SIA1 | FALSE | FALSE | FALSE | | remainder |
| STAM | TRUE | FALSE | FALSE | Th* ~Th1 | |
| STAP1 | TRUE | FALSE | FALSE | Th* ~Th1 | |
| STARD10 | TRUE | FALSE | FALSE | Th* ~Th1 | |
| STAT4 | FALSE | FALSE | FALSE | | remainder |
| STAT6 | FALSE | FALSE | FALSE | | remainder |
| STMN1 | FALSE | FALSE | TRUE | | Th* <all |
| STOM | TRUE | FALSE | FALSE | Th* ~Th1 | |
| STRAP | FALSE | TRUE | FALSE | | Th* >all |
| STX10 | FALSE | FALSE | FALSE | | remainder |
| STX1A | FALSE | FALSE | TRUE | | Th* <all |
| SUMF1 | FALSE | FALSE | FALSE | | remainder |
| SURF2 | FALSE | FALSE | FALSE | | remainder |
| SUSD4 | FALSE | FALSE | FALSE | | remainder |
| SVIP | FALSE | FALSE | FALSE | | remainder |
| SYNGR3 | TRUE | FALSE | FALSE | Th* intermediate | |
| SYNM | TRUE | FALSE | FALSE | Th* intermediate | |
| SYT11 | FALSE | FALSE | FALSE | | remainder |
| SYTL2 | FALSE | FALSE | FALSE | | remainder |
| TADA2A | FALSE | FALSE | TRUE | | Th* <all |
| TANC1 | FALSE | FALSE | FALSE | | remainder |
| TAPBP | FALSE | FALSE | FALSE | | remainder |
| TARP | TRUE | FALSE | FALSE | Th* ~Th1 | |
| TARS2 | FALSE | FALSE | TRUE | | Th* <all |
| TBC1D10B | FALSE | FALSE | FALSE | | remainder |
| TBC1D2 | TRUE | FALSE | FALSE | Th* intermediate | |
| TBC1D4 | FALSE | FALSE | FALSE | | remainder |
| TBCA | FALSE | FALSE | FALSE | | remainder |
| TBCB | FALSE | FALSE | FALSE | | remainder |
| TBKBP1 | TRUE | FALSE | FALSE | Th* ~Th1 | |
| TBX21 | TRUE | FALSE | FALSE | Th* ~Th1 | |
| TBXAS1 | TRUE | FALSE | FALSE | Th* ~Th1 | |
| TCEA3 | FALSE | FALSE | FALSE | | remainder |
| TCEB2 | FALSE | FALSE | TRUE | | Th* <all |
| TCIRG1 | FALSE | FALSE | FALSE | | remainder |
| TCP11L2 | FALSE | FALSE | FALSE | | remainder |
| TCTEX1D4 | FALSE | FALSE | TRUE | | Th* <all |
| TDG | FALSE | FALSE | FALSE | | remainder |
| TDP2 | FALSE | FALSE | FALSE | | remainder |
| TDRKH | FALSE | FALSE | FALSE | | remainder |
| TEC | FALSE | TRUE | FALSE | | Th* >all |
| TECPR1 | FALSE | FALSE | TRUE | | Th* <all |
| TEPP | FALSE | TRUE | FALSE | | Th* >all |
| TEX264 | FALSE | FALSE | FALSE | | remainder |
| TFCP2L1 | FALSE | FALSE | FALSE | | remainder |
| TGFBI | FALSE | FALSE | TRUE | | Th* <all |
| TGFBR1 | FALSE | FALSE | FALSE | | remainder |
| THBS1 | FALSE | FALSE | FALSE | | remainder |
| THY1 | FALSE | TRUE | FALSE | | Th* >all |
| TIAM1 | TRUE | FALSE | FALSE | Th* ~Th1 | |
| TIFA | FALSE | FALSE | FALSE | | remainder |
| TIGIT | FALSE | FALSE | TRUE | | Th* <all |
| TIMM13 | FALSE | FALSE | FALSE | | remainder |
| TIMM50 | FALSE | FALSE | TRUE | | Th* <all |
| TLE1 | FALSE | TRUE | FALSE | | Th* >all |
| TLR5 | FALSE | FALSE | FALSE | | remainder |
| TM9SF1 | FALSE | FALSE | FALSE | | remainder |
| TMC8 | FALSE | FALSE | FALSE | | remainder |
| TMCC3 | TRUE | FALSE | FALSE | Th* ~Th1 | |
| TMED9 | FALSE | TRUE | FALSE | | Th* >all |
| TMEM120A | FALSE | FALSE | TRUE | | Th* <all |
| TMEM126A | FALSE | FALSE | FALSE | | remainder |
| TMEM136 | FALSE | TRUE | FALSE | | Th* >all |
| TMEM154 | FALSE | FALSE | FALSE | | remainder |
| TMEM183A | FALSE | TRUE | FALSE | | Th* >all |
| TMEM186 | FALSE | TRUE | FALSE | | Th* >all |
| TMEM198B | FALSE | FALSE | FALSE | | remainder |
| TMEM2 | FALSE | FALSE | FALSE | | remainder |
| TMEM216 | FALSE | FALSE | FALSE | | remainder |
| TMEM238 | FALSE | FALSE | FALSE | | remainder |
| TMEM30B | FALSE | FALSE | FALSE | | remainder |
| TMEM62 | FALSE | FALSE | FALSE | | remainder |
| TMEM64 | FALSE | FALSE | FALSE | | remainder |
| TMIE | FALSE | FALSE | TRUE | | Th* <all |
| TMSB10 | FALSE | FALSE | FALSE | | remainder |
| TMUB1 | FALSE | FALSE | TRUE | | Th* <all |

TABLE 1-continued

| gene | th1 vs. th17 significant | th* up | th* down | heatmap grouping I | heatmap grouping II |
|---|---|---|---|---|---|
| TNFRSF11A | FALSE | FALSE | FALSE | | remainder |
| TNFRSF9 | FALSE | FALSE | FALSE | | remainder |
| TNFSF11 | FALSE | FALSE | FALSE | | remainder |
| TNFSF13B | FALSE | TRUE | FALSE | | Th* >all |
| TNRC18 | FALSE | FALSE | TRUE | | Th* <all |
| TOB2 | FALSE | FALSE | FALSE | | remainder |
| TOM1 | FALSE | FALSE | FALSE | | remainder |
| TOP2A | FALSE | FALSE | TRUE | | Th* <all |
| TOP3B | FALSE | FALSE | FALSE | | remainder |
| TOR1A | FALSE | FALSE | FALSE | | remainder |
| TOR3A | FALSE | FALSE | FALSE | | remainder |
| TOX | FALSE | FALSE | TRUE | | Th* <all |
| TP63 | TRUE | FALSE | TRUE | Th* intermediate | Th* <all |
| TPBG | FALSE | TRUE | FALSE | | Th* >all |
| TPCN1 | FALSE | FALSE | FALSE | | remainder |
| TPCN2 | FALSE | FALSE | FALSE | | remainder |
| TPD52 | FALSE | FALSE | FALSE | | remainder |
| TPM2 | FALSE | TRUE | FALSE | | Th* >all |
| TPX2 | FALSE | FALSE | TRUE | | Th* <all |
| TRAF1 | FALSE | FALSE | FALSE | | remainder |
| TRAPPC1 | FALSE | FALSE | FALSE | | remainder |
| TRAPPC2L | FALSE | FALSE | FALSE | | remainder |
| TRAPPC5 | FALSE | FALSE | TRUE | | Th* <all |
| TRIM2 | TRUE | FALSE | FALSE | Th* intermediate | |
| TRIM28 | FALSE | FALSE | TRUE | | Th* <all |
| TRIM35 | TRUE | FALSE | FALSE | Th* intermediate | |
| TRIM5 | FALSE | FALSE | FALSE | | remainder |
| TRIM59 | FALSE | FALSE | FALSE | | remainder |
| TRIM62 | FALSE | FALSE | TRUE | | Th* <all |
| TRMT1 | FALSE | FALSE | FALSE | | remainder |
| TRPS1 | FALSE | FALSE | FALSE | | remainder |
| TSGA10 | TRUE | FALSE | FALSE | Th* intermediate | |
| TSHZ1 | FALSE | FALSE | FALSE | | remainder |
| TSHZ2 | TRUE | FALSE | TRUE | Th* ~Th1 | Th* <all |
| TSHZ3 | TRUE | TRUE | FALSE | Th* ~Th1 | Th* >all |
| TSIX | FALSE | FALSE | FALSE | | remainder |
| TSPAN15 | TRUE | TRUE | FALSE | Th* ~Th17 | Th* >all |
| TSPAN32 | FALSE | FALSE | FALSE | | remainder |
| TSPAN33 | TRUE | FALSE | FALSE | Th* intermediate | |
| TSPO | FALSE | FALSE | TRUE | | Th* <all |
| TTC21A | FALSE | FALSE | FALSE | | remainder |
| TTC31 | FALSE | FALSE | FALSE | | remainder |
| TTN | FALSE | FALSE | TRUE | | Th* <all |
| TTTY15 | FALSE | FALSE | TRUE | | Th* <all |
| TTYH2 | FALSE | FALSE | FALSE | | remainder |
| TUB | FALSE | FALSE | TRUE | | Th* <all |
| TUBB2A | FALSE | FALSE | FALSE | | remainder |
| TUBG2 | FALSE | FALSE | TRUE | | Th* <all |
| TUBGCP2 | FALSE | FALSE | TRUE | | Th* <all |
| TXK | FALSE | FALSE | FALSE | | remainder |
| TXNL4A | FALSE | FALSE | FALSE | | remainder |
| TYMP | FALSE | FALSE | TRUE | | Th* <all |
| TYMS | FALSE | FALSE | TRUE | | Th* <all |
| TYROBP | TRUE | FALSE | FALSE | Th* intermediate | |
| TYSND1 | FALSE | FALSE | FALSE | | remainder |
| UBAC2 | FALSE | FALSE | FALSE | | remainder |
| UBASH3B | FALSE | FALSE | FALSE | | remainder |
| UBB | FALSE | FALSE | FALSE | | remainder |
| UBC | FALSE | FALSE | FALSE | | remainder |
| UBE2E2 | FALSE | TRUE | FALSE | | Th* >all |
| UBE2E3 | FALSE | FALSE | FALSE | | remainder |
| UBXN7 | FALSE | FALSE | FALSE | | remainder |
| UCHL3 | FALSE | FALSE | FALSE | | remainder |
| UCK1 | FALSE | FALSE | FALSE | | remainder |
| UCKL1-AS1 | FALSE | FALSE | TRUE | | Th* <all |
| UHRF1BP1 | FALSE | FALSE | FALSE | | remainder |
| UNC13B | FALSE | TRUE | FALSE | | Th* >all |
| UNC13D | FALSE | FALSE | TRUE | | Th* <all |
| UQCRB | FALSE | FALSE | FALSE | | remainder |
| UQCRQ | FALSE | FALSE | FALSE | | remainder |
| UROD | FALSE | FALSE | FALSE | | remainder |
| USF2 | FALSE | FALSE | FALSE | | remainder |
| USP18 | TRUE | FALSE | FALSE | Th* ~Th1 | |
| USP28 | TRUE | FALSE | FALSE | Th* intermediate | |
| USP36 | FALSE | FALSE | FALSE | | remainder |
| USP46 | TRUE | FALSE | FALSE | Th* intermediate | |
| UST | FALSE | TRUE | FALSE | | Th* >all |

TABLE 1-continued

| gene | th1 vs. th17 significant | th* up | th* down | heatmap grouping I | heatmap grouping II |
|---|---|---|---|---|---|
| UTS2 | FALSE | FALSE | FALSE | | remainder |
| VAMP8 | FALSE | FALSE | FALSE | | remainder |
| VANGL1 | FALSE | FALSE | TRUE | | Th* <all |
| VCL | TRUE | FALSE | FALSE | Th* intermediate | |
| VNN2 | TRUE | FALSE | FALSE | Th* intermediate | |
| VPS37C | TRUE | FALSE | FALSE | Th* ~Th1 | |
| VTA1 | FALSE | FALSE | FALSE | | remainder |
| WASF1 | FALSE | TRUE | FALSE | | Th* >all |
| WASH5P | FALSE | FALSE | TRUE | | Th* <all |
| WDR53 | FALSE | FALSE | FALSE | | remainder |
| WDR54 | FALSE | TRUE | FALSE | | Th* >all |
| WFDC2 | FALSE | TRUE | FALSE | | Th* >all |
| WHAMM | FALSE | FALSE | FALSE | | remainder |
| WIPI1 | FALSE | FALSE | TRUE | | Th* <all |
| WNT1 | FALSE | TRUE | FALSE | | Th* >all |
| WNT10A | TRUE | FALSE | FALSE | Th* ~Th1 | |
| WNT10B | FALSE | TRUE | FALSE | | Th* >all |
| XAB2 | FALSE | FALSE | TRUE | | Th* <all |
| XCL1 | TRUE | FALSE | FALSE | Th* intermediate | |
| XCL2 | FALSE | TRUE | FALSE | | Th* >all |
| XIST | FALSE | TRUE | FALSE | | Th* >all |
| XRCC3 | FALSE | FALSE | TRUE | | Th* <all |
| YARS | TRUE | FALSE | FALSE | Th* intermediate | |
| YBEY | FALSE | FALSE | FALSE | | remainder |
| YES1 | TRUE | FALSE | FALSE | Th* ~Th1 | |
| YIPF5 | FALSE | FALSE | FALSE | | remainder |
| YPEL1 | FALSE | FALSE | FALSE | | remainder |
| YRDC | FALSE | TRUE | FALSE | | Th* >all |
| YWHAH | TRUE | FALSE | FALSE | Th* ~Th17 | |
| ZAK | FALSE | TRUE | FALSE | | Th* >all |
| ZBED6 | FALSE | FALSE | TRUE | | Th* <all |
| ZBTB10 | FALSE | FALSE | FALSE | | remainder |
| ZBTB16 | FALSE | FALSE | TRUE | | Th* <all |
| ZBTB17 | FALSE | FALSE | TRUE | | Th* <all |
| ZBTB20 | FALSE | FALSE | FALSE | | remainder |
| ZBTB43 | FALSE | FALSE | FALSE | | remainder |
| ZBTB49 | TRUE | FALSE | FALSE | Th* ~Th1 | |
| ZBTB7B | FALSE | FALSE | TRUE | | Th* <all |
| ZC2HC1A | TRUE | FALSE | FALSE | Th* ~Th1 | |
| ZC3H12A | FALSE | FALSE | FALSE | | remainder |
| ZC3H12D | FALSE | FALSE | FALSE | | remainder |
| ZC3H3 | FALSE | FALSE | TRUE | | Th* <all |
| ZCCHC10 | FALSE | FALSE | TRUE | | Th* <all |
| ZCCHC18 | TRUE | FALSE | FALSE | Th* ~Th1 | |
| ZDHHC11 | TRUE | FALSE | FALSE | Th* ~Th1 | |
| ZDHHC14 | FALSE | FALSE | FALSE | | remainder |
| ZDHHC23 | FALSE | FALSE | FALSE | | remainder |
| ZDHHC7 | FALSE | FALSE | FALSE | | remainder |
| ZFHX3 | FALSE | TRUE | FALSE | | Th* >all |
| ZFP28 | FALSE | FALSE | TRUE | | Th* <all |
| ZFP36L1 | FALSE | FALSE | FALSE | | remainder |
| ZFP36L2 | FALSE | FALSE | FALSE | | remainder |
| ZFYVE28 | FALSE | FALSE | FALSE | | remainder |
| ZHX2 | TRUE | FALSE | FALSE | Th* intermediate | |
| ZIK1 | FALSE | FALSE | FALSE | | remainder |
| ZNF133 | FALSE | TRUE | FALSE | | Th* >all |
| ZNF208 | FALSE | FALSE | FALSE | | remainder |
| ZNF22 | FALSE | FALSE | FALSE | | remainder |
| ZNF32 | FALSE | FALSE | FALSE | | remainder |
| ZNF34 | FALSE | FALSE | FALSE | | remainder |
| ZNF358 | FALSE | FALSE | FALSE | | remainder |
| ZNF365 | FALSE | FALSE | TRUE | | Th* <all |
| ZNF434 | FALSE | FALSE | TRUE | | Th* <all |
| ZNF444 | FALSE | TRUE | FALSE | | Th* >all |
| ZNF462 | FALSE | FALSE | FALSE | | remainder |
| ZNF48 | FALSE | FALSE | FALSE | | remainder |
| ZNF512B | FALSE | FALSE | FALSE | | remainder |
| ZNF516 | TRUE | FALSE | FALSE | Th* ~Th17 | |
| ZNF532 | FALSE | FALSE | FALSE | | remainder |
| ZNF559 | FALSE | FALSE | FALSE | | remainder |
| ZNF574 | FALSE | FALSE | FALSE | | remainder |
| ZNF581 | FALSE | FALSE | FALSE | | remainder |
| ZNF614 | FALSE | FALSE | FALSE | | remainder |
| ZNF618 | TRUE | FALSE | FALSE | Th* ~Th1 | |
| ZNF620 | FALSE | FALSE | FALSE | | remainder |
| ZNF668 | FALSE | FALSE | FALSE | | remainder |
| ZNF711 | FALSE | TRUE | FALSE | | Th* >all |

TABLE 1-continued

| gene | th1 vs. th17 significant | th* up | th* down | heatmap grouping I | heatmap grouping II |
|---|---|---|---|---|---|
| ZNF76 | FALSE | FALSE | FALSE | | remainder |
| ZNF767 | FALSE | FALSE | FALSE | | remainder |
| ZNF827 | TRUE | FALSE | FALSE | Th* ~Th17 | |
| ZNF83 | FALSE | FALSE | FALSE | | remainder |
| ZNF839 | FALSE | FALSE | FALSE | | remainder |
| ZNF844 | TRUE | FALSE | FALSE | Th* ~Th1 | |
| ZNF853 | FALSE | FALSE | FALSE | | remainder |
| ZNRF1 | TRUE | FALSE | FALSE | Th* intermediate | |
| ZP1 | FALSE | FALSE | FALSE | | remainder |
| ZSCAN18 | FALSE | FALSE | FALSE | | remainder |
| ZSCAN22 | FALSE | FALSE | FALSE | | remainder |
| ZSCAN30 | FALSE | FALSE | FALSE | | remainder |
| ZSWIM1 | FALSE | FALSE | FALSE | | remainder |
| ZSWIM5 | FALSE | FALSE | FALSE | | remainder |
| ZYX | FALSE | FALSE | FALSE | | remainder |

TABLE 2

| Peptide id | Resp Freq | Total SFC | Peptides \| Organism → | My cobac terium_ absce ssus | My cobac terium_ avium_ 104 | My cobac terium_ avium_ subsps_ paratuber- culosis_ k_10 | My cobac terium_ gilvum_ PYR-GCK | My cobac- terium_ mari num_m | My cobac- terium_ str._ MC2_155 |
|---|---|---|---|---|---|---|---|---|---|
| 311 | 3% | 477 | RFTLLRPLLFTIAYE | 0 | 1 | 1 | 0 | 1 | 0 |
| 741 | 13% | 248 | KWETFLTQELPAYLA | 1 | 0 | 0 | 1 | 0 | 0 |
| 1364 | 3% | 228 | PLAENYLRLNALGAY | 0 | 0 | 0 | 1 | 0 | 1 |
| 446 | 3% | 182 | HEEIQLLANDFSTML | 0 | 0 | 0 | 1 | 1 | 0 |
| 329 | 7% | 167 | SLHMFFHRLGPVLAR | 0 | 1 | 1 | 0 | 1 | 1 |
| 582 | 10% | 158 | RLFPVIRRYALAYHV | 0 | 1 | 1 | 0 | 0 | 0 |
| 7 | 3% | 138 | LMVLFQYGVALHELE | 0 | 0 | 1 | 0 | 1 | 1 |
| 720 | 10% | 125 | DPLIFFRPRVERLFG | 0 | 0 | 0 | 1 | 0 | 0 |
| 1556 | 3% | 122 | YNVVIYPVTTLRLAM | 1 | 1 | 1 | 0 | 1 | 1 |
| 1224 | 10% | 97 | LMLIWACDLIVAADN | 0 | 1 | 1 | 0 | 1 | 0 |
| 829 | 3% | 93 | ETTRNLIALGTLALI | 0 | 1 | 1 | 1 | 0 | 0 |
| 777 | 7% | 87 | ALLYIPLLTRMLMNL | 1 | 0 | 0 | 0 | 1 | 0 |
| 752 | 3% | 78 | KDVFFYEPIILPEKS | 1 | 0 | 0 | 1 | 0 | 0 |
| 391 | 3% | 77 | LGVAALLFGFPIFFD | 0 | 0 | 0 | 1 | 0 | 1 |
| 775 | 7% | 70 | PKLKQFMSDVVWIEH | 1 | 0 | 0 | 0 | 1 | 0 |
| 587 | 7% | 68 | GSMLWVAALIGEEIF | 0 | 1 | 1 | 0 | 1 | 0 |
| 1258 | 3% | 60 | GRLIGWLAKVLAEHP | 0 | 1 | 1 | 0 | 1 | 1 |
| 868 | 3% | 58 | QWGYRMVLPQLILMP | 0 | 1 | 1 | 0 | 1 | 0 |
| 1471 | 7% | 58 | SQRLVTLSYRLDAAA | 0 | 0 | 0 | 1 | 0 | 1 |
| 8 | 3% | 58 | HQGLAFLLADMAAAV | 0 | 1 | 0 | 1 | 0 | 0 |
| 1331 | 3% | 58 | VEAGMVYVTLPPLFV | 0 | 0 | 0 | 1 | 0 | 0 |
| 804 | 3% | 57 | NSSIVLISLPAIFRG | 1 | 1 | 1 | 0 | 0 | 0 |
| 106 | 3% | 55 | GLSSAWLSLIFAEMI | 0 | 0 | 0 | 1 | 0 | 1 |
| 424 | 3% | 55 | AVPNFALTPLLIIWM | 0 | 0 | 0 | 1 | 0 | 1 |
| 1285 | 3% | 53 | PADASIVKLYYSELL | 0 | 0 | 0 | 0 | 0 | 1 |
| 447 | 3% | 53 | DDRRTLLWLANQRAV | 0 | 0 | 0 | 1 | 0 | 1 |
| 628 | 3% | 53 | LGVFPLIVMFLITSI | 0 | 0 | 0 | 0 | 0 | 1 |
| 588 | 3% | 52 | HLFQVMAFVVMEPPT | 0 | 1 | 1 | 1 | 0 | 0 |
| 1542 | 3% | 52 | GRVAWNIVTSYLDSA | 1 | 1 | 1 | 0 | 0 | 1 |
| 841 | 3% | 48 | PQFLIMPKLIPALIA | 0 | 1 | 1 | 0 | 1 | 0 |
| 1549 | 3% | 48 | RILQVFTEAYADVER | 1 | 0 | 0 | 0 | 0 | 1 |
| 1571 | 3% | 48 | ADGLVLFNRFLQPDI | 0 | 0 | 0 | 0 | 1 | 0 |
| 1218 | 3% | 48 | RTFFRYFPTKESVLF | 0 | 1 | 0 | 1 | 0 | 0 |
| 626 | 3% | 48 | ARAGFAASGVLHLLV | 0 | 0 | 0 | 0 | 0 | 1 |
| 861 | 3% | 47 | MVFATLLPLGVLQLY | 0 | 1 | 1 | 0 | 0 | 0 |
| 387 | 3% | 47 | RGQFWIWAGANIAPI | 0 | 0 | 0 | 1 | 0 | 1 |
| 1134 | 3% | 47 | TLLTMLWQNLIGNAV | 0 | 0 | 0 | 0 | 1 | 0 |
| 1458 | 3% | 47 | HFVSTLSATFPEGED | 0 | 0 | 0 | 1 | 0 | 0 |
| 1334 | 3% | 47 | FFDAGLVVFLPIIMT | 0 | 0 | 0 | 1 | 0 | 1 |
| 205 | 3% | 45 | TTSLAFLVAFRPGLV | 0 | 0 | 0 | 0 | 0 | 1 |
| 537 | 3% | 43 | VEPVDISNAVLFLAS | 0 | 1 | 1 | 0 | 0 | 0 |
| 543 | 3% | 43 | VIMPWMIFYQQGAVV | 0 | 1 | 1 | 0 | 1 | 0 |
| 1452 | 3% | 43 | TTPHFLVEGAIIAAY | 0 | 0 | 0 | 1 | 0 | 1 |
| 1393 | 3% | 42 | ANVRYISGAPQLWVV | 0 | 0 | 0 | 1 | 0 | 1 |
| 47 | 3% | 40 | VEFFRAVPVLIMMIF | 0 | 0 | 0 | 1 | 0 | 1 |
| 421 | 3% | 40 | DPAFRQVFAAQFLPD | 0 | 0 | 0 | 1 | 0 | 1 |
| 397 | 3% | 40 | ALMNQFISLLKASSL | 0 | 0 | 0 | 1 | 0 | 1 |

TABLE 2-continued

| | | | | | | | | | |
|---|---|---|---|---|---|---|---|---|---|
| 1368 | 3% | 40 | TMMLSLVWPIASLGF | 0 | 0 | 0 | 1 | 0 | 1 |
| 1141 | 3% | 38 | HAEYKQVTVLFADVV | 0 | 0 | 0 | 0 | 1 | 1 |
| 760 | 3% | 38 | AEWVVRTILSLLTVR | 1 | 0 | 0 | 0 | 0 | 0 |
| 787 | 3% | 38 | DVDIDQLRSFLADKV | 1 | 0 | 0 | 0 | 0 | 0 |
| 659 | 3% | 38 | GLLYVPQLATISATF | 0 | 0 | 0 | 1 | 0 | 1 |
| 323 | 3% | 38 | MIEMLAMSDLSLMVK | 0 | 1 | 1 | 0 | 1 | 0 |
| 629 | 3% | 37 | VQFMPLVIAPQLLLC | 0 | 0 | 0 | 0 | 0 | 1 |
| 586 | 3% | 37 | ELVWLGAAMIIGAGS | 0 | 1 | 1 | 0 | 1 | 0 |
| 1255 | 3% | 37 | GNELWQIALLELWLQ | 0 | 1 | 1 | 1 | 0 | 0 |
| 646 | 3% | 37 | ADAVNFGVAPAFIVY | 0 | 0 | 0 | 1 | 0 | 1 |
| 1072 | 3% | 37 | HIELALYRIAQECLQ | 0 | 0 | 0 | 1 | 0 | 1 |
| 1001 | 3% | 37 | KGGLRFHPSVYLGIV | 0 | 0 | 0 | 1 | 0 | 1 |
| 1244 | 3% | 35 | LIFDGVFDRFPTLRI | 0 | 1 | 1 | 0 | 1 | 1 |
| 1196 | 3% | 35 | MVWRAAAAIELGICD | 0 | 1 | 1 | 1 | 0 | 1 |
| 1132 | 3% | 35 | FLFTMLQKTLKGNIF | 1 | 0 | 0 | 0 | 0 | 1 |
| 745 | 3% | 35 | VFALMGLRQLYFLLG | 1 | 0 | 0 | 1 | 0 | 1 |
| 257 | 3% | 35 | FFHIYGMTVLLNAAL | 0 | 0 | 0 | 1 | 0 | 1 |
| 714 | 3% | 35 | AFTHFALLANVAEDI | 0 | 0 | 0 | 1 | 0 | 1 |
| 732 | 3% | 33 | PLRVAFLIVLIGTTV | 0 | 0 | 0 | 1 | 0 | 1 |
| 405 | 3% | 33 | PLVYFIDSMLQVDDL | 0 | 0 | 0 | 1 | 0 | 1 |
| 175 | 3% | 32 | LDYFLNLMLRAPFRL | 0 | 1 | 1 | 0 | 0 | 0 |
| 400 | 3% | 32 | MKELLAENLMVMMRD | 0 | 0 | 0 | 1 | 0 | 1 |
| 658 | 3% | 32 | VRRVLPALMNQFISL | 0 | 0 | 0 | 1 | 0 | 1 |
| 78 | 3% | 32 | IVGAALFLASDASSF | 0 | 1 | 1 | 0 | 1 | 0 |
| 538 | 3% | 30 | VEVVSAEALQLPLWG | 0 | 1 | 1 | 1 | 0 | 0 |
| 1204 | 3% | 30 | TPGLNLVYAHLNRII | 0 | 1 | 1 | 0 | 0 | 0 |
| 713 | 3% | 30 | EGELHLFTPEVVFLL | 0 | 0 | 0 | 1 | 0 | 1 |
| 1350 | 3% | 30 | LFFLFPLYAMADFST | 0 | 0 | 0 | 1 | 0 | 1 |
| 883 | 3% | 28 | EWFARILFSLFSTPS | 0 | 1 | 1 | 0 | 1 | 0 |
| 417 | 3% | 28 | GVVAAIIAYNYPNQL | 0 | 0 | 0 | 1 | 1 | 1 |
| 439 | 3% | 28 | GMVFQSFNLFAHKTI | 0 | 0 | 0 | 1 | 0 | 1 |
| 718 | 3% | 28 | LGPTAGLTVASALLV | 0 | 0 | 0 | 1 | 0 | 1 |
| 871 | 3% | 28 | LVYLVGFKTKVSTLL | 0 | 1 | 1 | 0 | 1 | 0 |
| 531 | 3% | 28 | LDSFQLFPNFVILFW | 0 | 1 | 1 | 1 | 0 | 0 |
| 88 | 3% | 28 | ALVLVSLLTALAAGI | 0 | 0 | 0 | 1 | 0 | 1 |
| 621 | 3% | 27 | AKVLGVFLVTEIVML | 0 | 0 | 0 | 0 | 0 | 1 |
| 1526 | 3% | 27 | VATVRAASSLVRAPL | 1 | 0 | 0 | 0 | 0 | 0 |
| 712 | 3% | 27 | VVLMIFRPQGLFPAR | 0 | 0 | 0 | 1 | 0 | 1 |
| 1004 | 3% | 27 | ARQMLRFLSSPLWRA | 0 | 0 | 0 | 1 | 0 | 1 |
| 865 | 3% | 25 | TPLFMAHYAPFGLLT | 0 | 1 | 1 | 0 | 1 | 0 |
| 540 | 3% | 25 | VVYAFMSLFVVNVVV | 0 | 1 | 1 | 0 | 1 | 0 |
| 1525 | 3% | 25 | FFHRGLMLMSFDEHL | 1 | 0 | 0 | 0 | 1 | 0 |
| 697 | 3% | 25 | RSLMFPTLASLIEER | 0 | 0 | 0 | 1 | 1 | 1 |
| 1284 | 3% | 25 | NAVLFLASDEARYIT | 0 | 0 | 0 | 0 | 0 | 1 |
| 963 | 3% | 25 | VLVVFLLPALRDGAP | 0 | 0 | 0 | 1 | 0 | 0 |
| 281 | 3% | 25 | IVAHYILQYATEELR | 1 | 0 | 0 | 0 | 0 | 0 |
| 438 | 3% | 25 | GSVLLVQALLVTSLL | 0 | 0 | 0 | 1 | 0 | 1 |
| 672 | 3% | 25 | ASGTLLFKLTPWIVV | 0 | 0 | 0 | 1 | 0 | 1 |
| 953 | 3% | 25 | FEHSVVNMFLFPSGL | 0 | 0 | 0 | 0 | 0 | 1 |
| 645 | 3% | 23 | PASILILFAPGAPRE | 0 | 0 | 0 | 1 | 1 | 0 |
| 691 | 3% | 23 | LANPGIVSIPLAFIL | 0 | 0 | 0 | 1 | 0 | 1 |
| 1474 | 3% | 23 | MFETMAAFMLVEHAN | 0 | 0 | 0 | 1 | 0 | 1 |
| 945 | 3% | 23 | ALIHVLWINAGLSCD | 0 | 0 | 0 | 0 | 0 | 1 |
| 898 | 3% | 23 | GQRVITLLASANRDE | 0 | 1 | 1 | 0 | 1 | 0 |
| 1529 | 3% | 23 | EGIVFALGGALDFSY | 1 | 0 | 0 | 0 | 0 | 0 |
| 1077 | 3% | 22 | GFVTEFLQREVQNFL | 1 | 0 | 0 | 0 | 0 | 1 |
| 1075 | 3% | 22 | SPEQAYLLLGAAPIE | 1 | 0 | 0 | 0 | 0 | 1 |
| 937 | 3% | 22 | HLMQSVVMVSFPVEV | 0 | 0 | 0 | 0 | 0 | 1 |
| 651 | 3% | 22 | FSWFAAGMVLAELTV | 0 | 0 | 0 | 1 | 0 | 1 |

| Peptide id | Mycobacterium_smegmatis_sp._JDM601 | Mycobacterium_sp._JLS | Mycobacterium_sp._kms | Mycobacterium_sp._MCS | Mycobacterium_sp._Spyr1 | Mycobacterium_ulcerans_Agy99 | Mycobacterium_vanbaalenii_PYR-1 | Mycobacterium_colombiense_CECT_3035 | Mycobacterium_parascrofulaceum_ATCC_BAA-614 | Total genomes conserved per peptide |
|---|---|---|---|---|---|---|---|---|---|---|
| 311 | 0 | 1 | 1 | 1 | 0 | 0 | 0 | 0 | 0 | 6 |
| 741 | 0 | 0 | 0 | 1 | 1 | 0 | 1 | 0 | 0 | 5 |
| 1364 | 0 | 1 | 1 | 1 | 1 | 0 | 1 | 0 | 0 | 7 |
| 446 | 0 | 0 | 0 | 0 | 1 | 0 | 1 | 0 | 1 | 5 |
| 329 | 1 | 1 | 1 | 1 | 0 | 1 | 1 | 1 | 1 | 12 |
| 582 | 0 | 1 | 1 | 1 | 0 | 0 | 0 | 0 | 0 | 5 |
| 7 | 0 | 1 | 1 | 1 | 0 | 1 | 0 | 1 | 1 | 9 |
| 720 | 0 | 1 | 1 | 1 | 1 | 0 | 1 | 0 | 1 | 7 |
| 1556 | 0 | 0 | 0 | 0 | 0 | 0 | 0 | 1 | 0 | 6 |
| 1224 | 0 | 0 | 0 | 0 | 0 | 0 | 0 | 1 | 1 | 5 |
| 829 | 0 | 0 | 0 | 0 | 0 | 0 | 0 | 1 | 1 | 5 |
| 777 | 0 | 1 | 1 | 1 | 0 | 0 | 0 | 0 | 1 | 6 |

TABLE 2-continued

| | | | | | | | | | | |
|---|---|---|---|---|---|---|---|---|---|---|
| 752 | 0 | 1 | 1 | 1 | 1 | 0 | 0 | 0 | 0 | 6 |
| 391 | 0 | 1 | 0 | 1 | 1 | 0 | 0 | 0 | 0 | 5 |
| 775 | 0 | 1 | 1 | 1 | 0 | 0 | 0 | 0 | 1 | 6 |
| 587 | 0 | 0 | 0 | 0 | 0 | 1 | 0 | 0 | 1 | 5 |
| 1258 | 0 | 1 | 0 | 1 | 1 | 0 | 1 | 0 | 1 | 9 |
| 868 | 0 | 0 | 0 | 0 | 0 | 1 | 0 | 1 | 0 | 5 |
| 1471 | 1 | 0 | 0 | 0 | 1 | 0 | 1 | 0 | 0 | 5 |
| 8 | 0 | 1 | 0 | 0 | 1 | 0 | 1 | 0 | 0 | 5 |
| 1331 | 1 | 1 | 1 | 0 | 1 | 0 | 0 | 0 | 0 | 5 |
| 804 | 0 | 1 | 1 | 1 | 0 | 0 | 0 | 0 | 0 | 6 |
| 106 | 0 | 1 | 1 | 1 | 1 | 0 | 0 | 0 | 0 | 6 |
| 424 | 0 | 1 | 1 | 1 | 1 | 0 | 0 | 0 | 0 | 6 |
| 1285 | 1 | 1 | 1 | 1 | 0 | 0 | 0 | 0 | 0 | 5 |
| 447 | 0 | 1 | 0 | 1 | 1 | 0 | 0 | 0 | 0 | 5 |
| 628 | 0 | 1 | 1 | 1 | 0 | 0 | 1 | 0 | 0 | 5 |
| 588 | 0 | 1 | 1 | 1 | 1 | 0 | 0 | 1 | 1 | 9 |
| 1542 | 0 | 0 | 0 | 0 | 0 | 0 | 0 | 1 | 0 | 5 |
| 841 | 0 | 0 | 0 | 0 | 0 | 0 | 0 | 1 | 1 | 5 |
| 1549 | 0 | 1 | 1 | 1 | 0 | 0 | 0 | 0 | 0 | 5 |
| 1571 | 0 | 1 | 1 | 1 | 0 | 0 | 1 | 0 | 0 | 5 |
| 1218 | 0 | 1 | 0 | 0 | 1 | 0 | 1 | 0 | 0 | 5 |
| 626 | 0 | 1 | 1 | 1 | 0 | 0 | 1 | 0 | 0 | 5 |
| 861 | 0 | 1 | 1 | 1 | 0 | 0 | 0 | 1 | 0 | 6 |
| 387 | 0 | 1 | 1 | 1 | 1 | 0 | 1 | 0 | 0 | 7 |
| 1134 | 0 | 1 | 1 | 1 | 0 | 1 | 1 | 0 | 0 | 6 |
| 1458 | 0 | 1 | 0 | 0 | 1 | 0 | 1 | 0 | 1 | 5 |
| 1334 | 0 | 1 | 0 | 1 | 1 | 0 | 0 | 0 | 0 | 5 |
| 205 | 0 | 1 | 1 | 1 | 0 | 0 | 1 | 0 | 0 | 5 |
| 537 | 0 | 0 | 0 | 0 | 0 | 0 | 1 | 1 | 1 | 5 |
| 543 | 0 | 0 | 0 | 0 | 0 | 1 | 0 | 1 | 0 | 5 |
| 1452 | 0 | 1 | 1 | 1 | 1 | 0 | 1 | 0 | 0 | 7 |
| 1393 | 0 | 1 | 1 | 1 | 1 | 0 | 1 | 0 | 0 | 7 |
| 47 | 0 | 1 | 1 | 1 | 1 | 0 | 1 | 0 | 0 | 7 |
| 421 | 0 | 1 | 1 | 1 | 1 | 0 | 1 | 0 | 0 | 7 |
| 397 | 0 | 1 | 1 | 0 | 1 | 0 | 0 | 0 | 0 | 5 |
| 1368 | 0 | 1 | 1 | 1 | 1 | 0 | 1 | 0 | 0 | 7 |
| 1141 | 0 | 1 | 1 | 1 | 0 | 0 | 0 | 0 | 1 | 6 |
| 760 | 0 | 1 | 1 | 1 | 0 | 0 | 0 | 0 | 1 | 5 |
| 787 | 0 | 1 | 1 | 1 | 0 | 0 | 0 | 0 | 1 | 5 |
| 659 | 0 | 1 | 1 | 1 | 1 | 0 | 0 | 0 | 0 | 6 |
| 323 | 1 | 0 | 0 | 0 | 0 | 1 | 0 | 1 | 1 | 7 |
| 629 | 0 | 1 | 1 | 1 | 0 | 0 | 1 | 0 | 0 | 5 |
| 586 | 0 | 0 | 0 | 0 | 0 | 1 | 0 | 0 | 1 | 5 |
| 1255 | 0 | 0 | 0 | 0 | 1 | 0 | 1 | 1 | 1 | 7 |
| 646 | 0 | 1 | 1 | 1 | 1 | 0 | 1 | 0 | 0 | 7 |
| 1072 | 0 | 1 | 1 | 1 | 1 | 0 | 1 | 0 | 0 | 7 |
| 1001 | 1 | 0 | 0 | 0 | 1 | 0 | 1 | 0 | 0 | 5 |
| 1244 | 0 | 0 | 0 | 0 | 0 | 0 | 0 | 0 | 1 | 5 |
| 1196 | 1 | 0 | 0 | 0 | 1 | 0 | 1 | 0 | 1 | 8 |
| 1132 | 1 | 1 | 1 | 1 | 0 | 0 | 0 | 0 | 0 | 6 |
| 745 | 0 | 0 | 0 | 0 | 1 | 0 | 1 | 0 | 0 | 5 |
| 257 | 0 | 1 | 1 | 1 | 1 | 0 | 1 | 0 | 0 | 7 |
| 714 | 0 | 1 | 1 | 1 | 1 | 0 | 1 | 0 | 0 | 7 |
| 732 | 0 | 1 | 1 | 1 | 1 | 0 | 1 | 0 | 0 | 7 |
| 405 | 0 | 1 | 1 | 1 | 1 | 0 | 0 | 0 | 0 | 6 |
| 175 | 0 | 1 | 1 | 1 | 0 | 0 | 0 | 0 | 0 | 5 |
| 400 | 0 | 1 | 1 | 1 | 1 | 0 | 1 | 0 | 0 | 7 |
| 658 | 0 | 1 | 1 | 0 | 1 | 0 | 0 | 0 | 0 | 5 |
| 78 | 0 | 0 | 0 | 0 | 0 | 1 | 0 | 1 | 0 | 5 |
| 538 | 0 | 0 | 0 | 0 | 1 | 0 | 1 | 1 | 0 | 6 |
| 1204 | 0 | 1 | 1 | 1 | 0 | 0 | 0 | 1 | 0 | 6 |
| 713 | 0 | 1 | 1 | 1 | 1 | 0 | 1 | 0 | 0 | 7 |
| 1350 | 0 | 1 | 1 | 1 | 0 | 0 | 1 | 0 | 0 | 6 |
| 883 | 0 | 0 | 0 | 0 | 0 | 1 | 0 | 1 | 1 | 6 |
| 417 | 0 | 1 | 1 | 1 | 1 | 0 | 1 | 0 | 1 | 9 |
| 439 | 0 | 1 | 1 | 1 | 1 | 0 | 1 | 0 | 0 | 7 |
| 718 | 0 | 1 | 1 | 1 | 1 | 0 | 0 | 0 | 0 | 6 |
| 871 | 0 | 0 | 0 | 0 | 0 | 1 | 0 | 0 | 1 | 5 |
| 531 | 0 | 0 | 0 | 0 | 1 | 0 | 0 | 1 | 0 | 5 |
| 88 | 0 | 1 | 0 | 1 | 1 | 0 | 0 | 0 | 0 | 5 |
| 621 | 0 | 1 | 1 | 1 | 0 | 0 | 1 | 0 | 0 | 5 |
| 1526 | 0 | 1 | 1 | 1 | 0 | 0 | 0 | 0 | 1 | 5 |
| 712 | 0 | 1 | 1 | 1 | 1 | 0 | 1 | 0 | 0 | 7 |
| 1004 | 0 | 1 | 1 | 1 | 1 | 0 | 1 | 0 | 0 | 7 |
| 865 | 0 | 0 | 0 | 0 | 0 | 1 | 0 | 1 | 1 | 6 |
| 540 | 1 | 0 | 0 | 0 | 0 | 0 | 0 | 1 | 1 | 6 |
| 1525 | 0 | 1 | 1 | 1 | 0 | 0 | 0 | 0 | 1 | 6 |
| 697 | 1 | 1 | 1 | 1 | 1 | 1 | 1 | 0 | 0 | 10 |
| 1284 | 0 | 1 | 1 | 1 | 0 | 0 | 1 | 1 | 1 | 7 |
| 963 | 0 | 0 | 0 | 0 | 1 | 0 | 1 | 1 | 1 | 5 |

TABLE 2-continued

| | | | | | | | | | | |
|---|---|---|---|---|---|---|---|---|---|---|
| 281 | 0 | 1 | 1 | 1 | 0 | 0 | 0 | 0 | 1 | 5 |
| 438 | 0 | 1 | 1 | 1 | 1 | 0 | 1 | 0 | 0 | 7 |
| 672 | 0 | 1 | 1 | 1 | 0 | 0 | 1 | 0 | 0 | 6 |
| 953 | 0 | 1 | 1 | 1 | 0 | 0 | 1 | 0 | 0 | 5 |
| 645 | 0 | 0 | 0 | 0 | 1 | 1 | 1 | 0 | 0 | 5 |
| 691 | 0 | 1 | 1 | 1 | 1 | 0 | 1 | 0 | 0 | 7 |
| 1474 | 0 | 1 | 1 | 1 | 1 | 0 | 1 | 0 | 0 | 7 |
| 945 | 0 | 1 | 1 | 1 | 0 | 0 | 1 | 0 | 0 | 5 |
| 898 | 0 | 0 | 0 | 0 | 0 | 1 | 0 | 1 | 1 | 6 |
| 1529 | 0 | 1 | 1 | 1 | 0 | 0 | 0 | 0 | 1 | 5 |
| 1077 | 0 | 1 | 1 | 1 | 0 | 0 | 1 | 0 | 0 | 6 |
| 1075 | 0 | 1 | 1 | 1 | 0 | 0 | 0 | 0 | 0 | 5 |
| 937 | 0 | 1 | 1 | 1 | 0 | 0 | 1 | 0 | 0 | 5 |
| 651 | 0 | 1 | 1 | 1 | 1 | 0 | 1 | 0 | 0 | 7 |

TABLE 3

| Count | OLD Peptide ID | Peptide | New Peptide ID | # resp IL-10 | IL-10 SFC | # tested | # resp IFNg | IFNg SFC |
|---|---|---|---|---|---|---|---|---|
| 1 | 3330.0266 | AELTRVRQQVIQLLS | 3580.0001 | 4 | 733 | 6 | 0 | 27 |
| 2 | 3330.1344 | ESFLFYSGFYLPMYW | 3580.0002 | 4 | 570 | 6 | 0 | 8 |
| 3 | 3330.1605 | FVTYWSFRMMIGLMA | 3580.0003 | 4 | 563 | 5 | 0 | 10 |
| 4 | 3330.3163 | FTGKPEFVENFFMFI | 3580.0004 | 3 | 622 | 6 | 0 | 27 |
| 5 | 3330.6228 | APFISEFLVLLGTFS | 3580.0005 | 3 | 585 | 6 | 0 | 15 |
| 6 | 3330.6614 | FAIMFEALFILTTVD | 3580.0006 | 5 | 915 | 5 | 0 | 32 |
| 7 | 3330.6719 | LPFFSFMTYLIAVPT | 3580.0007 | 4 | 505 | 5 | 0 | 22 |
| 8 | 3330.6721 | ATFAGIYFWFPKMTG | 3580.0008 | 6 | 1328 | 6 | 0 | 28 |
| 9 | 3331.0389 | DRIAQLLVQRVELVE | 3580.0009 | 5 | 1018 | 6 | 0 | 50 |
| 10 | 3331.0582 | AKSVLIFLGIPLLAG | 3580.0010 | 4 | 892 | 5 | 0 | 35 |
| 11 | 3331.0598 | GRFIALLRIFAGPLA | 3580.0011 | 5 | 1480 | 5 | 0 | 52 |
| 12 | 3331.2091 | IGQFGIGFYSSFMVA | 3580.0012 | 3 | 468 | 5 | 0 | 10 |
| 13 | 3331.3806 | ASVSKQFTATAILLL | 3580.0013 | 4 | 918 | 5 | 0 | 23 |
| 14 | 3332.1307 | YVLFLFTQTVRHRDF | 3580.0014 | 4 | 975 | 5 | 0 | 53 |
| 15 | 3332.1361 | ASCKYMKMITPAALL | 3580.0015 | 4 | 730 | 5 | 0 | 32 |
| 16 | 3332.1984 | LAMFAIIFFWTPPHT | 3580.0016 | 5 | 1142 | 6 | 0 | 27 |
| 17 | 3332.2157 | MVAFMVRYTSGYLCV | 3580.0017 | 4 | 1058 | 5 | 0 | 8 |
| 18 | 3332.2491 | ASGLIFGWLAFLLVF | 3580.0018 | 4 | 652 | 5 | 0 | 20 |
| 19 | 3332.2678 | RELIRAFWPGALSLV | 3580.0019 | 3 | 422 | 5 | 0 | 27 |
| 20 | 3332.3902 | LSSTEFELLRFLMRN | 3580.0020 | 5 | 1017 | 6 | 0 | 33 |

TABLE 4

Selected NTM Pool

| Peptide id | Resp freq | Total SFC | Peptides \| Organism → | Mycobacterium abscessus | Mycobacterium avium_ 104 | Mycobacterium_ avium_ subsps_ paratuberculosis_ k_10 | Mycobacterium_ gilvum_ PYR-GCK | Mycobacterium_ marinum_M | Mycobacterium_ smegmatis_ str._ MC2_155 | Mycobacterium_ sp._ JDM601 |
|---|---|---|---|---|---|---|---|---|---|---|
| 311 | 3% | 477 | RFTLLRPLLFTIAYE | 0 | 1 | 1 | 0 | 1 | 0 | 0 |
| 741 | 13% | 248 | KWETFLTQELPAYLA | 1 | 0 | 0 | 1 | 0 | 0 | 0 |
| 1364 | 3% | 228 | PLAENYLRLNALGAY | 0 | 0 | 0 | 1 | 0 | 1 | 0 |

TABLE 4-continued

Selected NTM Pool

| | | | | | | | | | | |
|---|---|---|---|---|---|---|---|---|---|---|
| 446 | 3% | 182 | HEEIQLLANDFSTML | 0 | 0 | 0 | 1 | 1 | 0 | 0 |
| 329 | 7% | 167 | SLHMFFHRLGPVLAR | 0 | 1 | 1 | 0 | 1 | 1 | 1 |
| 582 | 10% | 158 | RLFPVIRRYALAYHV | 0 | 1 | 1 | 0 | 0 | 0 | 0 |
| 7 | 3% | 138 | LMVLFQYGVALHELE | 0 | 0 | 1 | 0 | 1 | 1 | 0 |
| 720 | 10% | 125 | DPLIFFRPRVERLFG | 0 | 0 | 0 | 1 | 0 | 0 | 0 |
| 1556 | 3% | 122 | YNVVIYPVTTLRLAM | 1 | 1 | 1 | 0 | 1 | 1 | 0 |
| 1224 | 10% | 97 | LMLIWACDLIVAADN | 0 | 1 | 1 | 0 | 1 | 0 | 0 |
| 829 | 3% | 93 | ETTRNLIALGTLALI | 0 | 1 | 1 | 1 | 0 | 0 | 0 |
| 777 | 7% | 87 | ALLYIPLLTRMLMNL | 1 | 0 | 0 | 0 | 1 | 0 | 0 |
| 752 | 3% | 78 | KDVFFYEPIILPEKS | 1 | 0 | 0 | 1 | 0 | 0 | 0 |
| 391 | 3% | 77 | LGVAALLFGFPIFFD | 0 | 0 | 0 | 1 | 0 | 1 | 0 |
| 775 | 7% | 70 | PKLKQFMSDVVWIEH | 1 | 0 | 0 | 0 | 1 | 0 | 0 |
| 587 | 7% | 68 | GSMLWVAALIGEEIF | 0 | 1 | 1 | 0 | 1 | 0 | 0 |
| 1258 | 3% | 60 | GRLIGWLAKVLAEHP | 0 | 1 | 1 | 0 | 1 | 1 | 0 |
| 868 | 3% | 58 | QWGYRMVLPQLILMP | 0 | 1 | 1 | 0 | 1 | 0 | 0 |
| 1471 | 7% | 58 | SQRLVTLSYRLDAAA | 0 | 0 | 0 | 1 | 0 | 1 | 1 |
| 8 | 3% | 58 | HQGLAFLLADMAAAV | 0 | 1 | 0 | 1 | 0 | 0 | 0 |

| Peptide id | Mycobac-terium_sp._JLS | Mycobac-terium_sp._KMS | Mycobac-terium_sp._MCS | Mycobac-terium_sp._Spyr1 | Mycobac-terium_ulcerans_Agy99 | Mycobac-terium_vanbaa-lenii_PYR-1 | Mycobac-terium_colombi-ense_CECT_3035 | Mycobac-terium_parascro-fulaceum_ATCC_BAA-614 | Total genomes con served per peptide |
|---|---|---|---|---|---|---|---|---|---|
| 311 | 1 | 1 | 1 | 0 | 0 | 0 | 0 | 0 | 6 |
| 741 | 0 | 0 | 1 | 1 | 0 | 1 | 0 | 0 | 5 |
| 1364 | 1 | 1 | 1 | 1 | 0 | 1 | 0 | 0 | 7 |
| 446 | 0 | 0 | 0 | 1 | 0 | 1 | 0 | 1 | 5 |
| 329 | 1 | 1 | 1 | 0 | 1 | 1 | 1 | 1 | 12 |
| 582 | 1 | 1 | 1 | 0 | 0 | 0 | 0 | 0 | 5 |
| 7 | 1 | 1 | 1 | 0 | 1 | 0 | 1 | 1 | 9 |
| 720 | 1 | 1 | 1 | 1 | 0 | 1 | 0 | 1 | 7 |
| 1556 | 0 | 0 | 0 | 0 | 0 | 0 | 1 | 0 | 6 |
| 1224 | 0 | 0 | 0 | 0 | 0 | 0 | 1 | 1 | 5 |
| 829 | 0 | 0 | 0 | 0 | 0 | 0 | 1 | 1 | 5 |
| 777 | 1 | 1 | 1 | 0 | 0 | 0 | 0 | 1 | 6 |
| 752 | 1 | 1 | 1 | 1 | 0 | 0 | 0 | 0 | 6 |
| 391 | 1 | 0 | 1 | 1 | 0 | 0 | 0 | 0 | 5 |
| 775 | 1 | 1 | 1 | 0 | 0 | 0 | 0 | 1 | 6 |
| 587 | 0 | 0 | 0 | 0 | 1 | 0 | 0 | 1 | 5 |
| 1258 | 1 | 0 | 1 | 1 | 0 | 1 | 0 | 1 | 9 |
| 868 | 0 | 0 | 0 | 0 | 1 | 0 | 1 | 0 | 5 |
| 1471 | 0 | 0 | 0 | 1 | 0 | 1 | 0 | 0 | 5 |
| 8 | 1 | 0 | 0 | 1 | 0 | 1 | 0 | 0 | 5 |

What is claimed:

1. A method of modulating an immune response, comprising administration of an effective amount of an antagonist of Th* cell activity, wherein the method comprises modulating expression or activity of IL23R, and wherein the method reduces the immune response.

2. The method of claim 1, wherein the method treats the cavitation phase of *Mycobacterium tuberculosis* infection.

3. The method of claim 1, wherein the method comprise reducing the immune response to treat an aberrant immune response.

* * * * *

SEQUENCE LISTING

<160> NUMBER OF SEQ ID NOS: 126

<210> SEQ ID NO 1
<211> LENGTH: 15
<212> TYPE: PRT
<213> ORGANISM: Mycobacterium tuberculosis

<400> SEQUENCE: 1

Arg Phe Thr Leu Leu Arg Pro Leu Leu Phe Thr Ile Ala Tyr Glu
1 5 10 15

<210> SEQ ID NO 2
<211> LENGTH: 15
<212> TYPE: PRT
<213> ORGANISM: Mycobacterium tuberculosis

<400> SEQUENCE: 2

Lys Trp Glu Thr Phe Leu Thr Gln Glu Leu Pro Ala Tyr Leu Ala
1 5 10 15

<210> SEQ ID NO 3

<211> LENGTH: 15
<212> TYPE: PRT
<213> ORGANISM: Mycobacterium tuberculosis

<400> SEQUENCE: 3

Pro Leu Ala Glu Asn Tyr Leu Arg Leu Asn Ala Leu Gly Ala Tyr
1 5 10 15

<210> SEQ ID NO 4
<211> LENGTH: 15
<212> TYPE: PRT
<213> ORGANISM: Mycobacterium tuberculosis

<400> SEQUENCE: 4

His Glu Glu Ile Gln Leu Leu Ala Asn Asp Phe Ser Thr Met Leu
1 5 10 15

<210> SEQ ID NO 5
<211> LENGTH: 15
<212> TYPE: PRT
<213> ORGANISM: Mycobacterium tuberculosis

<400> SEQUENCE: 5

Ser Leu His Met Phe Phe His Arg Leu Gly Pro Val Leu Ala Arg
1 5 10 15

<210> SEQ ID NO 6
<211> LENGTH: 15
<212> TYPE: PRT
<213> ORGANISM: Mycobacterium tuberculosis

<400> SEQUENCE: 6

Arg Leu Phe Pro Val Ile Arg Arg Tyr Ala Leu Ala Tyr His Val
1 5 10 15

<210> SEQ ID NO 7
<211> LENGTH: 15
<212> TYPE: PRT
<213> ORGANISM: Mycobacterium tuberculosis

<400> SEQUENCE: 7

Leu Met Val Leu Phe Gln Tyr Gly Val Ala Leu His Glu Leu Glu
1 5 10 15

<210> SEQ ID NO 8
<211> LENGTH: 15
<212> TYPE: PRT
<213> ORGANISM: Mycobacterium tuberculosis

<400> SEQUENCE: 8

Asp Pro Leu Ile Phe Phe Arg Pro Arg Val Glu Arg Leu Phe Gly
1 5 10 15

<210> SEQ ID NO 9
<211> LENGTH: 15
<212> TYPE: PRT
<213> ORGANISM: Mycobacterium tuberculosis

<400> SEQUENCE: 9

Tyr Asn Val Val Ile Tyr Pro Val Thr Thr Leu Arg Leu Ala Met
1 5 10 15

<210> SEQ ID NO 10
<211> LENGTH: 15
<212> TYPE: PRT

<213> ORGANISM: Mycobacterium tuberculosis

<400> SEQUENCE: 10

Leu Met Leu Ile Trp Ala Cys Asp Leu Ile Val Ala Ala Asp Asn
1 5 10 15

<210> SEQ ID NO 11
<211> LENGTH: 15
<212> TYPE: PRT
<213> ORGANISM: Mycobacterium tuberculosis

<400> SEQUENCE: 11

Glu Thr Thr Arg Asn Leu Ile Ala Leu Gly Thr Leu Ala Leu Ile
1 5 10 15

<210> SEQ ID NO 12
<211> LENGTH: 15
<212> TYPE: PRT
<213> ORGANISM: Mycobacterium tuberculosis

<400> SEQUENCE: 12

Ala Leu Leu Tyr Ile Pro Leu Leu Thr Arg Met Leu Met Asn Leu
1 5 10 15

<210> SEQ ID NO 13
<211> LENGTH: 15
<212> TYPE: PRT
<213> ORGANISM: Mycobacterium tuberculosis

<400> SEQUENCE: 13

Lys Asp Val Phe Phe Tyr Glu Pro Ile Ile Leu Pro Glu Lys Ser
1 5 10 15

<210> SEQ ID NO 14
<211> LENGTH: 15
<212> TYPE: PRT
<213> ORGANISM: Mycobacterium tuberculosis

<400> SEQUENCE: 14

Leu Gly Val Ala Ala Leu Leu Phe Gly Phe Pro Ile Phe Phe Asp
1 5 10 15

<210> SEQ ID NO 15
<211> LENGTH: 15
<212> TYPE: PRT
<213> ORGANISM: Mycobacterium tuberculosis

<400> SEQUENCE: 15

Pro Lys Leu Lys Gln Phe Met Ser Asp Val Val Trp Ile Glu His
1 5 10 15

<210> SEQ ID NO 16
<211> LENGTH: 15
<212> TYPE: PRT
<213> ORGANISM: Mycobacterium tuberculosis

<400> SEQUENCE: 16

Gly Ser Met Leu Trp Val Ala Ala Leu Ile Gly Glu Glu Ile Phe
1 5 10 15

<210> SEQ ID NO 17
<211> LENGTH: 15
<212> TYPE: PRT
<213> ORGANISM: Mycobacterium tuberculosis -continued

<400> SEQUENCE: 17

Gly Arg Leu Ile Gly Trp Leu Ala Lys Val Leu Ala Glu His Pro
1 5 10 15

<210> SEQ ID NO 18
<211> LENGTH: 15
<212> TYPE: PRT
<213> ORGANISM: Mycobacterium tuberculosis

<400> SEQUENCE: 18

Gln Trp Gly Tyr Arg Met Val Leu Pro Gln Leu Ile Leu Met Pro
1 5 10 15

<210> SEQ ID NO 19
<211> LENGTH: 15
<212> TYPE: PRT
<213> ORGANISM: Mycobacterium tuberculosis

<400> SEQUENCE: 19

Ser Gln Arg Leu Val Thr Leu Ser Tyr Arg Leu Asp Ala Ala Ala
1 5 10 15

<210> SEQ ID NO 20
<211> LENGTH: 15
<212> TYPE: PRT
<213> ORGANISM: Mycobacterium tuberculosis

<400> SEQUENCE: 20

His Gln Gly Leu Ala Phe Leu Leu Ala Asp Met Ala Ala Ala Val
1 5 10 15

<210> SEQ ID NO 21
<211> LENGTH: 15
<212> TYPE: PRT
<213> ORGANISM: Mycobacterium tuberculosis

<400> SEQUENCE: 21

Val Glu Ala Gly Met Val Tyr Val Thr Leu Pro Pro Leu Phe Val
1 5 10 15

<210> SEQ ID NO 22
<211> LENGTH: 15
<212> TYPE: PRT
<213> ORGANISM: Mycobacterium tuberculosis

<400> SEQUENCE: 22

Asn Ser Ser Ile Val Leu Ile Ser Leu Pro Ala Ile Phe Arg Gly
1 5 10 15

<210> SEQ ID NO 23
<211> LENGTH: 15
<212> TYPE: PRT
<213> ORGANISM: Mycobacterium tuberculosis

<400> SEQUENCE: 23

Gly Leu Ser Ser Ala Trp Leu Ser Leu Ile Phe Ala Glu Met Ile
1 5 10 15

<210> SEQ ID NO 24
<211> LENGTH: 15
<212> TYPE: PRT
<213> ORGANISM: Mycobacterium tuberculosis

<400> SEQUENCE: 24

-continued

Ala Val Pro Asn Phe Ala Leu Thr Pro Leu Leu Ile Ile Trp Met
1 5 10 15

<210> SEQ ID NO 25
<211> LENGTH: 15
<212> TYPE: PRT
<213> ORGANISM: Mycobacterium tuberculosis

<400> SEQUENCE: 25

Pro Ala Asp Ala Ser Ile Val Lys Leu Tyr Tyr Ser Glu Leu Leu
1 5 10 15

<210> SEQ ID NO 26
<211> LENGTH: 15
<212> TYPE: PRT
<213> ORGANISM: Mycobacterium tuberculosis

<400> SEQUENCE: 26

Asp Asp Arg Arg Thr Leu Leu Trp Leu Ala Asn Gln Arg Ala Val
1 5 10 15

<210> SEQ ID NO 27
<211> LENGTH: 15
<212> TYPE: PRT
<213> ORGANISM: Mycobacterium tuberculosis

<400> SEQUENCE: 27

Leu Gly Val Phe Pro Leu Ile Val Met Phe Leu Ile Thr Ser Ile
1 5 10 15

<210> SEQ ID NO 28
<211> LENGTH: 15
<212> TYPE: PRT
<213> ORGANISM: Mycobacterium tuberculosis

<400> SEQUENCE: 28

His Leu Phe Gln Val Met Ala Phe Val Val Met Glu Pro Pro Thr
1 5 10 15

<210> SEQ ID NO 29
<211> LENGTH: 15
<212> TYPE: PRT
<213> ORGANISM: Mycobacterium tuberculosis

<400> SEQUENCE: 29

Gly Arg Val Ala Trp Asn Ile Val Thr Ser Tyr Leu Asp Ser Ala
1 5 10 15

<210> SEQ ID NO 30
<211> LENGTH: 15
<212> TYPE: PRT
<213> ORGANISM: Mycobacterium tuberculosis

<400> SEQUENCE: 30

Pro Gln Phe Leu Ile Met Pro Lys Leu Ile Pro Ala Leu Ile Ala
1 5 10 15

<210> SEQ ID NO 31
<211> LENGTH: 15
<212> TYPE: PRT
<213> ORGANISM: Mycobacterium tuberculosis

<400> SEQUENCE: 31

Arg Ile Leu Gln Val Phe Thr Glu Ala Tyr Ala Asp Val Glu Arg
1 5 10 15

<210> SEQ ID NO 32
<211> LENGTH: 15
<212> TYPE: PRT
<213> ORGANISM: Mycobacterium tuberculosis

<400> SEQUENCE: 32

Ala Asp Gly Leu Val Leu Phe Asn Arg Phe Leu Gln Pro Asp Ile
1 5 10 15

<210> SEQ ID NO 33
<211> LENGTH: 15
<212> TYPE: PRT
<213> ORGANISM: Mycobacterium tuberculosis

<400> SEQUENCE: 33

Arg Thr Phe Phe Arg Tyr Phe Pro Thr Lys Glu Ser Val Leu Phe
1 5 10 15

<210> SEQ ID NO 34
<211> LENGTH: 15
<212> TYPE: PRT
<213> ORGANISM: Mycobacterium tuberculosis

<400> SEQUENCE: 34

Ala Arg Ala Gly Phe Ala Ala Ser Gly Val Leu His Leu Leu Val
1 5 10 15

<210> SEQ ID NO 35
<211> LENGTH: 15
<212> TYPE: PRT
<213> ORGANISM: Mycobacterium tuberculosis

<400> SEQUENCE: 35

Met Val Phe Ala Thr Leu Leu Pro Leu Gly Val Leu Gln Leu Tyr
1 5 10 15

<210> SEQ ID NO 36
<211> LENGTH: 15
<212> TYPE: PRT
<213> ORGANISM: Mycobacterium tuberculosis

<400> SEQUENCE: 36

Arg Gly Gln Phe Trp Ile Trp Ala Gly Ala Asn Ile Ala Pro Ile
1 5 10 15

<210> SEQ ID NO 37
<211> LENGTH: 15
<212> TYPE: PRT
<213> ORGANISM: Mycobacterium tuberculosis

<400> SEQUENCE: 37

Thr Leu Leu Thr Met Leu Trp Gln Asn Leu Ile Gly Asn Ala Val
1 5 10 15

<210> SEQ ID NO 38
<211> LENGTH: 15
<212> TYPE: PRT
<213> ORGANISM: Mycobacterium tuberculosis

<400> SEQUENCE: 38

His Phe Val Ser Thr Leu Ser Ala Thr Phe Pro Glu Gly Glu Asp
1 5 10 15

-continued

<210> SEQ ID NO 39
<211> LENGTH: 15
<212> TYPE: PRT
<213> ORGANISM: Mycobacterium tuberculosis

<400> SEQUENCE: 39

Phe Phe Asp Ala Gly Leu Val Val Phe Leu Pro Ile Ile Met Thr
1 5 10 15

<210> SEQ ID NO 40
<211> LENGTH: 15
<212> TYPE: PRT
<213> ORGANISM: Mycobacterium tuberculosis

<400> SEQUENCE: 40

Thr Thr Ser Leu Ala Phe Leu Val Ala Phe Arg Pro Gly Leu Val
1 5 10 15

<210> SEQ ID NO 41
<211> LENGTH: 15
<212> TYPE: PRT
<213> ORGANISM: Mycobacterium tuberculosis

<400> SEQUENCE: 41

Val Glu Pro Val Asp Ile Ser Asn Ala Val Leu Phe Leu Ala Ser
1 5 10 15

<210> SEQ ID NO 42
<211> LENGTH: 15
<212> TYPE: PRT
<213> ORGANISM: Mycobacterium tuberculosis

<400> SEQUENCE: 42

Val Ile Met Pro Trp Met Ile Phe Tyr Gln Gln Gly Ala Val Val
1 5 10 15

<210> SEQ ID NO 43
<211> LENGTH: 15
<212> TYPE: PRT
<213> ORGANISM: Mycobacterium tuberculosis

<400> SEQUENCE: 43

Thr Thr Pro His Phe Leu Val Glu Gly Ala Ile Ile Ala Ala Tyr
1 5 10 15

<210> SEQ ID NO 44
<211> LENGTH: 15
<212> TYPE: PRT
<213> ORGANISM: Mycobacterium tuberculosis

<400> SEQUENCE: 44

Ala Asn Val Arg Tyr Ile Ser Gly Ala Pro Gln Leu Trp Val Val
1 5 10 15

<210> SEQ ID NO 45
<211> LENGTH: 15
<212> TYPE: PRT
<213> ORGANISM: Mycobacterium tuberculosis

<400> SEQUENCE: 45

Val Glu Phe Phe Arg Ala Val Pro Val Leu Ile Met Met Ile Phe
1 5 10 15

<210> SEQ ID NO 46
<211> LENGTH: 15

<212> TYPE: PRT
<213> ORGANISM: Mycobacterium tuberculosis

<400> SEQUENCE: 46

Asp Pro Ala Phe Arg Gln Val Phe Ala Ala Gln Phe Leu Pro Asp
1 5 10 15

<210> SEQ ID NO 47
<211> LENGTH: 15
<212> TYPE: PRT
<213> ORGANISM: Mycobacterium tuberculosis

<400> SEQUENCE: 47

Ala Leu Met Asn Gln Phe Ile Ser Leu Leu Lys Ala Ser Ser Leu
1 5 10 15

<210> SEQ ID NO 48
<211> LENGTH: 15
<212> TYPE: PRT
<213> ORGANISM: Mycobacterium tuberculosis

<400> SEQUENCE: 48

Thr Met Met Leu Ser Leu Val Trp Pro Ile Ala Ser Leu Gly Phe
1 5 10 15

<210> SEQ ID NO 49
<211> LENGTH: 15
<212> TYPE: PRT
<213> ORGANISM: Mycobacterium tuberculosis

<400> SEQUENCE: 49

His Ala Glu Tyr Lys Gln Val Thr Val Leu Phe Ala Asp Val Val
1 5 10 15

<210> SEQ ID NO 50
<211> LENGTH: 15
<212> TYPE: PRT
<213> ORGANISM: Mycobacterium tuberculosis

<400> SEQUENCE: 50

Ala Glu Trp Val Val Arg Thr Ile Leu Ser Leu Leu Thr Val Arg
1 5 10 15

<210> SEQ ID NO 51
<211> LENGTH: 15
<212> TYPE: PRT
<213> ORGANISM: Mycobacterium tuberculosis

<400> SEQUENCE: 51

Asp Val Asp Ile Asp Gln Leu Arg Ser Phe Leu Ala Asp Lys Val
1 5 10 15

<210> SEQ ID NO 52
<211> LENGTH: 15
<212> TYPE: PRT
<213> ORGANISM: Mycobacterium tuberculosis

<400> SEQUENCE: 52

Gly Leu Leu Tyr Val Pro Gln Leu Ala Thr Ile Ser Ala Thr Phe
1 5 10 15

<210> SEQ ID NO 53
<211> LENGTH: 15
<212> TYPE: PRT
<213> ORGANISM: Mycobacterium tuberculosis

<400> SEQUENCE: 53

Met Ile Glu Met Leu Ala Met Ser Asp Leu Ser Leu Met Val Lys
1               5                   10                  15

<210> SEQ ID NO 54
<211> LENGTH: 15
<212> TYPE: PRT
<213> ORGANISM: Mycobacterium tuberculosis

<400> SEQUENCE: 54

Val Gln Phe Met Pro Leu Val Ile Ala Pro Gln Leu Leu Leu Cys
1               5                   10                  15

<210> SEQ ID NO 55
<211> LENGTH: 15
<212> TYPE: PRT
<213> ORGANISM: Mycobacterium tuberculosis

<400> SEQUENCE: 55

Glu Leu Val Trp Leu Gly Ala Ala Met Ile Ile Gly Ala Gly Ser
1               5                   10                  15

<210> SEQ ID NO 56
<211> LENGTH: 15
<212> TYPE: PRT
<213> ORGANISM: Mycobacterium tuberculosis

<400> SEQUENCE: 56

Gly Asn Glu Leu Trp Gln Ile Ala Leu Leu Glu Leu Trp Leu Gln
1               5                   10                  15

<210> SEQ ID NO 57
<211> LENGTH: 15
<212> TYPE: PRT
<213> ORGANISM: Mycobacterium tuberculosis

<400> SEQUENCE: 57

Ala Asp Ala Val Asn Phe Gly Val Ala Pro Ala Phe Ile Val Tyr
1               5                   10                  15

<210> SEQ ID NO 58
<211> LENGTH: 15
<212> TYPE: PRT
<213> ORGANISM: Mycobacterium tuberculosis

<400> SEQUENCE: 58

His Ile Glu Leu Ala Leu Tyr Arg Ile Ala Gln Glu Cys Leu Gln
1               5                   10                  15

<210> SEQ ID NO 59
<211> LENGTH: 15
<212> TYPE: PRT
<213> ORGANISM: Mycobacterium tuberculosis

<400> SEQUENCE: 59

Lys Gly Gly Leu Arg Phe His Pro Ser Val Tyr Leu Gly Ile Val
1               5                   10                  15

<210> SEQ ID NO 60
<211> LENGTH: 15
<212> TYPE: PRT
<213> ORGANISM: Mycobacterium tuberculosis

<400> SEQUENCE: 60

Leu Ile Phe Asp Gly Val Phe Asp Arg Phe Pro Thr Leu Arg Ile
1 5 10 15

<210> SEQ ID NO 61
<211> LENGTH: 15
<212> TYPE: PRT
<213> ORGANISM: Mycobacterium tuberculosis

<400> SEQUENCE: 61

Met Val Trp Arg Ala Ala Ala Ala Ile Glu Leu Gly Ile Cys Asp
1 5 10 15

<210> SEQ ID NO 62
<211> LENGTH: 15
<212> TYPE: PRT
<213> ORGANISM: Mycobacterium tuberculosis

<400> SEQUENCE: 62

Phe Leu Phe Thr Met Leu Gln Lys Thr Leu Lys Gly Asn Ile Phe
1 5 10 15

<210> SEQ ID NO 63
<211> LENGTH: 15
<212> TYPE: PRT
<213> ORGANISM: Mycobacterium tuberculosis

<400> SEQUENCE: 63

Val Phe Ala Leu Met Gly Leu Arg Gln Leu Tyr Phe Leu Leu Gly
1 5 10 15

<210> SEQ ID NO 64
<211> LENGTH: 15
<212> TYPE: PRT
<213> ORGANISM: Mycobacterium tuberculosis

<400> SEQUENCE: 64

Phe Phe His Ile Tyr Gly Met Thr Val Leu Leu Asn Ala Ala Leu
1 5 10 15

<210> SEQ ID NO 65
<211> LENGTH: 15
<212> TYPE: PRT
<213> ORGANISM: Mycobacterium tuberculosis

<400> SEQUENCE: 65

Ala Phe Thr His Phe Ala Leu Leu Ala Asn Val Ala Glu Asp Ile
1 5 10 15

<210> SEQ ID NO 66
<211> LENGTH: 15
<212> TYPE: PRT
<213> ORGANISM: Mycobacterium tuberculosis

<400> SEQUENCE: 66

Pro Leu Arg Val Ala Phe Leu Ile Val Leu Ile Gly Thr Thr Val
1 5 10 15

<210> SEQ ID NO 67
<211> LENGTH: 15
<212> TYPE: PRT
<213> ORGANISM: Mycobacterium tuberculosis

<400> SEQUENCE: 67

Pro Leu Val Tyr Phe Ile Asp Ser Met Leu Gln Val Asp Asp Leu 1 5 10 15

<210> SEQ ID NO 68
<211> LENGTH: 15
<212> TYPE: PRT
<213> ORGANISM: Mycobacterium tuberculosis

<400> SEQUENCE: 68

Leu Asp Tyr Phe Leu Asn Leu Met Leu Arg Ala Pro Phe Arg Leu
1 5 10 15

<210> SEQ ID NO 69
<211> LENGTH: 15
<212> TYPE: PRT
<213> ORGANISM: Mycobacterium tuberculosis

<400> SEQUENCE: 69

Met Lys Glu Leu Leu Ala Glu Asn Leu Met Val Met Met Arg Asp
1 5 10 15

<210> SEQ ID NO 70
<211> LENGTH: 15
<212> TYPE: PRT
<213> ORGANISM: Mycobacterium tuberculosis

<400> SEQUENCE: 70

Val Arg Arg Val Leu Pro Ala Leu Met Asn Gln Phe Ile Ser Leu
1 5 10 15

<210> SEQ ID NO 71
<211> LENGTH: 15
<212> TYPE: PRT
<213> ORGANISM: Mycobacterium tuberculosis

<400> SEQUENCE: 71

Ile Val Gly Ala Ala Leu Phe Leu Ala Ser Asp Ala Ser Ser Phe
1 5 10 15

<210> SEQ ID NO 72
<211> LENGTH: 15
<212> TYPE: PRT
<213> ORGANISM: Mycobacterium tuberculosis

<400> SEQUENCE: 72

Val Glu Val Val Ser Ala Glu Ala Leu Gln Leu Pro Leu Trp Gly
1 5 10 15

<210> SEQ ID NO 73
<211> LENGTH: 15
<212> TYPE: PRT
<213> ORGANISM: Mycobacterium tuberculosis

<400> SEQUENCE: 73

Thr Pro Gly Leu Asn Leu Val Tyr Ala His Leu Asn Arg Ile Ile
1 5 10 15

<210> SEQ ID NO 74
<211> LENGTH: 15
<212> TYPE: PRT
<213> ORGANISM: Mycobacterium tuberculosis

<400> SEQUENCE: 74

Glu Gly Glu Leu His Leu Phe Thr Pro Glu Val Val Phe Leu Leu
1 5 10 15

<210> SEQ ID NO 75
<211> LENGTH: 15
<212> TYPE: PRT
<213> ORGANISM: Mycobacterium tuberculosis

<400> SEQUENCE: 75

Leu Phe Phe Leu Phe Pro Leu Tyr Ala Met Ala Asp Phe Ser Thr
1               5                   10                  15

<210> SEQ ID NO 76
<211> LENGTH: 15
<212> TYPE: PRT
<213> ORGANISM: Mycobacterium tuberculosis

<400> SEQUENCE: 76

Glu Trp Phe Ala Arg Ile Leu Phe Ser Leu Phe Ser Thr Pro Ser
1               5                   10                  15

<210> SEQ ID NO 77
<211> LENGTH: 15
<212> TYPE: PRT
<213> ORGANISM: Mycobacterium tuberculosis

<400> SEQUENCE: 77

Gly Val Val Ala Ala Ile Ile Ala Tyr Asn Tyr Pro Asn Gln Leu
1               5                   10                  15

<210> SEQ ID NO 78
<211> LENGTH: 15
<212> TYPE: PRT
<213> ORGANISM: Mycobacterium tuberculosis

<400> SEQUENCE: 78

Gly Met Val Phe Gln Ser Phe Asn Leu Phe Ala His Lys Thr Ile
1               5                   10                  15

<210> SEQ ID NO 79
<211> LENGTH: 15
<212> TYPE: PRT
<213> ORGANISM: Mycobacterium tuberculosis

<400> SEQUENCE: 79

Leu Gly Pro Thr Ala Gly Leu Thr Val Ala Ser Ala Leu Leu Val
1               5                   10                  15

<210> SEQ ID NO 80
<211> LENGTH: 15
<212> TYPE: PRT
<213> ORGANISM: Mycobacterium tuberculosis

<400> SEQUENCE: 80

Leu Val Tyr Leu Val Gly Phe Lys Thr Lys Val Ser Thr Leu Leu
1               5                   10                  15

<210> SEQ ID NO 81
<211> LENGTH: 15
<212> TYPE: PRT
<213> ORGANISM: Mycobacterium tuberculosis

<400> SEQUENCE: 81

Leu Asp Ser Phe Gln Leu Phe Pro Asn Phe Val Ile Leu Phe Trp
1               5                   10                  15

<210> SEQ ID NO 82

<211> LENGTH: 15
<212> TYPE: PRT
<213> ORGANISM: Mycobacterium tuberculosis

<400> SEQUENCE: 82

Ala Leu Val Leu Val Ser Leu Leu Thr Ala Leu Ala Ala Gly Ile
1 5 10 15

<210> SEQ ID NO 83
<211> LENGTH: 15
<212> TYPE: PRT
<213> ORGANISM: Mycobacterium tuberculosis

<400> SEQUENCE: 83

Ala Lys Val Leu Gly Val Phe Leu Val Thr Glu Ile Val Met Leu
1 5 10 15

<210> SEQ ID NO 84
<211> LENGTH: 15
<212> TYPE: PRT
<213> ORGANISM: Mycobacterium tuberculosis

<400> SEQUENCE: 84

Val Ala Thr Val Arg Ala Ala Ser Ser Leu Val Arg Ala Pro Leu
1 5 10 15

<210> SEQ ID NO 85
<211> LENGTH: 15
<212> TYPE: PRT
<213> ORGANISM: Mycobacterium tuberculosis

<400> SEQUENCE: 85

Val Val Leu Met Ile Phe Arg Pro Gln Gly Leu Phe Pro Ala Arg
1 5 10 15

<210> SEQ ID NO 86
<211> LENGTH: 15
<212> TYPE: PRT
<213> ORGANISM: Mycobacterium tuberculosis

<400> SEQUENCE: 86

Ala Arg Gln Met Leu Arg Phe Leu Ser Ser Pro Leu Trp Arg Ala
1 5 10 15

<210> SEQ ID NO 87
<211> LENGTH: 15
<212> TYPE: PRT
<213> ORGANISM: Mycobacterium tuberculosis

<400> SEQUENCE: 87

Thr Pro Leu Phe Met Ala His Tyr Ala Pro Phe Gly Leu Leu Thr
1 5 10 15

<210> SEQ ID NO 88
<211> LENGTH: 15
<212> TYPE: PRT
<213> ORGANISM: Mycobacterium tuberculosis

<400> SEQUENCE: 88

Val Val Tyr Ala Phe Met Ser Leu Phe Val Val Asn Val Val Val
1 5 10 15

<210> SEQ ID NO 89
<211> LENGTH: 15
<212> TYPE: PRT

<213> ORGANISM: Mycobacterium tuberculosis

<400> SEQUENCE: 89

Phe Phe His Arg Gly Leu Met Leu Met Ser Phe Asp Glu His Leu
1 5 10 15

<210> SEQ ID NO 90
<211> LENGTH: 15
<212> TYPE: PRT
<213> ORGANISM: Mycobacterium tuberculosis

<400> SEQUENCE: 90

Arg Ser Leu Met Phe Pro Thr Leu Ala Ser Leu Ile Glu Glu Arg
1 5 10 15

<210> SEQ ID NO 91
<211> LENGTH: 15
<212> TYPE: PRT
<213> ORGANISM: Mycobacterium tuberculosis

<400> SEQUENCE: 91

Asn Ala Val Leu Phe Leu Ala Ser Asp Glu Ala Arg Tyr Ile Thr
1 5 10 15

<210> SEQ ID NO 92
<211> LENGTH: 15
<212> TYPE: PRT
<213> ORGANISM: Mycobacterium tuberculosis

<400> SEQUENCE: 92

Val Leu Val Val Phe Leu Leu Pro Ala Leu Arg Asp Gly Ala Pro
1 5 10 15

<210> SEQ ID NO 93
<211> LENGTH: 15
<212> TYPE: PRT
<213> ORGANISM: Mycobacterium tuberculosis

<400> SEQUENCE: 93

Ile Val Ala His Tyr Ile Leu Gln Tyr Ala Thr Glu Glu Leu Arg
1 5 10 15

<210> SEQ ID NO 94
<211> LENGTH: 15
<212> TYPE: PRT
<213> ORGANISM: Mycobacterium tuberculosis

<400> SEQUENCE: 94

Gly Ser Val Leu Leu Val Gln Ala Leu Leu Val Thr Ser Leu Leu
1 5 10 15

<210> SEQ ID NO 95
<211> LENGTH: 15
<212> TYPE: PRT
<213> ORGANISM: Mycobacterium tuberculosis

<400> SEQUENCE: 95

Ala Ser Gly Thr Leu Leu Phe Lys Leu Thr Pro Trp Ile Val Val
1 5 10 15

<210> SEQ ID NO 96
<211> LENGTH: 15
<212> TYPE: PRT
<213> ORGANISM: Mycobacterium tuberculosis

<400> SEQUENCE: 96

Phe Glu His Ser Val Val Asn Met Phe Leu Phe Pro Ser Gly Leu
1 5 10 15

<210> SEQ ID NO 97
<211> LENGTH: 15
<212> TYPE: PRT
<213> ORGANISM: Mycobacterium tuberculosis

<400> SEQUENCE: 97

Pro Ala Ser Ile Leu Ile Leu Phe Ala Pro Gly Ala Pro Arg Glu
1 5 10 15

<210> SEQ ID NO 98
<211> LENGTH: 15
<212> TYPE: PRT
<213> ORGANISM: Mycobacterium tuberculosis

<400> SEQUENCE: 98

Leu Ala Asn Pro Gly Ile Val Ser Ile Pro Leu Ala Phe Ile Leu
1 5 10 15

<210> SEQ ID NO 99
<211> LENGTH: 15
<212> TYPE: PRT
<213> ORGANISM: Mycobacterium tuberculosis

<400> SEQUENCE: 99

Met Phe Glu Thr Met Ala Ala Phe Met Leu Val Glu His Ala Asn
1 5 10 15

<210> SEQ ID NO 100
<211> LENGTH: 15
<212> TYPE: PRT
<213> ORGANISM: Mycobacterium tuberculosis

<400> SEQUENCE: 100

Ala Leu Ile His Val Leu Trp Ile Asn Ala Gly Leu Ser Cys Asp
1 5 10 15

<210> SEQ ID NO 101
<211> LENGTH: 15
<212> TYPE: PRT
<213> ORGANISM: Mycobacterium tuberculosis

<400> SEQUENCE: 101

Gly Gln Arg Val Ile Thr Leu Leu Ala Ser Ala Asn Arg Asp Glu
1 5 10 15

<210> SEQ ID NO 102
<211> LENGTH: 15
<212> TYPE: PRT
<213> ORGANISM: Mycobacterium tuberculosis

<400> SEQUENCE: 102

Glu Gly Ile Val Phe Ala Leu Gly Gly Ala Leu Asp Phe Ser Tyr
1 5 10 15

<210> SEQ ID NO 103
<211> LENGTH: 15
<212> TYPE: PRT
<213> ORGANISM: Mycobacterium tuberculosis

<400> SEQUENCE: 103

Gly Phe Val Thr Glu Phe Leu Gln Arg Glu Val Gln Asn Phe Leu
1 5 10 15

<210> SEQ ID NO 104
<211> LENGTH: 15
<212> TYPE: PRT
<213> ORGANISM: Mycobacterium tuberculosis

<400> SEQUENCE: 104

Ser Pro Glu Gln Ala Tyr Leu Leu Leu Gly Ala Ala Pro Ile Glu
1 5 10 15

<210> SEQ ID NO 105
<211> LENGTH: 15
<212> TYPE: PRT
<213> ORGANISM: Mycobacterium tuberculosis

<400> SEQUENCE: 105

His Leu Met Gln Ser Val Val Met Val Ser Phe Pro Val Glu Val
1 5 10 15

<210> SEQ ID NO 106
<211> LENGTH: 15
<212> TYPE: PRT
<213> ORGANISM: Mycobacterium tuberculosis

<400> SEQUENCE: 106

Phe Ser Trp Phe Ala Ala Gly Met Val Leu Ala Glu Leu Thr Val
1 5 10 15

<210> SEQ ID NO 107
<211> LENGTH: 15
<212> TYPE: PRT
<213> ORGANISM: Mycobacterium tuberculosis

<400> SEQUENCE: 107

Ala Glu Leu Thr Arg Val Arg Gln Gln Val Ile Gln Leu Leu Ser
1 5 10 15

<210> SEQ ID NO 108
<211> LENGTH: 15
<212> TYPE: PRT
<213> ORGANISM: Mycobacterium tuberculosis

<400> SEQUENCE: 108

Glu Ser Phe Leu Phe Tyr Ser Gly Phe Tyr Leu Pro Met Tyr Trp
1 5 10 15

<210> SEQ ID NO 109
<211> LENGTH: 15
<212> TYPE: PRT
<213> ORGANISM: Mycobacterium tuberculosis

<400> SEQUENCE: 109

Phe Val Thr Tyr Trp Ser Phe Arg Met Met Ile Gly Leu Met Ala
1 5 10 15

<210> SEQ ID NO 110
<211> LENGTH: 15
<212> TYPE: PRT
<213> ORGANISM: Mycobacterium tuberculosis

<400> SEQUENCE: 110

Phe Thr Gly Lys Pro Glu Phe Val Glu Asn Phe Phe Met Phe Ile
1 5 10 15

<210> SEQ ID NO 111
<211> LENGTH: 15
<212> TYPE: PRT
<213> ORGANISM: Mycobacterium tuberculosis

<400> SEQUENCE: 111

Ala Pro Phe Ile Ser Glu Phe Leu Val Leu Leu Gly Thr Phe Ser
1 5 10 15

<210> SEQ ID NO 112
<211> LENGTH: 15
<212> TYPE: PRT
<213> ORGANISM: Mycobacterium tuberculosis

<400> SEQUENCE: 112

Phe Ala Ile Met Phe Glu Ala Leu Phe Ile Leu Thr Thr Val Asp
1 5 10 15

<210> SEQ ID NO 113
<211> LENGTH: 15
<212> TYPE: PRT
<213> ORGANISM: Mycobacterium tuberculosis

<400> SEQUENCE: 113

Leu Pro Phe Phe Ser Phe Met Thr Tyr Leu Ile Ala Val Pro Thr
1 5 10 15

<210> SEQ ID NO 114
<211> LENGTH: 15
<212> TYPE: PRT
<213> ORGANISM: Mycobacterium tuberculosis

<400> SEQUENCE: 114

Ala Thr Phe Ala Gly Ile Tyr Phe Trp Phe Pro Lys Met Thr Gly
1 5 10 15

<210> SEQ ID NO 115
<211> LENGTH: 15
<212> TYPE: PRT
<213> ORGANISM: Mycobacterium tuberculosis

<400> SEQUENCE: 115

Asp Arg Ile Ala Gln Leu Leu Val Gln Arg Val Glu Leu Val Glu
1 5 10 15

<210> SEQ ID NO 116
<211> LENGTH: 15
<212> TYPE: PRT
<213> ORGANISM: Mycobacterium tuberculosis

<400> SEQUENCE: 116

Ala Lys Ser Val Leu Ile Phe Leu Gly Ile Pro Leu Leu Ala Gly
1 5 10 15

<210> SEQ ID NO 117
<211> LENGTH: 15
<212> TYPE: PRT
<213> ORGANISM: Mycobacterium tuberculosis

<400> SEQUENCE: 117

Gly Arg Phe Ile Ala Leu Leu Arg Ile Phe Ala Gly Pro Leu Ala
1 5 10 15

<210> SEQ ID NO 118
<211> LENGTH: 15
<212> TYPE: PRT
<213> ORGANISM: Mycobacterium tuberculosis

<400> SEQUENCE: 118

Ile Gly Gln Phe Gly Ile Gly Phe Tyr Ser Ser Phe Met Val Ala
1 5 10 15

<210> SEQ ID NO 119
<211> LENGTH: 15
<212> TYPE: PRT
<213> ORGANISM: Mycobacterium tuberculosis

<400> SEQUENCE: 119

Ala Ser Val Ser Lys Gln Phe Thr Ala Thr Ala Ile Leu Leu Leu
1 5 10 15

<210> SEQ ID NO 120
<211> LENGTH: 15
<212> TYPE: PRT
<213> ORGANISM: Mycobacterium tuberculosis

<400> SEQUENCE: 120

Tyr Val Leu Phe Leu Phe Thr Gln Thr Val Arg His Arg Asp Phe
1 5 10 15

<210> SEQ ID NO 121
<211> LENGTH: 15
<212> TYPE: PRT
<213> ORGANISM: Mycobacterium tuberculosis

<400> SEQUENCE: 121

Ala Ser Cys Lys Tyr Met Lys Met Ile Thr Pro Ala Ala Leu Leu
1 5 10 15

<210> SEQ ID NO 122
<211> LENGTH: 15
<212> TYPE: PRT
<213> ORGANISM: Mycobacterium tuberculosis

<400> SEQUENCE: 122

Leu Ala Met Phe Ala Ile Ile Phe Phe Trp Thr Pro Pro His Thr
1 5 10 15

<210> SEQ ID NO 123
<211> LENGTH: 15
<212> TYPE: PRT
<213> ORGANISM: Mycobacterium tuberculosis

<400> SEQUENCE: 123

Met Val Ala Phe Met Val Arg Tyr Thr Ser Gly Tyr Leu Cys Val
1 5 10 15

<210> SEQ ID NO 124
<211> LENGTH: 15
<212> TYPE: PRT
<213> ORGANISM: Mycobacterium tuberculosis

<400> SEQUENCE: 124

Ala Ser Gly Leu Ile Phe Gly Trp Leu Ala Phe Leu Leu Val Phe
1 5 10 15

<210> SEQ ID NO 125
<211> LENGTH: 15

-continued

```
<212> TYPE: PRT
<213> ORGANISM: Mycobacterium tuberculosis

<400> SEQUENCE: 125

Arg Glu Leu Ile Arg Ala Phe Trp Pro Gly Ala Leu Ser Leu Val
1               5                   10                  15


<210> SEQ ID NO 126
<211> LENGTH: 15
<212> TYPE: PRT
<213> ORGANISM: Mycobacterium tuberculosis

<400> SEQUENCE: 126

Leu Ser Ser Thr Glu Phe Glu Leu Leu Arg Phe Leu Met Arg Asn
1               5                   10                  15
```